US009956405B2

(12) United States Patent
Goldwasser et al.

(10) Patent No.: US 9,956,405 B2
(45) Date of Patent: May 1, 2018

(54) TRANSDERMAL ELECTRICAL STIMULATION AT THE NECK TO INDUCE NEUROMODULATION

(71) Applicant: Thync Global, Inc., Los Gatos, CA (US)

(72) Inventors: Isy Goldwasser, Los Gatos, CA (US); Douglas Jeffery, San Jose, CA (US); Sumon K. Pal, Boston, MA (US); Wing Law, Cupertino, CA (US)

(73) Assignee: Thync Global, Inc., Los Gatos, CA (US)

( * ) Notice: Subject to any disclaimer, the term of this patent is extended or adjusted under 35 U.S.C. 154(b) by 0 days. days.

(21) Appl. No.: 15/601,394

(22) Filed: May 22, 2017

(65) Prior Publication Data
US 2017/0252562 A1    Sep. 7, 2017

Related U.S. Application Data

(60) Provisional application No. 62/431,365, filed on Dec. 7, 2016.

(51) Int. Cl.
*A61N 1/36* (2006.01)
*A61N 1/04* (2006.01)
(Continued)

(52) U.S. Cl.
CPC ......... *A61N 1/36025* (2013.01); *A61M 21/02* (2013.01); *A61N 1/0456* (2013.01); *A61N 1/0492* (2013.01); *A61M 2021/0072* (2013.01)

(58) Field of Classification Search
CPC .............. A61N 1/36025; A61N 1/0456; A61N 1/0492; A61M 21/02; A61M 2021/0072
(Continued)

(56) References Cited

U.S. PATENT DOCUMENTS 3,255,753 A   6/1966  Wing
3,620,219 A  11/1971  Barker
(Continued)

FOREIGN PATENT DOCUMENTS

EP   502919 B1   11/1993
EP   801957 A1   10/1997
(Continued)

OTHER PUBLICATIONS

Aston-Jones et al.; An integrative theory of locus coeruleus-norepinephrine function: adaptive gain and optimal performance; Annu. Rev. Neurosci.; 28: pp. 403-450; Jul. 21, 2005.
(Continued)

*Primary Examiner* — Carl H Layno
*Assistant Examiner* — Erin M Piateski
(74) *Attorney, Agent, or Firm* — Shay Glenn LLP

(57) ABSTRACT

Described herein are methods and apparatuses for the application of transdermal electrical stimulation (TES) in order to modulate a user's cognitive state to induce a state of calm or relaxation. The apparatuses described herein include neck-worn devices having electrodes (or configured to connect to electrodes, including automatically self-connecting to electrodes) adapted to couple to the midline of the back of user's neck. A neck-worn controller may be configured as a cord, band, wire, torc, necklace, loop, strap, or the like, and may be rigid or semi-rigid and may be worn at least partially around the subject's neck. The controller may controllably apply one or more waveforms to the electrodes of the electrode pad (e.g., patch) to deliver TES adapted to induce or enhance a relaxed cognitive state.

23 Claims, 47 Drawing Sheets

(51) Int. Cl.
*A61M 21/02* (2006.01)
*A61M 21/00* (2006.01)

(58) Field of Classification Search
USPC .......................................................... 607/45
See application file for complete search history.

(56) References Cited

U.S. PATENT DOCUMENTS

| | | |
|---|---|---|
| 3,648,708 A | 3/1972 | Haeri |
| 4,418,687 A | 12/1983 | Matsumoto et al. |
| 4,431,000 A | 2/1984 | Butler et al. |
| 4,646,744 A | 3/1987 | Capel |
| 4,664,117 A | 5/1987 | Beck |
| 5,144,952 A | 9/1992 | Frachet et al. |
| 5,183,041 A | 2/1993 | Toriu et al. |
| 5,335,657 A | 8/1994 | Terry et al. |
| 5,342,410 A | 8/1994 | Braverman |
| 5,397,338 A | 3/1995 | Grey et al. |
| 5,476,481 A | 12/1995 | Schondorf |
| 5,487,759 A | 1/1996 | Bastyr et al. |
| 5,514,175 A | 5/1996 | Kim et al. |
| 5,540,736 A | 7/1996 | Haimovich et al. |
| 5,573,552 A | 11/1996 | Hansjurgens |
| 5,578,065 A | 11/1996 | Hattori et al. |
| 5,593,427 A | 1/1997 | Gliner et al. |
| 5,738,647 A | 4/1998 | Bernhard et al. |
| 5,792,067 A | 8/1998 | Karell |
| 6,066,163 A | 5/2000 | John |
| 6,280,454 B1 | 8/2001 | Wang |
| 6,324,432 B1 | 11/2001 | Rigaux et al. |
| 6,445,955 B1 | 9/2002 | Michelson et al. |
| 6,463,328 B1 | 10/2002 | John |
| 6,526,318 B1 | 2/2003 | Ansarinia |
| 6,567,702 B1 | 5/2003 | Nekhendzy et al. |
| 6,731,987 B1 | 5/2004 | McAdams et al. |
| 6,983,184 B2 | 1/2006 | Price |
| 7,120,499 B2 | 10/2006 | Thrope et al. |
| 7,146,217 B2 | 12/2006 | Firlik et al. |
| 7,376,467 B2 | 5/2008 | Thrope et al. |
| 7,422,555 B2 | 9/2008 | Zabara |
| 7,577,481 B2 | 8/2009 | Firlik et al. |
| 7,660,636 B2 | 2/2010 | Castel et al. |
| 7,801,600 B1 | 9/2010 | Carbunaru et al. |
| 7,891,615 B2 | 2/2011 | Bevirt |
| 7,949,403 B2 | 5/2011 | Palermo et al. |
| 8,029,431 B2 | 10/2011 | Tononi |
| 8,086,318 B2 | 12/2011 | Strother et al. |
| 8,097,926 B2 | 1/2012 | De Graff et al. |
| 8,121,695 B2 | 2/2012 | Gliner et al. |
| 8,150,537 B2 | 4/2012 | Tanaka et al. |
| 8,190,248 B2 | 5/2012 | Besio et al. |
| 8,197,276 B2 | 6/2012 | Egloff et al. |
| 8,204,601 B2 | 6/2012 | Moyer et al. |
| 8,239,030 B1 | 8/2012 | Hagedorn et al. |
| 8,265,761 B2 | 9/2012 | Siever |
| 8,280,502 B2 | 10/2012 | Hargrove et al. |
| 8,380,315 B2 | 2/2013 | DeGiorgio et al. |
| 8,428,738 B2 | 4/2013 | Valencia |
| 8,463,383 B2 | 6/2013 | Sakai et al. |
| 8,494,625 B2 | 7/2013 | Hargrove |
| 8,494,627 B2 | 7/2013 | Bikson et al. |
| 8,506,469 B2 | 8/2013 | Dietrich et al. |
| 8,532,758 B2 | 9/2013 | Silverstone |
| 8,560,075 B2 | 10/2013 | Covalin |
| 8,571,651 B2 | 10/2013 | Ben-Ezra et al. |
| 8,583,256 B2 | 11/2013 | Tracey et al. |
| 8,612,005 B2 | 12/2013 | Rezai et al. |
| 8,639,343 B2 | 1/2014 | De Vos |
| 8,660,644 B2 | 2/2014 | Jaax et al. |
| 8,688,239 B2 | 4/2014 | Hartlep et al. |
| 8,843,210 B2 | 9/2014 | Simon et al. |
| 8,874,219 B2 | 10/2014 | Trier et al. |
| 8,903,494 B2 | 12/2014 | Goldwasser et al. |
| 8,983,621 B2 | 3/2015 | Hou et al. |
| 9,002,458 B2 | 4/2015 | Pal et al. |
| 9,014,811 B2 | 4/2015 | Pal et al. |
| 9,067,054 B2 | 6/2015 | Simon et al. |
| 9,168,374 B2 | 10/2015 | Su |
| 9,205,258 B2 | 12/2015 | Simon et al. |
| 9,233,244 B2 | 1/2016 | Pal et al. |
| 9,248,292 B2 | 2/2016 | Trier et al. |
| 9,333,334 B2 | 5/2016 | Jeffery et al. |
| 9,364,674 B2 | 6/2016 | Cook et al. |
| 9,393,401 B2 | 7/2016 | Goldwasser et al. |
| 9,393,430 B2 | 7/2016 | Demers et al. |
| 9,399,126 B2 | 7/2016 | Pal et al. |
| 9,415,219 B2 | 8/2016 | Simon et al. |
| 9,440,070 B2 | 9/2016 | Goldwasser et al. |
| 9,446,242 B2 | 9/2016 | Griffith |
| 9,474,891 B2 | 10/2016 | Demers et al. |
| 9,474,905 B2 | 10/2016 | Doan et al. |
| 9,517,351 B2 | 12/2016 | Charlesworth et al. |
| 9,656,076 B2 | 5/2017 | Trier et al. |
| 9,700,725 B2 | 7/2017 | Zhu |
| 9,731,116 B2 | 8/2017 | Chen |
| 9,744,347 B2 | 8/2017 | Chen et al. |
| 9,764,133 B2 | 9/2017 | Thomas et al. |
| 9,782,587 B2 | 10/2017 | Trier et al. |
| 2002/0116036 A1 | 8/2002 | Daignault et al. |
| 2003/0171685 A1 | 9/2003 | Lesser et al. |
| 2003/0225323 A1 | 12/2003 | Klani et al. |
| 2004/0098065 A1 | 5/2004 | Hagglof et al. |
| 2004/0267333 A1 | 12/2004 | Kronberg |
| 2005/0165460 A1 | 7/2005 | Erfan |
| 2005/0267388 A1 | 12/2005 | Hanna |
| 2006/0064139 A1 | 3/2006 | Chung et al. |
| 2006/0149119 A1 | 7/2006 | Wang |
| 2006/0206163 A1 | 9/2006 | Wahlstrand et al. |
| 2007/0088419 A1 | 4/2007 | Fiorina et al. |
| 2007/0100275 A1 | 5/2007 | Fischer et al. |
| 2007/0173890 A1 | 7/2007 | Armstrong |
| 2007/0213790 A1 | 9/2007 | Nolan et al. |
| 2007/0276451 A1 | 11/2007 | Rigaux |
| 2008/0045882 A1 | 2/2008 | Finsterwald |
| 2008/0132974 A1 | 6/2008 | Strother et al. |
| 2008/0208266 A1 | 8/2008 | Lesser et al. |
| 2008/0215113 A1* | 9/2008 | Pawlowicz ........ A61N 1/36021 607/46 |
| 2008/0275293 A1 | 11/2008 | Lattner et al. |
| 2008/0281368 A1 | 11/2008 | Bulkes et al. |
| 2008/0319505 A1 | 12/2008 | Boyden et al. |
| 2009/0048642 A1 | 2/2009 | Goroszeniuk |
| 2009/0099623 A1 | 4/2009 | Bentwich |
| 2009/0112280 A1 | 4/2009 | Wingeier et al. |
| 2009/0177243 A1 | 7/2009 | Lebedev et al. |
| 2009/0210028 A1 | 8/2009 | Rigaux et al. |
| 2009/0240303 A1 | 9/2009 | Wahlstrand et al. |
| 2009/0270947 A1 | 10/2009 | Stone et al. |
| 2009/0287108 A1 | 11/2009 | Levy |
| 2010/0057154 A1 | 3/2010 | Dietrich et al. |
| 2010/0145399 A1 | 6/2010 | Johari et al. |
| 2010/0152817 A1 | 6/2010 | Gillbe |
| 2010/0256436 A1 | 10/2010 | Partsch et al. |
| 2011/0029045 A1 | 2/2011 | Cevette et al. |
| 2011/0082326 A1 | 4/2011 | Mishelevich et al. |
| 2011/0082515 A1 | 4/2011 | Libbus et al. |
| 2011/0093033 A1 | 4/2011 | Nekhendzy |
| 2011/0112394 A1 | 5/2011 | Mishelevich |
| 2011/0112590 A1 | 5/2011 | Wu et al. |
| 2011/0114191 A1 | 5/2011 | Wheater et al. |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0172752 A1 | 7/2011 | Bingham et al. |
| 2011/0190846 A1 | 8/2011 | Ruffini et al. |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270345 A1 | 11/2011 | Johnston et al. |
| 2011/0276112 A1 | 11/2011 | Simon et al. |
| 2011/0288610 A1 | 11/2011 | Brocke |
| 2011/0319950 A1 | 12/2011 | Sullivan |
| 2012/0016431 A1 | 1/2012 | Paul et al. |
| 2012/0029591 A1 | 2/2012 | Simon et al. |

(56) References Cited

U.S. PATENT DOCUMENTS

| | | |
|---|---|---|
| 2012/0029601 A1 | 2/2012 | Simon et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0185020 A1 | 7/2012 | Simon et al. |
| 2012/0209346 A1 | 8/2012 | Bikson et al. |
| 2012/0245409 A1 | 9/2012 | Liang |
| 2012/0245653 A1 | 9/2012 | Bikson et al. |
| 2012/0302912 A1 | 11/2012 | Moffitt et al. |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0131551 A1 | 5/2013 | Raghunathan et al. |
| 2013/0158627 A1 | 6/2013 | Gozani et al. |
| 2013/0184779 A1 | 7/2013 | Bikson et al. |
| 2013/0204315 A1 | 8/2013 | Wongsarnpigoon et al. |
| 2013/0226275 A1 | 8/2013 | Duncan |
| 2013/0267761 A1 | 10/2013 | Bentwich |
| 2013/0282095 A1 | 10/2013 | Mignolet et al. |
| 2013/0304175 A1 | 11/2013 | Voegele et al. |
| 2013/0318168 A1 | 11/2013 | Demain et al. |
| 2013/0325096 A1 | 12/2013 | Dupelle et al. |
| 2014/0031895 A1 | 1/2014 | Rahimi et al. |
| 2014/0128944 A1 | 5/2014 | Stern et al. |
| 2014/0257449 A1 | 9/2014 | Helmer |
| 2014/0277324 A1 | 9/2014 | DiUbaldi et al. |
| 2014/0336728 A1 | 11/2014 | Franke et al. |
| 2015/0005841 A1* | 1/2015 | Pal ................... A61N 1/0476 607/45 |
| 2015/0088224 A1* | 3/2015 | Goldwasser ....... A61N 1/36082 607/45 |
| 2015/0257970 A1* | 9/2015 | Mucke ................ A61N 1/0476 601/21 |
| 2015/0335877 A1 | 11/2015 | Jeffery et al. |
| 2016/0008632 A1 | 1/2016 | Wetmore et al. |
| 2016/0074657 A1 | 3/2016 | Kwan et al. |
| 2016/0317809 A1 | 11/2016 | Pal et al. |
| 2016/0346530 A1 | 12/2016 | Jeffery et al. |
| 2016/0346545 A1 | 12/2016 | Pal et al. |
| 2017/0076414 A1 | 3/2017 | Egnal et al. |

FOREIGN PATENT DOCUMENTS

| | | |
|---|---|---|
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| JP | 49061984 A | 6/1974 |
| JP | 05031197 A | 2/1993 |
| JP | 10108913 A | 4/1998 |
| JP | 2002306604 A | 10/2002 |
| JP | 200310230 A | 1/2003 |
| JP | 2006192302 A | 7/2006 |
| JP | 3129187 U | 1/2007 |
| JP | 200985901 A | 4/2009 |
| JP | 2011118293 A | 6/2011 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO01/78834 A1 | 10/2001 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2009/147599 A1 | 12/2009 |
| WO | WO2010/047834 A1 | 4/2010 |
| WO | WO2010/067145 A1 | 6/2010 |
| WO | WO2011/147546 A1 | 12/2011 |
| WO | WO2012/082960 A2 | 6/2012 |
| WO | WO2012/089588 A1 | 7/2012 |
| WO | WO2012/116407 A1 | 9/2012 |
| WO | WO2012/129574 A2 | 9/2012 |
| WO | WO2012/150600 A2 | 11/2012 |
| WO | WO2012/156051 A1 | 11/2012 |
| WO | WO2012/156052 A2 | 11/2012 |
| WO | WO2013/071307 A1 | 5/2013 |
| WO | WO2013/192582 A1 | 12/2013 |
| WO | WO2014/107624 A1 | 7/2014 |
| WO | WO2015/061663 A1 | 4/2015 |
| WO | WO2015/143053 A1 | 9/2015 |
| WO | WO2015/183690 A1 | 12/2015 |

OTHER PUBLICATIONS

Aston-Jones et al.; Role of locus coeruleus in attention and behavioral flexibility; Biological Psychiatry; 46(9); pp. 1309-1320; Nov. 1, 1999.

Axelgaard Manufacturing Co. Ltd.; Little PALS® (product information); 2 pgs.; printed Feb. 11, 2013 from http://www.axelgaard.com/prod_little-pals.html.

Axelgaard Manufacturing Co. Ltd.; PALS® Platinum Blue (product information); 2 pgs.; printed Feb. 11, 2013 from http://www.axelgaard.com/prod_pals-platinum-blue.html.

Backhaus et al.; Sleep disturbances are correlated with decreased morning awakening salivary cortisol; Psychoneuroendocrinology; 29(9): pp. 1184-1191; Oct. 31, 2004.

Basta et al.; Chronic Insomnia and the Stress System; Sleep Medicine Clinics; 2(2): pp. 279-1291; (Author Manuscript, 20 pages); Jun. 30, 2007.

Berlad et al.; Power spectrum analysis and heart rate variability in Stage 4 and REM sleep: evidence for state-specific changes in autonomic dominance; Journal of Sleep Research; 2(2): pp. 88-90; Jun. 1, 1993.

Berridge et al.; The locus coeruleus-noradrenergic system: modulation of behavioral state and state-dependent cognitive processes; Brain Research Reviews; 42(1); pp. 33-84; Apr. 30, 2003.

Brown et al.; Control of sleep and wakefulness; Physiological reviews; 92(3); pp. 1087-1187; Jul. 1, 2012.

Brown et al.;Locus ceruleus activation suppresses feedforward interneurons and reduces beta-gamma electroencephalogram frequencies while it enhances theta frequencies in rat dentate gyrus; Journals of Neuroscience; 25(8): pp. 1985-1991; Feb. 23, 2005.

Buchanan et al.; Salivary alpha-amylase levels as a biomarker of experienced fear; Communicative and Integrative Biology; 3(6); pp. 525-527; Nov. 1, 2010.

Buckley et al.; On the Interactions of the Hypothalamic-Pituitary-Adrenal (HPA) Axis and Sleep: Normal HPA Axis Activity and Circadian Rhythm, Exemplary Sleep Disorders; The Journal of Clinical Endocrinology and Metabolism; 90 (5); pp. 3106-3114; May 1, 2005.

Buysse et al.; The Pittsburgh Sleep Quality Index: a new instrument for psychiatric practice and research; Psychiatric Research; 28(2); pp. 193-213; May 31, 1989.

Carter et al.; Tuning arousal with optogenetic modulation of locus coeruleus neurons; Nature Neuroscience; 13(12); pp. 1526-1533; Dec. 1, 2010.

Chaieb et al.; Transcranial alternating current stimulation in the low kHz range increases motor cortex excitability; Restor Neurol Neurosci; 29(3); pp. 167-175; Mar. 2011.

Cook et al.; Trigeminal nerve stimulation in major depressive disorder: acute outcomes in an open pilot study; Epilepsy and Behavior; 28(2); pp. 221-226; Aug. 31, 2013.

Coutinho et al.; Musical emotions: predicting second-by-second subjective feelings of emotion from low-level psychoacoustic features and physiological measurements; Emotion; 11(4); pp. 921-937; Aug. 2011.

DaSilva et al.; Electrode positioning and montage in transcranial direct current stimulation; J Vis Exp; 51; e2744; 11 pgs.; May 2011.

(56) References Cited

OTHER PUBLICATIONS

Degiorgio et al., Trigeminal nerve stimulation for epilepsy: long-term feasibility and efficacy; Neurology; 72(10): pp. 936-938; Mar. 10, 2009.
Degiorgio et al.; Randomized controlled trial of trigeminal nerve stimulation for drug-resistant epilepsy; Neurology; 80(9); pp. 786-791; Feb. 26, 2013.
Digitimer Ltd.; DS2 and DS3 Isolated Stimulator (product information); 2 pgs.; downloaded from http://www.digitimer.com/research/stimulators/index.htm on Feb. 10, 2014.
Elder et al.; The cortisol awakening response—applications and implications for sleep medicine; Sleep Medicine Reviews; 18(3): pp. 215-224; Jun. 30, 2014.
Electozyme; Company and Product Information; 3 pgs.; printed Feb. 11, 2014 from http://electrozyme.com/applications/.
Eschenko et al.; Noradrenergic neurons of the locus coeruleus are phase locked to cortical up-down states during sleep; Cerebral Cortex; 22(2); pp. 426-435; Feb. 1, 2012.
Feurra et al.; Frequency specific modulation of human somatosensory cortex; Front Psychol; 2(13); 6 pgs.; Feb. 2011.
Franowicz et al.; Treatment with the noradrenergic alpha-2 agonist clonidine, but not diazepam, improves spatial working memory in normal young rhesus monkeys; Neuropsychopharmacology; 21(5); pp. 611-621; Nov. 1, 1999.
Garraway et al.; Modulatory actions of serotonin, norepinephrine, dopamine, and acetylcholine in spinal cord deep dorsal horn neurons; Journal of Neurophysiology; 86(5); pp. 2183-2194; Nov. 1, 2001.
GoFLOW; tDCS Kit; product information; 9 pgs..; printed Feb. 10, 2014 (http://flowstateengaged.com/).
Golestanirad et al; Analysis of fractal electrodes for efficient neural stimulation; Frontiers in Neurengineering; 6(3); 10 pages; Jul. 2013.
Gracenote; Timeline-metadata-api; 3 pages; retrieved from the Internet Jul. 7, 2015; (https://github.com/gracenote/timeline-metadata-api/blob/master/README.md).
Granger et al.; Salivary alpha-amylase in biobehavioral research: recent developments and applications; Annals of the New York Academy of Sciences; 1098(1); pp. 122-144; Mar. 1, 2007.
Grindhouse Wetware; Thinking Cap; product information; 1 pg.; printed Feb. 10, 2014 (http://www.grindhousewetware.com/thinkingcap.html).
Gummadavelli et al.; Neurostimulation to improve level of consciousness in patients with epilepsy. Neurosurgical Focus; 38(6); pp. E10; (manuscript version,14 pages); Jun. 2015.
Hajos et al.; Norepinephrine but not serotonin reuptake inhibitors enhance theta and gamma activity of the septo-hippocampal system; Neuropsychopharmacology; 28(5); pp. 857-864; May 1, 2003.
Hass et al.; Waking with the hypothalamus. Pflugers Arch R Eur. J. Physiol.; 463(1): pp. 31-42; Jan. 1, 2012.
Herwig et al.; Intracortical excitability is modulated by a norepinephrine-reuptake inhibitor as measured with paired-pulse transcranial magnetic stimulation; Psychopharmacology (Berl); 164(2): pp. 228-232; Nov. 18, 2002.
Hirotsu et al.; Interactions between sleep, stress, and metabolism; From physiological to pathological conditions; Sleep Science; 8(3); pp. 143-152; Nov. 2015.
Horvath et al.; Evidence that transcranial direct current stimulation (tDCS) generates little-to-no reliable neurophysiologic effect beyond MEP amplitude modulation in healthy human subjects: A systematic review; Neuropsychologia; 66: pp. 213-236; Jan. 31, 2015.
Just et al.; Bold responses to trigeminal nerve stimulation; Magnetic Resonance Imaging; 28(8): pp. 1143-1151; Oct. 31, 2010.
Kanai et al.; Frequency-dependent electrical stimulatioin of the visual cortex; Curr. Biol.; 18(23); pp. 1839-1843; Dec. 9, 2008.
Kubota et al.; Role of the brain stem in cardiovascular changes induced by stimulation of the trigeminal nerve; Anesthesia Progress; 36(4-5); pp. 236-237; Jul. 1989.
Lee et al.; Neuromodulation of Brain States; Neuron; 76(1): pp. 209-222. Oct. 4, 2012.
Leproult et al.; Sleep loss results in an elevation of cortisol levels the next evening; Sleep; 20(10): pp. 865-870; Oct. 1997.
Lovibond et al.; The structure of negative emotional states: Comparison of the Depression Anxiety Stress Scales (DASS) with the Beck Depression and Anxiety Inventories; Behaviour Research and Therapy; 33(3); pp. 335-343; Mar. 31, 1995.
Lu et al.; A putative flip-flop switch for control of REM sleep; Nature; 441 (7093): pp. 589-594; Jun. 1, 2006.
Magis et al.; Safety and patients' satisfaction of transcutaneous supraorbital neurostimulation (tSNS) with the Cefaly(R) device in headache treatment: a survey of 2,313 headache sufferers in the general population; The Journal of Headache and Pain, 14(1); pp. 95; (manuscript version, 8 pages) Dec. 1, 2013.
McGough et al.; An eight-week, open-trial, pilot feasibility study of trigeminal nerve stimulation in youth with attention-deficit/hyperactivity disorder; Brain Stimulation; 8(2); pp. 299-304; Apr. 30, 2015.
Meltzer et al; Direct comparison of two new actigraphs and polysomnography in children and adolescents; Sleep; 35(1); pp. 159-166; Jan. 1, 2012.
Nash et al.; Differential activation of the human trigeminal nuclear complex by noxious and non-noxious orofacial stimulation; Human Brain Mapping; 30(11); pp. 3772-3782; Nov. 1, 2009.
Nieuwenhuis et al.; Decision making, the P3, and the locus coeruleus-norepinephrine system; Psychological Bulletin; 131(4); pp. 510-532; Jul. 2005.
Parvizi et al.; Consciousness and the brainstem; Cognition; 79(1): pp. 135-60; Apr. 30, 2001.
Paulus, W.; Transcranial electrical stimulation (tES-tDCS; tRNS, tACS) methods; Neuropsychol Rehabil.; 21(5); pp. 602-617; Oct. 2011.
Penzel et al.; Dynamics of Heart Rate and Sleep Stages in Normals and Patients with Sleep Apnea; Neuropsychopharmacology; 28(S1); pp. S48-553; Jul. 1, 2003.
Piquet et al.; Supraorbital transcutaneous neurostimulation has sedative effects in healthy subjects; BMC Neurology; 11(1); p. 135; (manual transcript, 8 pages); Oct. 28, 2011.
Plewnia et al.; Enhancement of human cortico- motoneuronal excitability by the selective norepinephrine reuptake inhibitor reboxetine; Neuroscience Letters; 330(3); pp. 231-234; Sep. 27, 2002.
Prausnitz; The effects of electric current applied to skin: a review for transdermal drug delivery; Advanced Drug Delivery Reviews; vol. 18; pp. 395-425; Feb. 8, 1996.
Pusch et al.; Electrical stimulation of the vestibular system prevents postoperative nausea and vomiting; Acta Annesthesiol Scand.; 44(9); pp. 1145-1148; Oct. 2000.
Riemann et al.; The hyperarousal model of insomnia: A review of the concept and its evidence; Sleep Medicine Reviews; 14(1); pp. 19-31; Feb. 28, 2010.
Rill et al.; Pedunculopontine arousal system physiology—implications for insomnia; Sleep Science; 8(2); pp. 92-99; Jun. 30, 2015.
Rohleder et al.; Psychosocial stress-induced activation of salivary alpha-amylase: an indicator of sympathetic activity; Annals of the New York Academy of Sciences; 1032(1); pp. 258-263; Dec. 1, 2004.
Saiote et al.; High-frequency TRNS reduces BOLD activity during visuomotor learning; PLOS one; 8(3); e59669; 8 pgs.; Mar. 2013.
Sara; The locus coeruleus and noradrenergic modulation of cognition; Nature Reviews Neuroscience; 10(3): pp. 211-223. Mar. 1, 2009.
Schmidt et al.; Adrenaline rush: the role of adrenergic receptors in stimulant-induced behaviors; Molecular Pharmacology; 85(4): pp. 640-650; Apr. 1, 2014.
Schutter et al.; Brain oscillations and frequency-dependent modulation of cortical excitability; Brain Stimulation; 4(2); pp. 97-103; Apr. 2011.
Seugnet et al.; Identification of a biomarker for sleep drive in flies and humans; Proceedings of the National Academy of Sciences; 103(52); pp. 19913-19918; Dec. 26, 2006.
Shiozawa et al.; Transcutaneous vagus and trigeminal nerve stimulation for neuropsychiatric disorders: a systematic review; Arquivos de neuro-psiquiatria; 72(7): pp. 542-547; Jul. 2014.

(56) References Cited

OTHER PUBLICATIONS

Siegel; Brain mechanisms that control sleep and waking. Naturwissenschaften; 91(8); pp. 355-365; Aug. 1, 2004.

Somana et al.; Cerebellar afferents from the trigeminal sensory nuclei in the cat. Brain Res.; 38(1); pp. 57-64; Jan. 1980.

STD Pharmaceutical Products; Idrostar intophoresis machine (product and use information); 9 pgs.; Dec. 2011 (printed Feb. 11, 2014 from http://www.iontophoresis.info/instructions/).

Strassman et al; Response of brainstem trigeminal neurons to electrical stimulation of the dura; Brain Research; 379(2): pp. 242-250; Aug. 6, 1986.

Tanaka et al.; Salivary alpha-amylase and cortisol responsiveness following electrically stimulated physical stress in bipolar disorder patients; Neuropsychiatric Disease and Treatment; 8; pp. 1899-1905; Jan. 1, 2013.

Terney et al.; Increasing human brain excitability by transcranial high-frequency random noise stimulation; The Journal of Neuroscience; 28(52); pp. 14127-14155; Dec. 2008.

Thoma et al.; Acute stress responses in salivary alpha-amylase predict increases of plasma norepinephrine; Biological Psychology; 91(3): pp. 342-348; Dec. 31, 2012.

Tremblay et al.; Uncertain Outcome of Prefrontal tDCS; Brain Stimulation; 7(6): pp. 773-783; Dec. 31, 2014.

Trevizol et al.; Trigeminal Nerve Stimulation (TNS) for Generalized Anxiety Disorder: A Case Study; Brain Stimulation; 8(3): pp. 659-660; Jan. 1, 2015.

Trevizol et al.; Trigeminal Nerve Stimulation (TNS) for Posttraumatic Stress Disorder: A Case Study; Brain Stimulation; 8(3): pp. 676-678; Jan. 1, 2015.

Turi et al.; Both the cutaneous sensation and phosphene perception are modulated in a frequency-specific manner during transcranial alternating current stimulation; Rester. Neurol. Neurosci.; 31(3); pp. 275-285; Jan. 2013.

Tyler et al.; Transdermal neuromodulation of noradrenergic activity suppresses psychophysiological and biochemical stress responses in humans; Scientific Reports; 5; (manual transcript, 22 pages); Feb. 8, 2015.

Tyler et al.; U.S. Appl. No. 61/550,334 entitled "Improvement of Direct Communication," filed Oct. 21, 2011.

Tyler et al.; U.S. Appl. No. 61/663,409 entitled "Device and Methods for Noninvasive Neuromodulation Using Targeted Transcranial Electrical Stimulation," filed Jun. 22, 2012.

Tyler et al.; U.S. Appl. No. 62/166,674 entitled "Systems and Methods for Suppression of Stress Responses by Transdermal Electrical Neuromodulation," filed May 26, 2015.

Upadhyay et al.; Noninvasive mapping of human trigeminal brainstem pathways; Magnetic Resonance in Medicine; 60(5): pp. 1037-1046; Nov. 1, 2008.

Van Stegeren et al.; Salivary alpha amylase as marker for adrenergic activity during stress: effect of betablockade; Psychoneuroendocrinology; 31(1); pp. 137-141; Jan. 31, 2006.

Voisin et al.; Nociceptive stimulation activates locus coeruleus neurones projecting to the somatosensory thalamus in the rat; The Journal of Physiology; 566( 3); pp. 929-937; Aug. 1, 2005.

Voss et al.; Induction of self awareness in dreams through frontal low current stimulation of gamma activity; Nature Neuroscience; 17(6); pp. 810-812; Jun. 1, 2014.

Watson et al.; Development and validation of brief measures of positive and negative affect: the PANAS scales; Jouranl of Personality and Social Psychology; 54(6); pp. 1063-1070; Jun. 1988.

Weiss et al; Validity of Activity-Based Devices to Estimate Sleep; Journal of Clinical Sleep Medicine : 6(4); pp. 336-342; Aug. 2010.

Goldwasser et al.; U.S. Appl. No. 15/264,224 entitled "Apparatuses and methods for neuromodulation," filed Sep. 13, 2016.

Charlesworth et al.; U.S. Appl. No. 15/384,249 entitled "Apparatuses and methods for transdermal electrical stimulation of nerves to modify or induce a cognitive state," filed Dec. 19, 2017.

Jeffery; U.S. Pat. Appl. No. 15/380,028 entitled "Electrodes having surface exclusions," filed Dec. 15, 2016.

Tyler et al.; U.S. Appl. No. 15/460,138 entitled "Systems and methods for transdermal electrical stimulation to improve sleep," filed Mar. 15, 2017.

Pal et al.; U.S. Appl. No. 14/956,193 entitled "Transdermal electrical stimulation devices for modifying or inducing cognitive state," filed Dec. 1, 2015.

Tyler et al.; U.S. Appl. No. 15/536,148 entitled "Methods and apparatuses for transdermal stimulation of the outer ear," filed Jun. 15, 2017.

Tyler et al.; U.S. Appl. No. 15/536,151 entitled "Systems and methods for transdermal electrical stimulation to improve sleep," filed Jun. 15, 2017.

\* cited by examiner

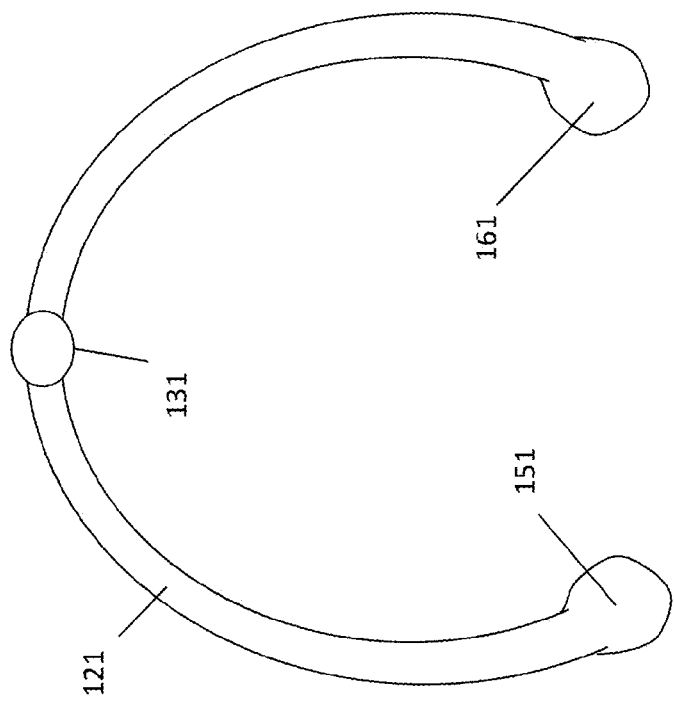
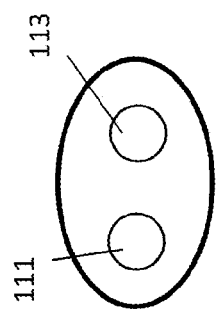
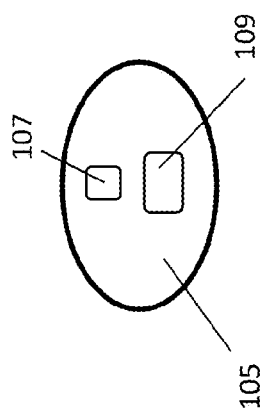
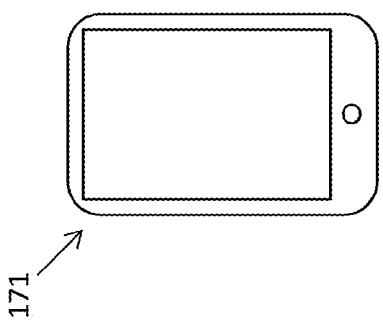
FIG. 1C
FIG. 1B
FIG. 1A
FIG. 1D

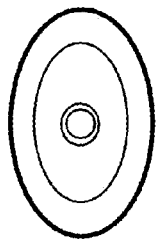
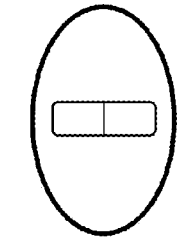
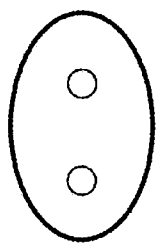
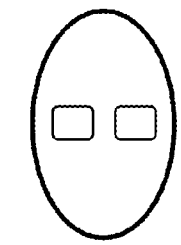
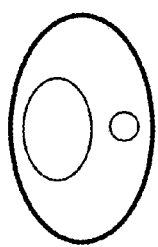
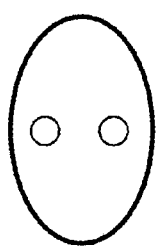
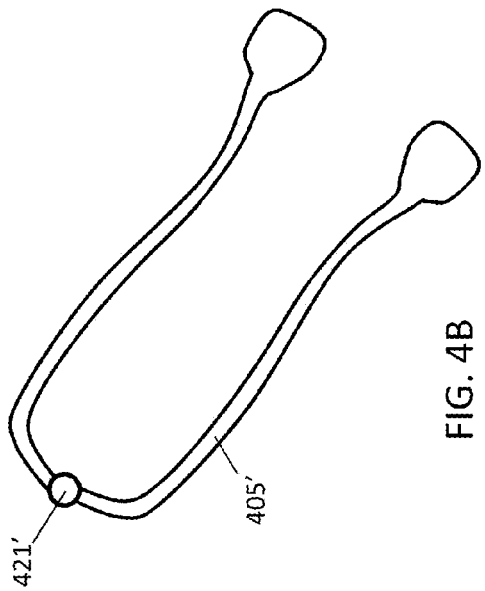
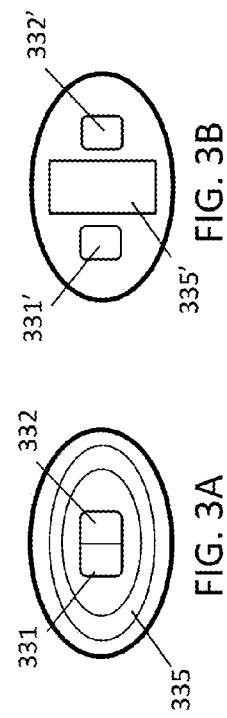
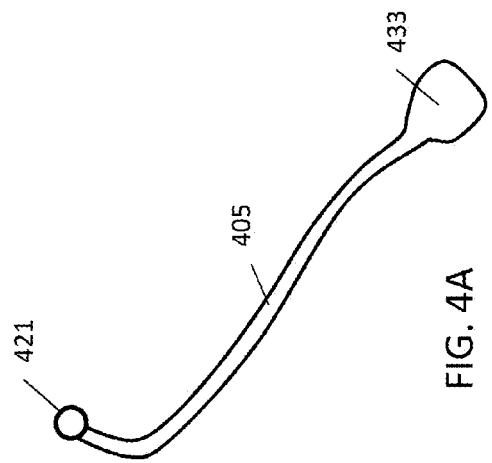

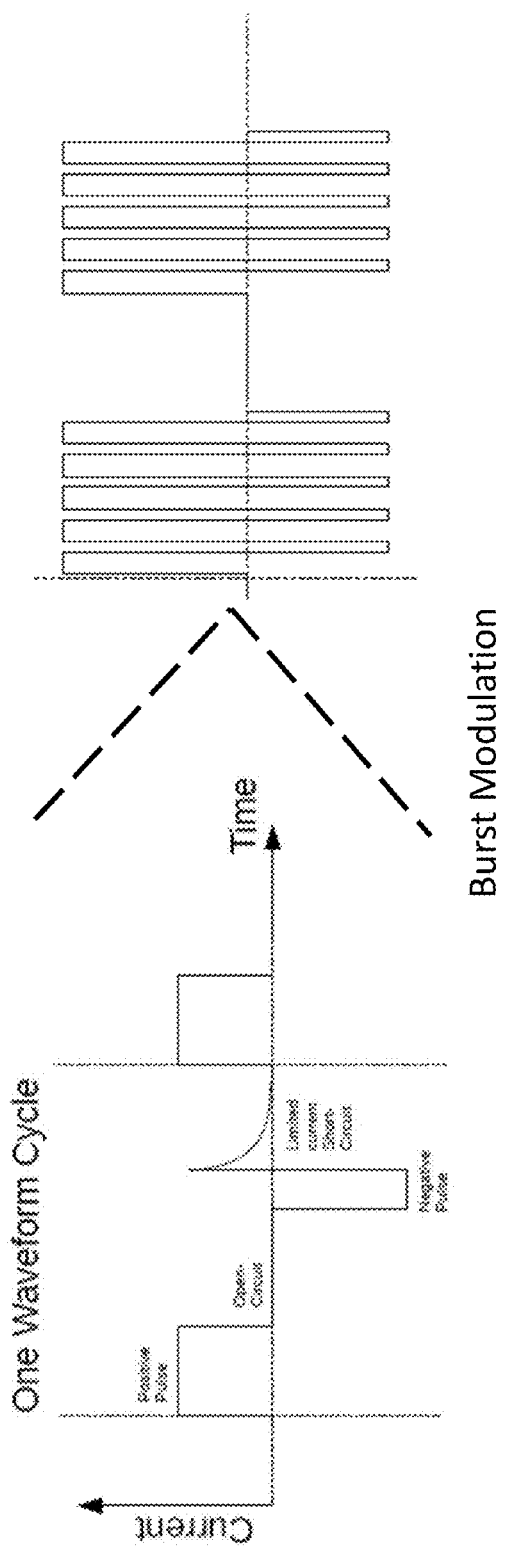
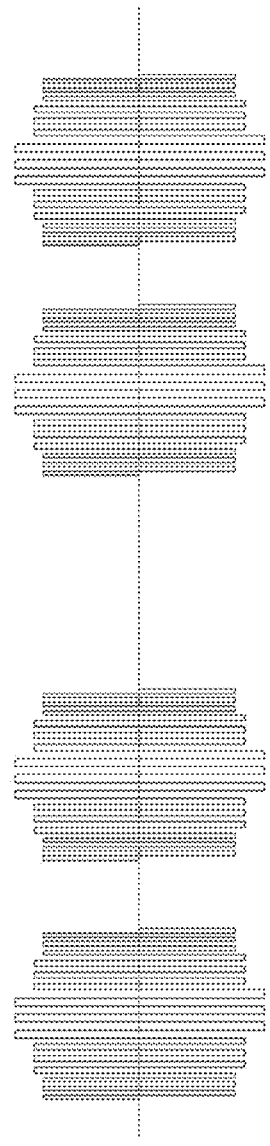
FIG. 21A Burst Modulation
FIG. 21B Amplitude and Frequency Modulation

| End Time (sec) | 15 | 45 | 55 | 80 | 110 | 120 | 140 | 465 | 480 | 495 | 555 | 560 | 600 |
|---|---|---|---|---|---|---|---|---|---|---|---|---|---|
| Duration (sec) | 15 | 30 | 10 | 25 | 30 | 10 | 20 | 25 | 15 | 15 | 60 | 5 | 40 |
| Frequency (Hz) | 15000 | 15000 | 15000 | 15000 | 15000 | 15000 | 15000 | 1560 | 1560 | 1560 | 1560 | 1560 | 1560 |
| Peak Current (mA) | 27.9 | 27.9 | 30 | 30 | 30 | 30 | 30 | 13.5 | 13.5 | 14.4 | 14.4 | 14.4 | 15 |
| % DC | 60 | 60 | 60 | 60 | 60 | 60 | 60 | 60 | 60 | 60 | 60 | 60 | 60 |
| % Duty Cycle | 67 | 67 | 68 | 68 | 68 | 68 | 68 | 20 | 20 | 20 | 20 | 20 | 20 |
| AM Duty Cycle | 50 | 50 | 50 | 50 | 50 | 50 | 50 | 80 | 80 | 80 | 80 | 80 | 80 |
| AM Frequency (Hz) | 800 | 800 | 800 | 400 | 800 | 800 | 400 | 52 | 52 | 52 | 52 | 52 | 52 |
| AM Flat Ratio (%) | 100 | 100 | 1 | 1 | 1 | 1 | 1 | 100 | 100 | 1 | 1 | 1 | 1 |
| AM Symmetry Ratio (%) | 50 | 50 | 1 | 1 | 1 | 1 | 1 | 50 | 50 | 1 | 1 | 1 | 1 |
| AM DC Offset (%) | 0 | 0 | 1 | 1 | 1 | 50 | 50 | 0 | 0 | 0 | 0 | 50 | 50 |

Rows 3–4 grouped as "Carrier Wave"; rows 5–6 as "Amplitude Modulation".

FIG. 23

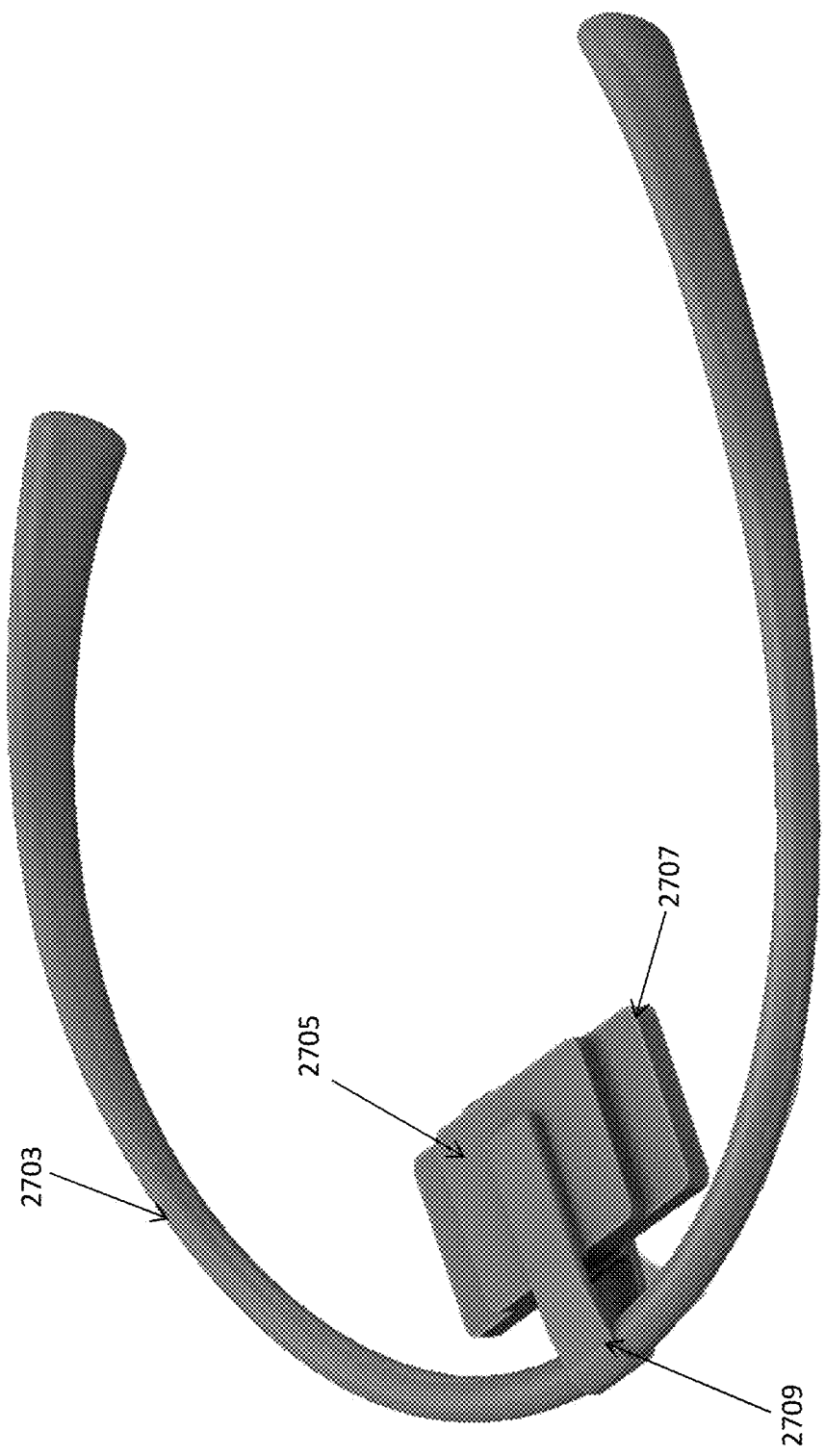

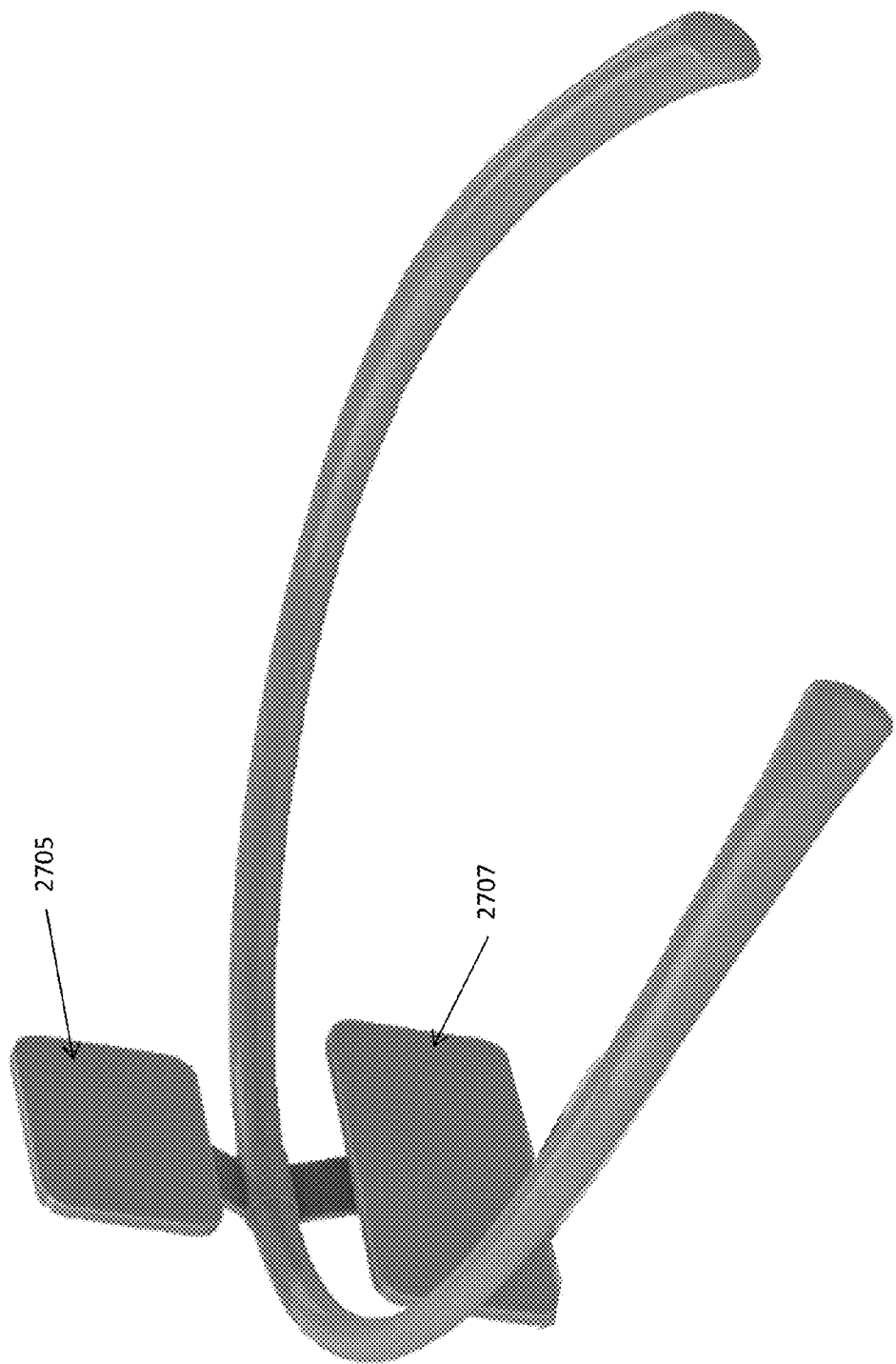

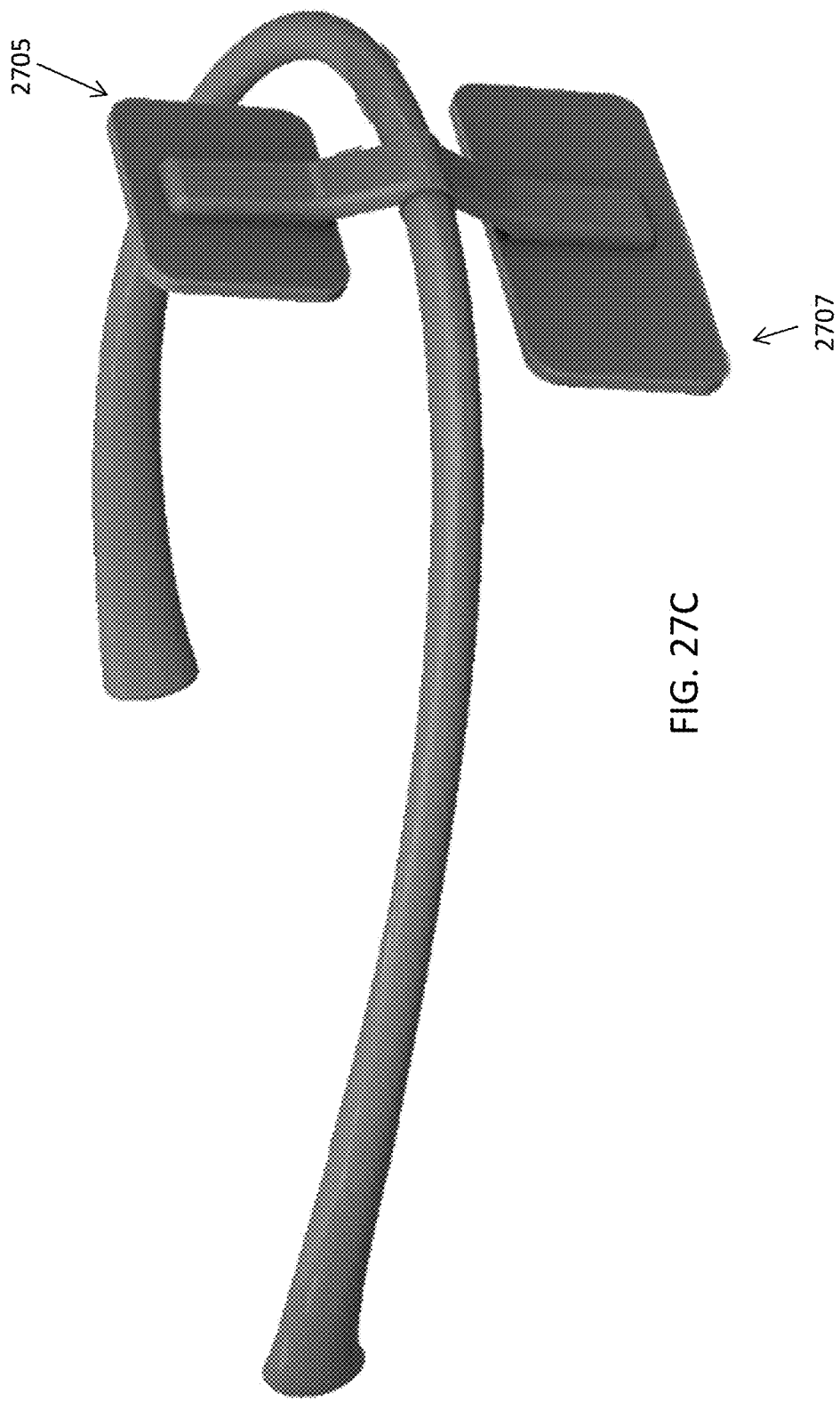

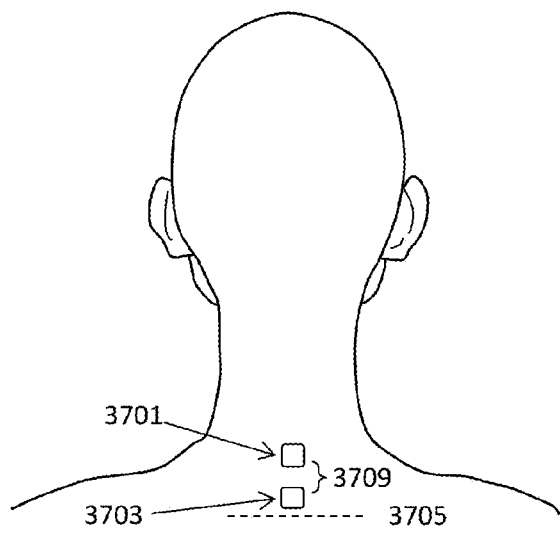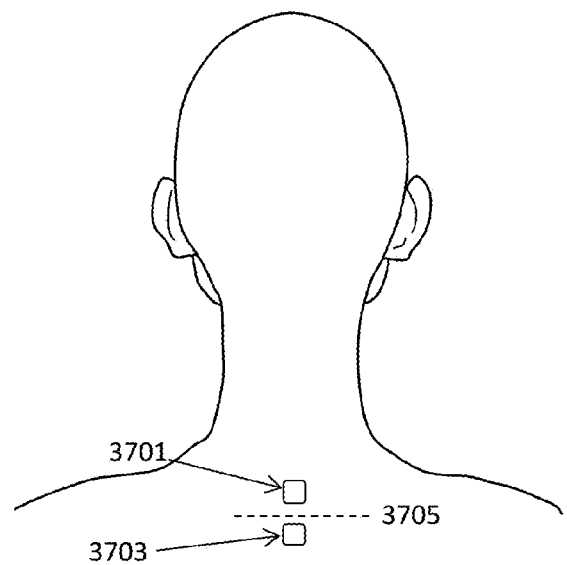
FIG. 37A  FIG. 37B
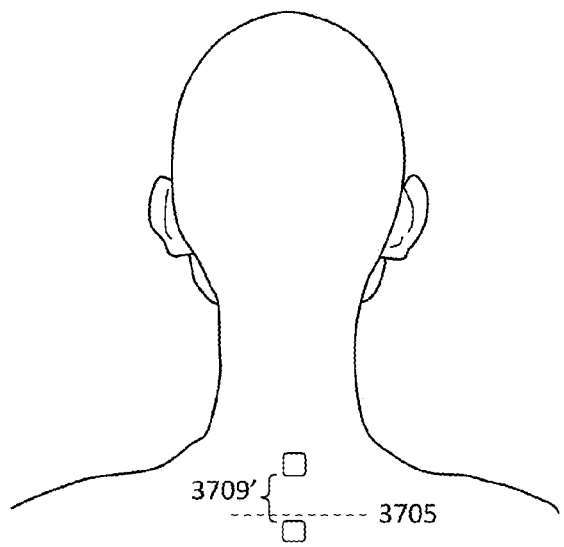
FIG. 37C

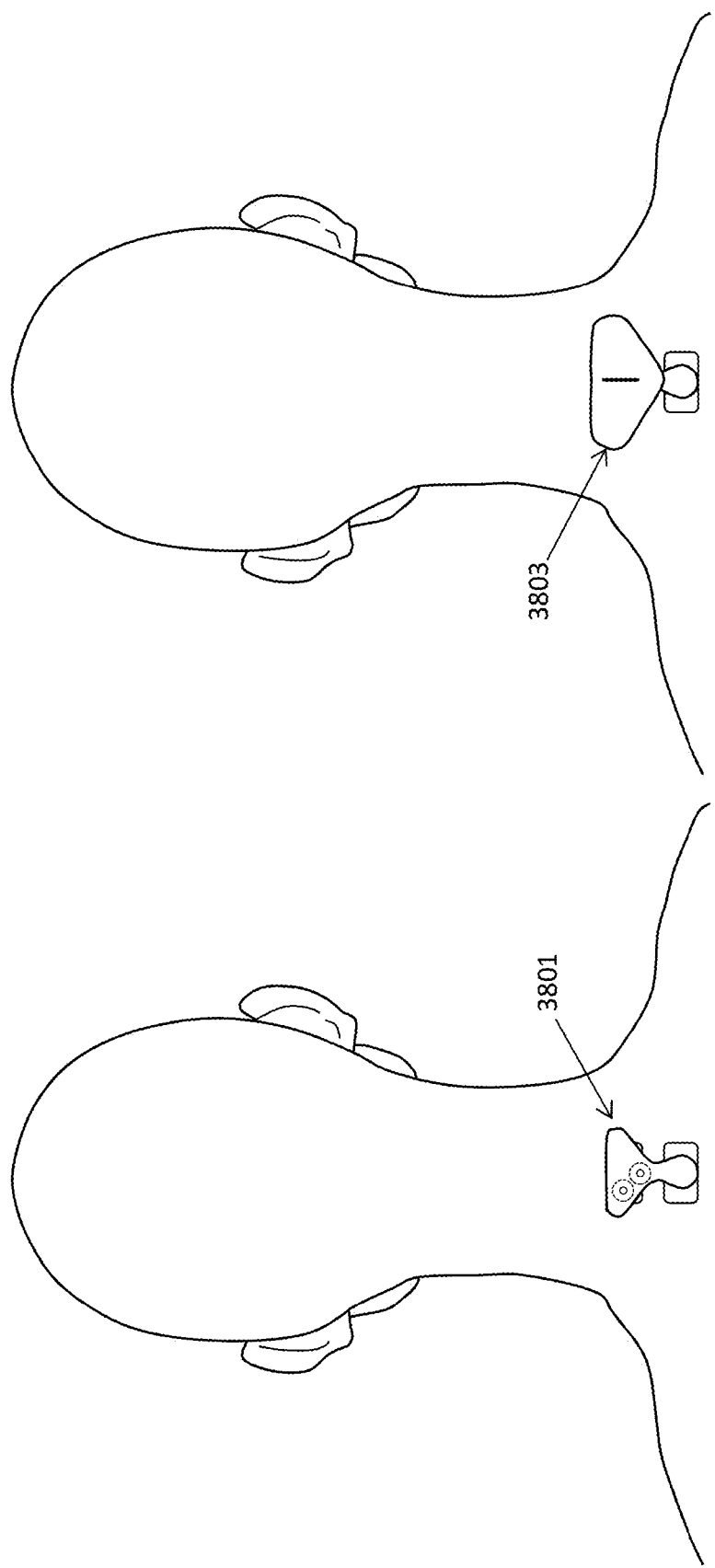

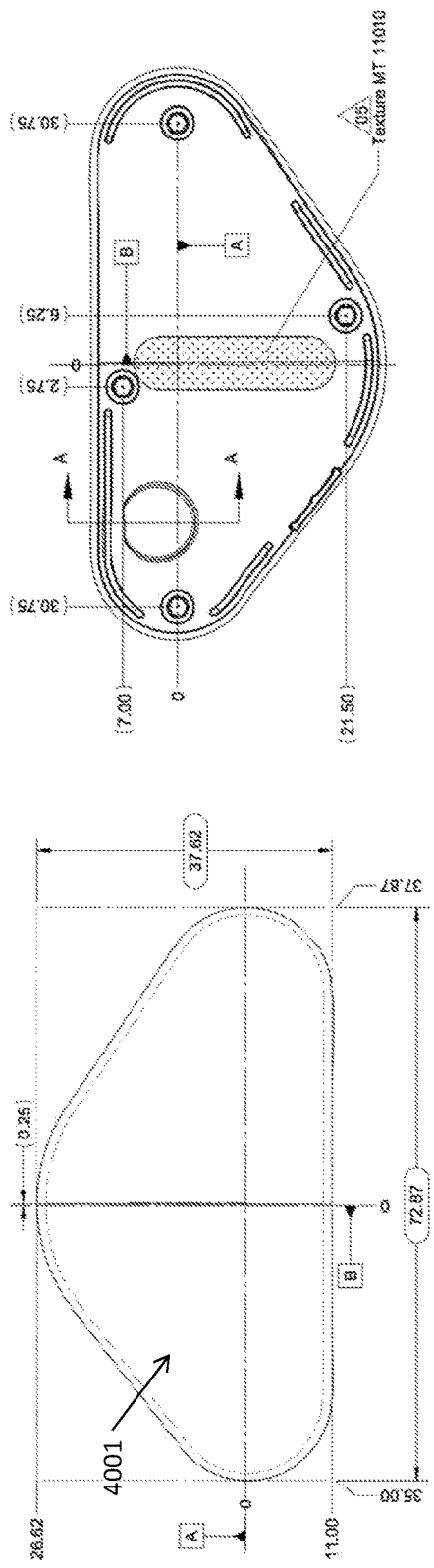
FIG. 40A
FIG. 40B
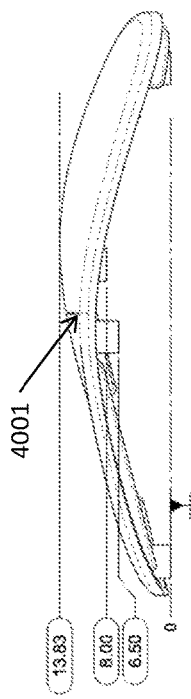
FIG. 40C
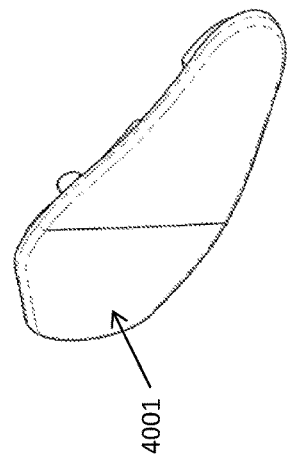
FIG. 40F
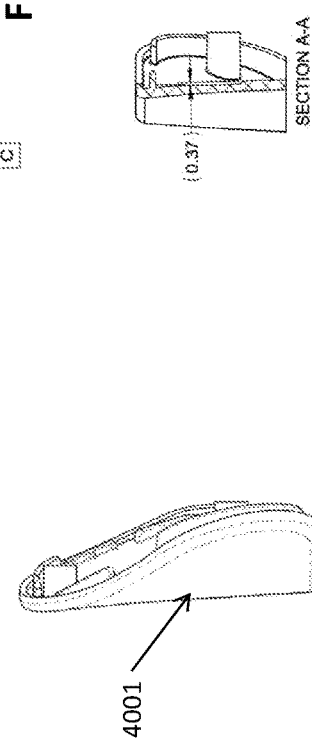
FIG. 40E
FIG. 40D

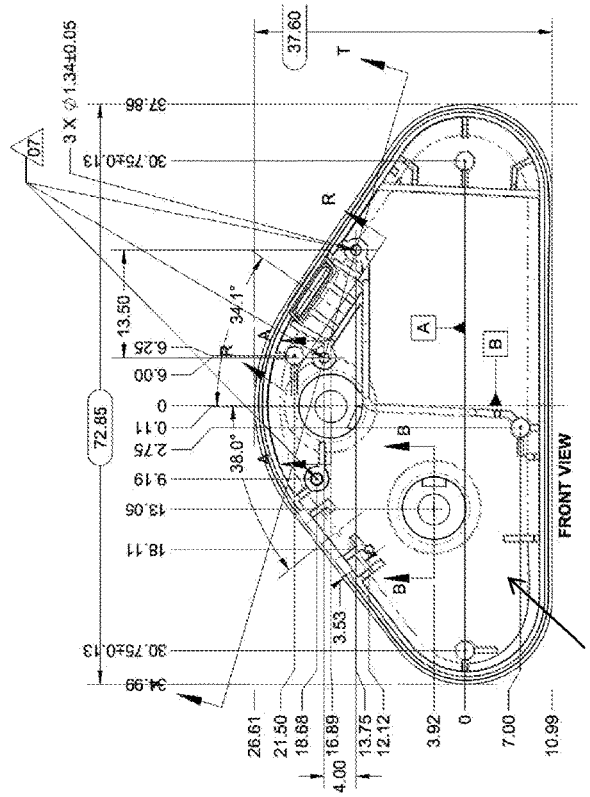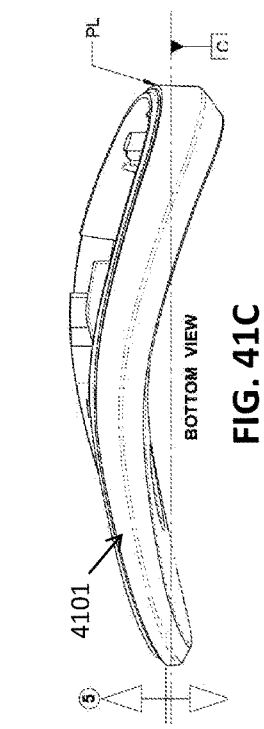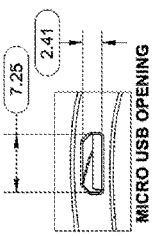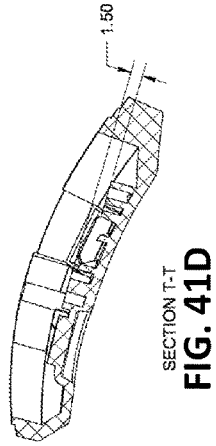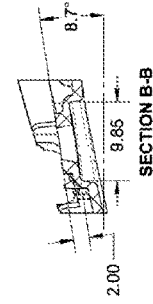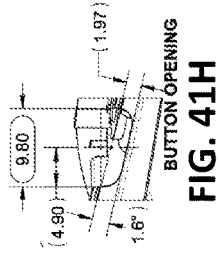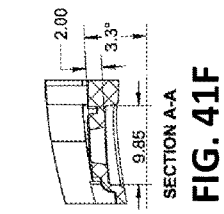

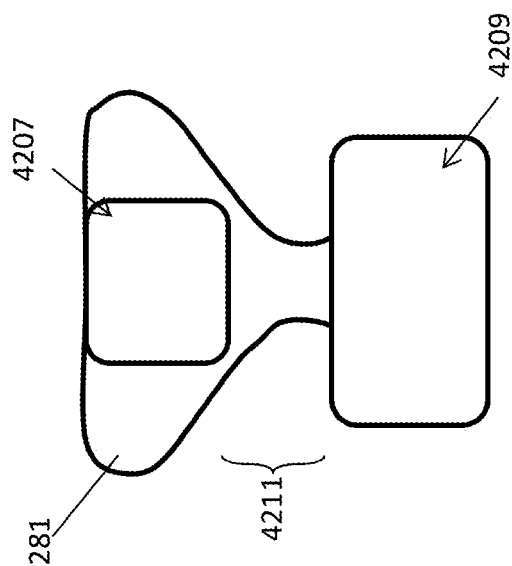
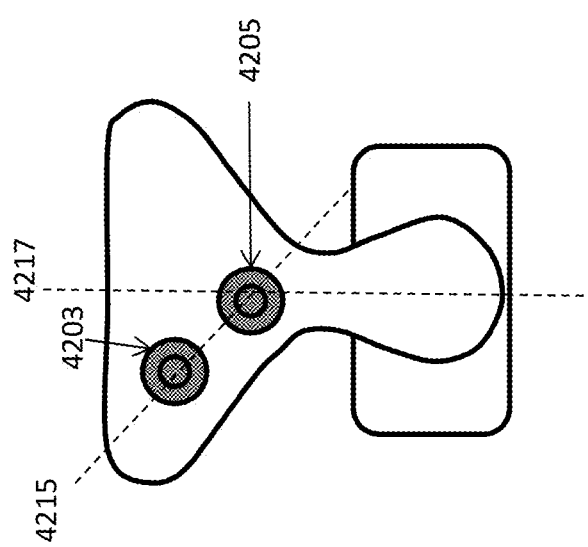
FIG. 42C
FIG. 42B
FIG. 42A

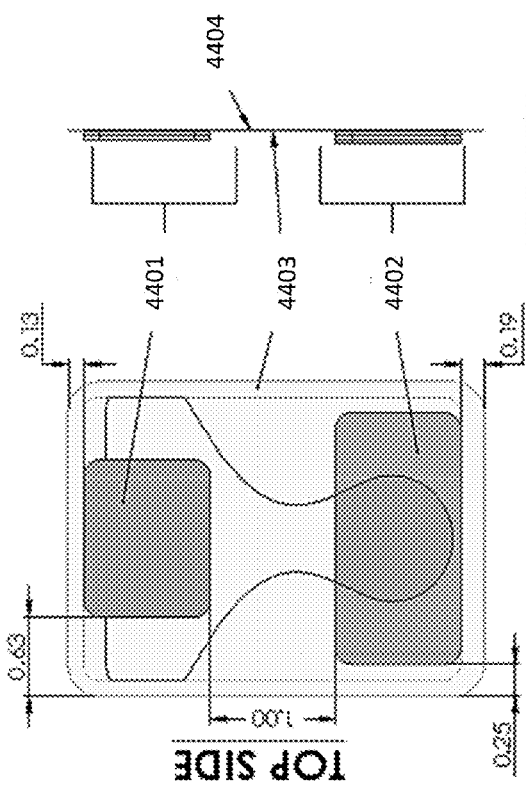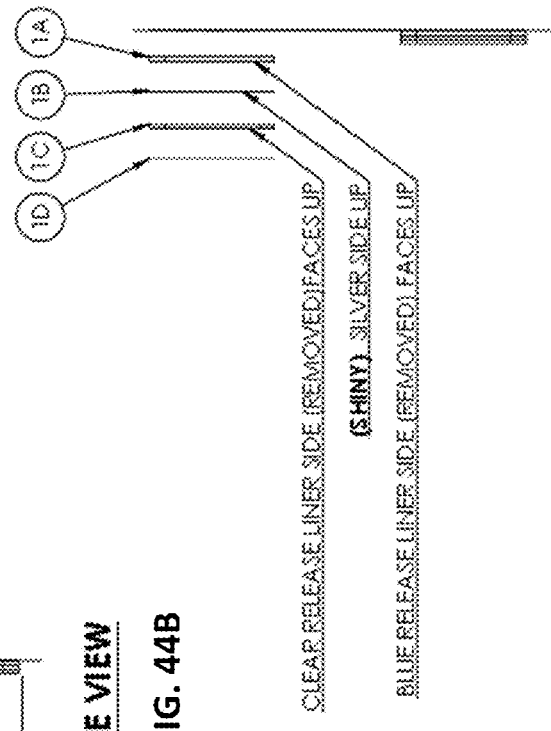
FIG. 44A / FIG. 44B / FIG. 44C / FIG. 44D

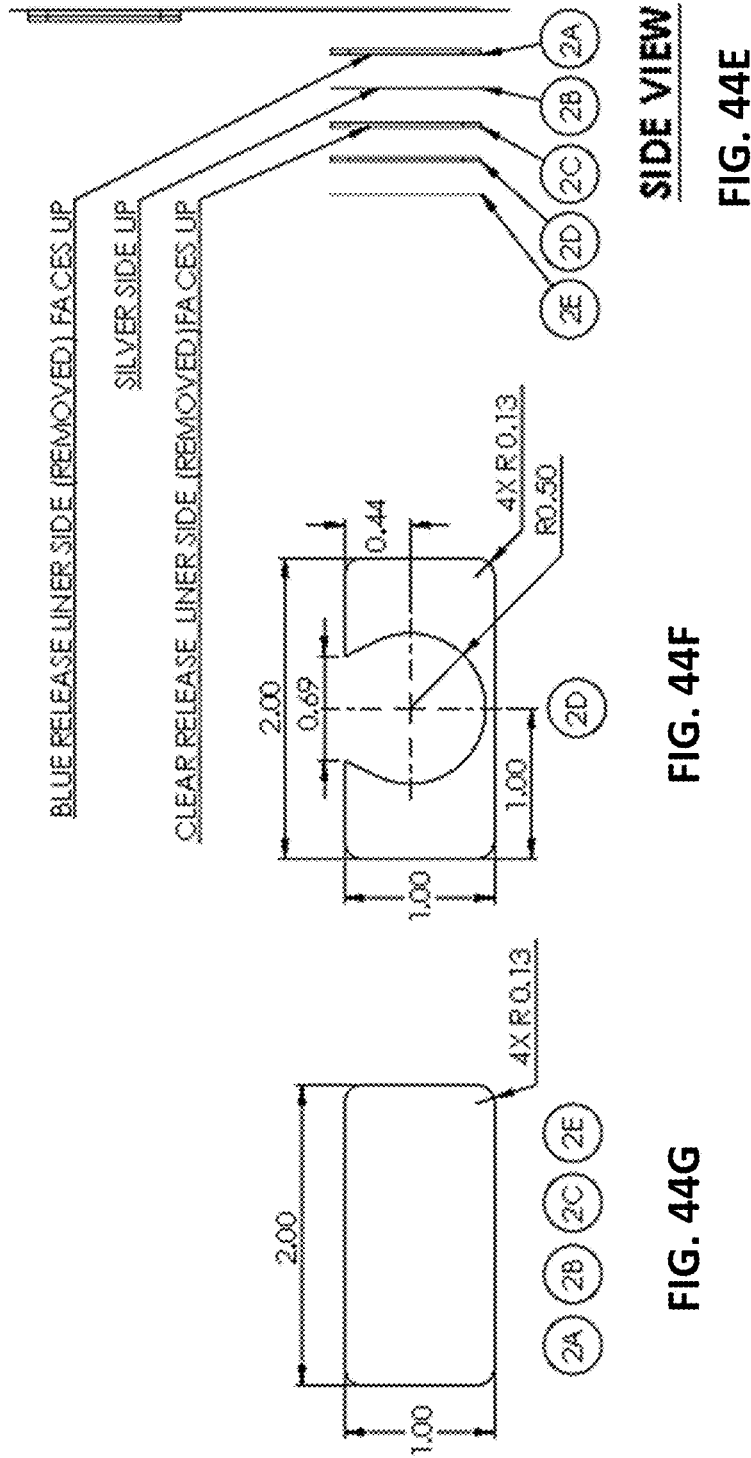

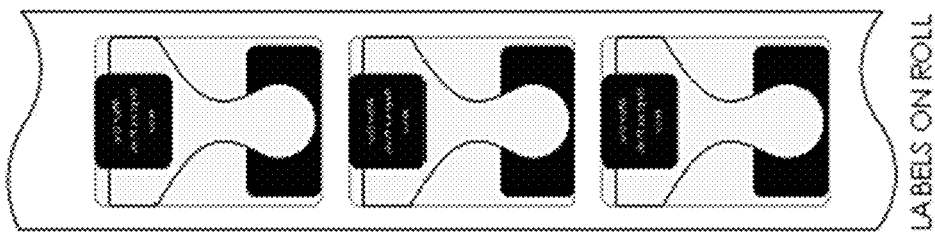
FIG. 45C
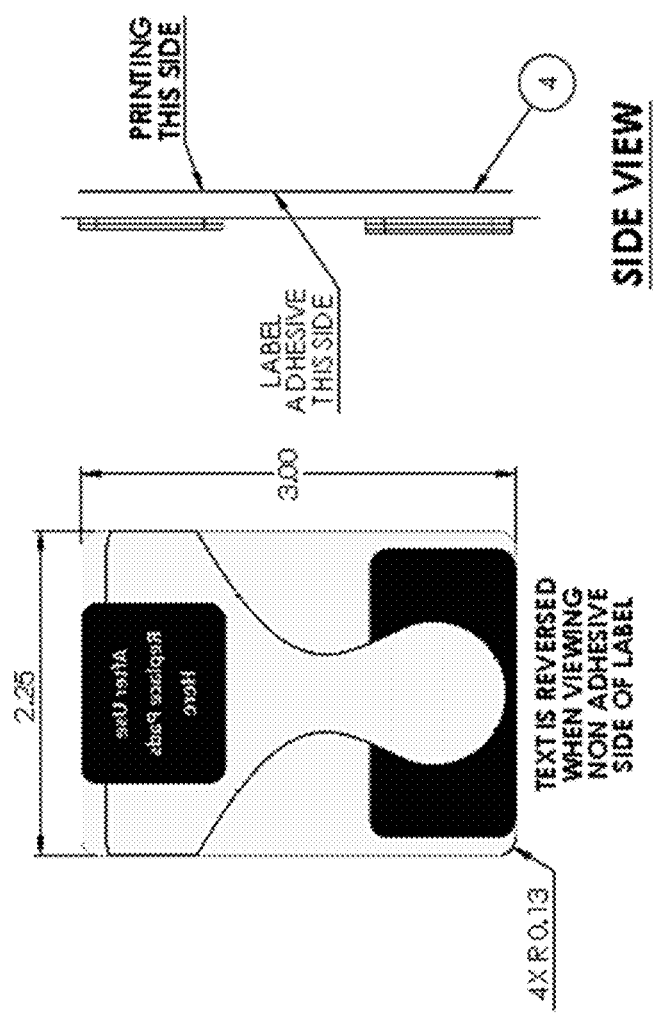
FIG. 45B
FIG. 45A

TRANSDERMAL ELECTRICAL STIMULATION AT THE NECK TO INDUCE NEUROMODULATION

CROSS REFERENCE TO RELATED APPLICATIONS

This patent application claims priority to U.S. provisional patent application No. 62/431,365, filed Dec. 7, 2016, titled "TRANSDERMAL ELECTRICAL STIMULATION AT THE NECK TO INDUCE NEUROMODULATION." This application is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are methods and apparatuses for noninvasive neuromodulation of a subject to induce relaxation, calm, mental clarity, and associated mental and physical states. These methods and devices in particular include a neck-worn apparatus which need only contact the user in a single location at the back of the users neck while coupled (e.g., magnetically) to controller and/or power source.

BACKGROUND

Noninvasive neuromodulation technologies that affect neuronal activity can modulate the pattern of neural activity and cause altered behavior, cognitive states, perception, and motor output without requiring an invasive procedure. For example, transcranial/transdermal electric stimulation (hereinafter "TES") through scalp electrodes has been used to affect brain function in humans in the form of transcranial alternating current stimulation (hereinafter "tACS"), transcranial direct current stimulation (hereinafter "tDCS"), cranial electrotherapy stimulation (hereinafter "CES"), and transcranial random noise stimulation (hereinafter "tRNS"). Systems and methods for TES have been disclosed (see for example, Capel U.S. Pat. No. 4,646,744; Haimovich et al. U.S. Pat. No. 5,540,736; Besio et al. U.S. Pat. No. 8,190,248; Hagedorn and Thompson U.S. Pat. No. 8,239,030; Bikson et al. U.S. Patent Publication 2011/0144716; and Lebedev et al. U.S. Patent Publication 2009/0177243). tDCS systems with numerous electrodes and a high level of configurability have been disclosed (see for example Bikson et al. U.S. Patent Publications 2012/0209346, 2012/0265261, and 2012/0245653), as have portable TES systems for auto-stimulation (Brocke U.S. Pat. No. 8,554,324). Other portable systems include U.S. patent application Ser. No. 14/639,015, titled "TRANSDERMAL ELECTRICAL STIMULATION DEVICES FOR MODIFYING OR INDUCING COGNITIVE STATE", filed Mar. 4, 2015, which is a continuation of U.S. patent application Ser. No. 14/320,461, titled "TRANSDERMAL ELECTRICAL STIMULATION DEVICES FOR MODIFYING OR INDUCING COGNITIVE STATE," filed on Jun. 30, 2014, now U.S. Pat. No. 9,002,458, and U.S. patent application Ser. No. 14/091,121, titled "WEARABLE TRANSDERMAL ELECTRICAL STIMULATION DEVICES AND METHODS OF USING THEM", filed on Nov. 26, 2013.

Typically, TES has been used therapeutically in various clinical applications, including treatment of pain, depression, epilepsy, and tinnitus. In at least some cases of TES therapeutic use, more data concerning the efficacy of TES in treatment is needed. Despite the research to date on TES neuromodulation, existing systems and methods for TES are lacking in at least some cases regarding the design and use of effective TES waveforms. Available systems are limited regarding the design and delivery of TES waveforms. Moreover, available systems do not permit the user to modulate a predetermined/preconfigured electrical stimulation protocol.

For example, U.S. Pat. No. 8,554,324 to Brocke discloses a mobile system for TES auto-stimulation by a user. Brocke further describes an embodiment wherein a wired or wireless remote control is used to control an electrical stimulation generator, as well as the use of smartphones, cellular telephones, or PDAs as a remote control. However, the systems and methods described by Brocke are lacking in at least some instances for defining, acquiring, and/or delivering effective TES waveforms to a user.

Unfortunately, the majority of the devices, including wearable devices, described to date must be positioned on one more likely two body locations, often including the face and head, which can be uncomfortable and visually unappealing to many consumers. Further, the stimulator electronics interfaces for such devices may be cumbersome, and the small size may limit the power and battery life. Even so-called self-contained devices may project from the body (including the face) making them uncomfortable, and may be easily disrupted.

In addition, the stimulation parameters (e.g., waveforms described to date have proven to be difficult to generalize across users; stimulation parameters that are effective for one set of users may be ineffective and/or uncomfortable (particularly when applied to the head and face) for other users.

Finally, most electrodes for TES (and TENS, transcutaneous electrical nerve stimulation) systems require single-use electrodes applied to the skin (or scalp) by an adhesive. Such electrodes may be reused for a limited number of uses, however they are difficult or impossible to clean, and may dry out, interfering with their ability to reliable make electrical contact with the skin.

It would be beneficial to provide apparatuses for effective neuromodulation (e.g., to affect mood and/or mental state) of a wide number of users that may be worn discretely and comfortably. In particular, such apparatuses (e.g., systems and devices) may also be easily operated and attached to the user, without disrupting the user's hair, skin, glasses, etc. It would also be beneficial to provide electrodes, and in particular electrodes for TES apparatuses, that may be re-used, cleaned and/or rewetted. Described herein are methods and apparatuses that may address these needs.

SUMMARY OF THE DISCLOSURE

In general, described herein are methods and apparatuses for the application of transdermal electrical stimulation (TES) in order to modulate a user's cognitive (e.g., mental) state, and in particular to induce a state of calm or relaxation. The apparatuses described herein may include a neck-applied electrode pad (also referred to herein as an electrode patch) that may automatically couple with a neck-worn TMS controller. The electrode patch may be worn (e.g., adhesively coupled) to the skin of a neck to make electrical contact with the midline of the back of user's neck. The electrode pad may include two or more electrodes for contacting the user's skin. A neck-worn controller (TES stimulator) may be configured as a cord, band, wire, torque (torc), necklace, loop, strap, or the like, and may be rigid or semi-rigid. The neck-worn controller may automatically self-couple (e.g., via a magnetic force coupler) to the electrode pad, and may be worn around the subject's neck, e.g., completely or partially around the subject's collar and/or shoulders. The controller (TES stimulator) may controllably apply one or more waveforms to the electrodes of the electrode pad to deliver TES. The waveforms applied are adapted to induce or enhance a cognitive state such as relaxation and/or calm.

Any of these TES apparatuses (devices and systems) described herein may include one or more re-usable electrodes, including cleanable (or self-cleaning), re-wettable (or self-re-wetting) electrodes. For example, a re-wettable electrode may include a "dry" electrode that is automatically wetted before use by applying a conductive material (conductive liquid, such as an aqueous solution, salt solution, conductive gel, etc.) by a vapor. In particular, an electrode may be integrated with a vaporizer (e.g., piezoelectric vaporizer, thermal vaporizer, etc.) that can saturate the electrode's skin-contacting region. The electrode's skin-contacting region may be a porous material (e.g., sponge, etc.). In some variations the apparatus may include a reservoir of the conducive material in contact with the vaporizer that may be used to automatically wet the skin-contacting region. In some variations the apparatus may configured to detect the wetness of the skin-contacting material and regulate the activity of the vaporizer based on feedback from the detected wetness (e.g., the detected resistance or conductivity of the skin-contacting region or the electrical contact with a skin surface). Any of the reusable (e.g., automatically re-wettable and/or self-cleaning) electrodes described herein may be used in whole or in part as part of a skin-contacting electrode, including as part of a physiological monitoring system (e.g., electrocardiogram, electroencephalogram, electromyogram, etc.). In particular, these devices may be part of a TES apparatus, as mentioned.

For example, described herein are neck-worn controller devices for applying transdermal electrical stimulation (TES) to the back of a subject's neck to modify a user's cognitive state and induce a relaxed state. These devices may include: a rigid or semi-rigid torc body configured to be worn around the user's neck; an electrode-coupling region at a middle region of torc body, wherein the electrode-coupling region comprises: a pair of electrode supports arranged adjacent to each other and separated by between 5 mm and 60 mm apart, and a skin-contacting electrode on each of the electrode supports configured to be secured against the user's neck when the torc body is placed around the users neck; and wherein the torc body encloses a control circuitry, a power source and a wireless communication circuitry. In any of the apparatuses described herein an electrode support may be an electrical contact (or may include an electrical contact) connecting a skin-contacting electrode to the control circuitry of the apparatus.

For example, a neck-worn controller device for applying transdermal electrical stimulation (TES) to the back of a subject's neck to modify a user's cognitive state and induce a relaxed state, may include: a rigid or semi-rigid torc body configured to be worn around the user's neck, the torc body extending in a U-shape from a first end to a second end; an electrode-coupling region near middle region of torc body between the first and second ends, wherein the electrode-coupling region comprises: a pair of electrode supports arranged adjacent to each other and separated by between 5 mm and 60 mm apart in a line that is at an angle (e.g., between 90° or perpendicular and 15 degrees) to an axis of the U-shaped torque body, and a skin-contacting reusable and rewettable electrode on each of the electrode supports configured to be secured against the user's neck when the torc body is placed around the users neck; and wherein the torc body encloses a control circuitry, a power source and a wireless communication circuitry.

In general, the spacing between the electrodes (or electrical contacts) connecting to the electrodes (as well as the relative arrangement of the electrodes on the user's neck) in order to evoke a relaxed state may be important, and is typically between 5 mm and 80 mm apart (e.g., 5 mm and 70 mm, 5 mm and 60 mm, 5 mm and 50 mm, 5 mm and 40 mm, 5 mm and 30 mm, 5 mm and 20 mm, 10 mm and 70 mm, 10 mm and 60 mm, 10 mm and 50 mm, 10 mm and 40 mm, etc.). This spacing may be edge-to-edge (nearest edge to nearest edge) or center-to-center between the two electrode contacts and/or electrodes.

Any of these apparatuses may include a control (e.g., on/off, rest, start/stop, rewet, etc.) on the torc body; the control may be electrically connected to the control circuitry and may be any appropriate control, including but not limited to a button, dial, touchpad, slider, etc.

As mentioned, the skin-contacting electrode on each of the electrode supports may comprise a re-wettable electrode, including self-re-wetting electrodes and/or automatically re-wetting electrodes, self-cleaning electrodes, or the like. For example, the skin-contacting electrode on each of the electrode supports may include a mist generator (e.g., vaporizer), and may be coupled to a fluid reservoir on the torc body. The mist generator may be configured to wet one or both of the skin-contacting electrodes. For example a mist generator comprises a piezo driver configured to generate a mist. In some variations the mist generator may be a piezo that is configured to be driven by the same circuitry driving the electrical stimulation (e.g., TES), e.g., at a frequency between 100 KHz to 2 MHz (or greater).

The body (torc body) may be partial rigid, including having one or more rigid portions connected by a flexible region or regions. The torc body may be flexible. The torc body may be any appropriate shape, including U-shaped or C-shaped. The torc body may include a charging port for charging a battery within the torc body. The torc body may be an elongate body that generally extends from a first end to a second end, and fits over the user's neck while holding the electrodes to the back of the user's neck. The torc body may include a hinge on the torc body. The electrode-coupling region may be rigid. The control circuitry, the power source and the wireless communication circuitry may be located at an end of the elongate body. The control circuitry and wireless communication circuitry may be located at a first end region of the elongate body and the power source may be located at a second end region of the elongate body.

As will be described in more detail below, any of the skin-contacting electrodes described herein may be fixed to the neck-worn TES apparatus or may be removably coupled to the neck-worn TES apparatus (e.g., to the electrode supports). For example, the electrodes may be removable and replaceable. The electrode-coupling region may comprise a pair of magnetic attachments. Alternatively or additionally, the skin-contacting electrodes may self-adhere to the TES apparatus allowing for electrical and physical connection via an adhesive, mechanical (e.g., hook-and-loop fasteners, artificial setae, etc.), etc.

Any of the neck-worn TES apparatuses described herein may include one or more speakers and/or an audio connector (jack) for coupling to a speaker or headphones.

In general, any of the neck-worn TES apparatuses may include control circuitry for driving TES through the electrodes and/or regulating the apparatus (including the wetting of the electrodes in some variations). For example, the control circuitry may be configured to deliver electrical energy between the pair of electrodes (or electrical contacts), wherein the electrical energy comprises a carrier wave having a frequency that is greater than 250 Hz that is amplitude modulated at a frequency that is ten percent or less the frequency of the carrier wave, further wherein the amplitude modulation is varied at least once every 40 seconds.

Any of the apparatuses and method described herein may be used (and may be further configured for use) to enhance relaxation. Alternatively or additionally, these apparatuses and methods may be used to lower stress. Stress may be monitored (and in some variations used as feedback, including visual or audio feedback, such as displaying an indicator of the user's stress level (blood pressure, heart rate, skin conductance, etc.) and/or providing controlling feedback (increasing or decreasing stimulation, modulating a stimulation parameter, etc.). Thus, an indicator of stress (or mood) may be used as a control input for controlling/adjusting stimulation including turning on/off, adjusting a parameter of electrical stimulation (frequency, current, duty cycle, peak amplitude, rise time, duration, etc.). Alternatively or additionally, any of the apparatuses and methods described herein may be used to elevate mood. Thus, in general, any of the apparatuses and methods described herein may be useful to reduce stress, reduce anxiety, improve sleep, and/or improve mood.

For example, any of the apparatuses and methods described herein may be used to improve sleep (e.g., one or more of: sleep quality, sleep onset, sleep duration, sleep depth/stage, etc.). An indicator of sleep (e.g., sleep stage/ sleep level) may be used as a control input for controlling/ adjusting stimulation including turning on/off, adjusting a parameter of electrical stimulation (frequency, current, duty cycle, peak amplitude, rise time, duration, etc.).

The methods described herein may be used to apply neurostimulation to one or more nerves (e.g., nerve bundles) though the skin of the subject's neck at two nearby (e.g., adjacent) locations near the cervical spinal region, such as beneath the hairline but above the C7 cervical region. The two locations may be separated by between about 0.5 and 2.5 inches apart from each other. A single electrode pad may be used to make contact with both sites.

The TES waveforms used to apply energy herein may include a carrier frequency that is between 250 Hz and 50 kHz, and may typically an amplitude between about 1-40 mA (e.g., peak amplitude of between 10 mA and 35 mA, between 10 mA and 30 mA, etc.). The carrier waves may be asymmetric and/or biphasic. Significantly, the applied TES waveforms are modulated by an amplitude modulation envelope that comprises a lower frequency that is at least 10× lower than the frequency of the carrier wave (e.g., a modulation envelope between 10-1 kHz, e.g., between 10-900 Hz, between 10-850 Hz, between 10-800 Hz, etc., and a carrier wave of greater than 2250 Hz, e.g., greater than 300 Hz, 350 Hz, 400 Hz, 450 Hz, 500 Hz, 550 Hz, 600 Hz, 650 Hz, 700 Hz, 750 Hz, 800 Hz, 850 Hz, 900 Hz, 950 Hz, 1 kHz, 2 kHz, 3 kHz, 4 kHz, 5 kHz, 6 kHz, etc., and particularly greater than 5 kHz). The applied waveform may be varied every 5 to 60 seconds, typically by varying the amplitude modulation, alternatively, the waveform may be held for longer durations (e.g., 1 minute to 5 minutes, 1 minute to 10 minutes, 1 minute to 20 minutes, 1 minute to 30 minutes, 1 minute to 40 minutes, etc.). For example, the shape of the amplitude modulation envelope may be changed (e.g., from a sinusoidal envelope to a rectangular envelope, a saw tooth envelope, a triangular envelope, a stair-case envelope, etc.), and the frequency of the amplitude modulation may change separately or at the same time. In some variations the shape of the amplitude modulation envelope is changed by adjusting one or more of: 1) the symmetry ratio (meaning the wave form in time may be non-symmetrical in the time axis; the ratio is an estimate of how non-symmetrical it is), or 2) the flat ratio (meaning the portion(s) of the waveform that remains unchanged in amplitude over as a portion of the wave period), etc. In any of the method and apparatuses (configured to perform these methods) described herein, the waveforms duration may be controlled by the subject; thus subject may continue to apply the waveform until an effect is achieved. For example, a waveform may be applied in a loop that is repeated until terminated by the subject.

In some variations, the rise time of the waveform(s) applied may be controlled to minimize discomfort. For example, the rise-time of a basic pulse waveform applied may be between 1 and 20 microsecond. The rise-time of the pulse may affect both comfort and efficacy; based on preliminary data, it may be beneficial to vary the rise time between 1-20 μs, including varying the rise time continuously between 1 and 20 μs, or picking a rise time that is between 1 and 20 μs and using this, and/or allowing the device and/or use to adjust the rise time (e.g., between 1-20 μs) during application of the waveforms.

As mentioned, the apparatuses described herein include neck-worn controller devices for applying transdermal electrical stimulation (TES) to the back of a subject's neck to modify a user's cognitive state and induce a relaxed state. For example, described herein are neck-worn (also referred to herein as "neck wearable") that may be comfortably worn around the user's neck and may include: an elongate body configured to be worn at least partially around the user's neck; an electrode-coupling region on the elongate body, the electrode-coupling region comprising: a pair of electrical contacts, and at least one self-connecting (e.g., magnetic, adhesive, etc.) attachment configured to automatically couple the electrical contacts with a complimentary electrical contact on an electrode pad worn on the user's neck when the magnetic attachment is placed adjacent to the electrode pad; and wherein the elongate body encloses a control circuitry, a power source such as a battery, a high voltage source of power for neural stimulation greater than 20 volts, and a wireless communication circuitry.

Any of the neck-worn controller devices may include one or more controls on the body of the device. For example, a neck-worn controller may include a switch, dial, button, slider, etc. The controller may control one or more of (and/or multiple controls may control): power (e.g., on/off/standby), intensity of the TES being applied, communication with a remote (e.g., wireless) controller, playing of the TES (e.g., TES start/pause/stop), selection of a TES waveform, etc.

Any of the neck-worn controller devices described herein may include one or more output such as a display (e.g., LCD, LED, etc.) or other visual output (LED), a tactile output (haptic, e.g., vibrational output, etc.).

The elongate body may be stiff, flexible, or semi-stiff, and may include both stiff and flexible regions (e.g., stiff regions connected by flexible regions). For example, the elongate body may be flexible so that it generally retains its shape but can be "opened" (e.g., when the device is U- or C-shaped) to fit over a user's neck. In general, the elongate body may be U-shaped or C-shaped. In some variations the elongate body include a hinge or hinges that may be used to open the elongate body for placing it on/taking it off of the user's neck.

Any of the apparatuses described herein may include a charging port on the elongate body (e.g., micro USB port). Alternatively or additionally any of these apparatuses may include a non-contact charger (e.g., inductive charging, etc.) or the like.

As mentioned, in general, any of the neck-worn controller devices described herein may include an electrode-coupling region that may be used to secure the neck-worn controller to the user via a connection to an electrode pad that can be separately worn on the user's neck. For example, an electrode-coupling region may be located in a middle region of the elongate body. The electrode-coupling region may generally be rigid or stiff so that it does not shift during wearing or dislodge the coupling attachments (e.g., attachment between the electrical contact and a connector on an electrode pad. Either the connector on the electrode pad or the electrical contact on the neck-worn controller, or both, may include a magnet and/or a magnetic material (that may be attracted to a magnet, such as steel, etc.). This may allow self-connection between the two. The magnetic material, when included, may be any appropriate magnetic material, including "static" magnetic material (e.g., ferrous or magnetic material) and/or electromagnetic materials.

In some variations the electrode-coupling region is at an end of the elongate body.

In general, any of the apparatuses described herein may include a self-connecting or self-engaging connector drawing together the electrode pad and the neck-worn apparatus so that an electrical and/or mechanical connection is made between the two. Although the primary self-engaging connectors described herein are magnetic connectors, any appropriate connector may be used, including adhesive, and/or mechanical self-attaching couplings. However in some variations the electrode-coupling region may comprise a pair of magnetic attachments.

The electrical contact may be integrally formed with the magnetic attachment. For example, the electrical contact may be made through a magnetic (including ferrous) material. In some variations the connector and/or the electrical contacts may be made of an electrically conductive material forming the electrical pathway surround by or adjacent to a magnetic connector (e.g., the electrical contact may be adjacent to or surrounded by the magnetic attachment). One or more self-connecting connectors (magnets) may be included.

In any of these variations, the power source and the wireless communication circuitry are located at an end of the elongate body. For example, the control circuitry and wireless communication circuitry may be located at a first end region of the elongate body and the power source may be located at a second end region of the elongate body. In general, when the neck-worn controller device is configured to be worn around both sides of a user's neck (e.g., is U-shaped), then the two ends (arms) of the U-shaped body may be balanced in shape, size and/or weight.

The electrical contacts may be further adapted to connect to a properly oriented and configured electrode pad to achieve the desired relaxation effect by transdermal electrical stimulation of the neck (e.g., and in some variations just at the neck). In particular, the pair of electrical contacts may be separated by between 1.2 inches and 0.7 inches along the length of the elongate body. This separation may allow them to properly and automatically engage (e.g., self-engage) with the electrode pads described herein for TES of the neck to induce relaxation.

Any of the neck-worn devices described herein may be configured to include one or more speakers (e.g., headphones, etc.). In some variations the apparatuses described herein may be configured to include one or more ear-based electrodes.

In general, the control circuitry may be configured to deliver electrical energy (e.g., TES) between the pair of electrical contacts in order to evoke relaxation in a user by applying TES at the midline of the user's neck between the C1 and T2 region (e.g., C3 and T1, C3 and T2, etc.). For example the control circuitry may be configured to deliver electrical energy comprising a carrier wave having a frequency that is greater than 250 Hz that is amplitude modulated at a frequency that is ten percent or less the frequency of the carrier wave, further wherein the amplitude modulation is varied at least once every 60 seconds (e.g., once every: 50 sec, 45 sec, 40 sec, 35 sec, 30 sec, etc.).

In any of the apparatuses (e.g., systems) described herein, software, firmware, or hardware may be separate from the neck-worn device and may wirelessly connect with the device to regulate, control, select, and/or modify the TES waveforms applied by the apparatus. For example, a user electronics device (e.g., a handheld user electronics device such as a smartphone, wearable electronics, etc.) may wirelessly communicate with the neck-worn controller to transmit or deliver the TES waveform and/or to modify the TES waveform (e.g., increase/decrease intensity, etc.) and/or start/stop/pause operation of the TES waveform delivery.

A neck-worn controller device for applying transdermal electrical stimulation (TES) to the back of a subject's neck to modify a user's cognitive state and induce a relaxed state may include: an elongate body configured to be worn around the user's neck; a rigid electrode-coupling region on the elongate body, the electrode-coupling region comprising: a pair of electrical contacts adjacent to each other, and at least one magnetic attachment configured to automatically couple the electrical contacts with a complimentary electrical contact on an electrode pad worn on the user's neck when the magnetic attachment is placed adjacent to the electrode pad; and control circuitry, a power source and a wireless communication circuitry.

Also described herein are systems for applying transdermal electrical stimulation (TES) to the back of a subject's neck to modify a user's cognitive state and induce a relaxed state, that include an electrode pad to be worn on the back of the neck and a neck-worn controller (and in some variations control software that operates on a controller of a user electronic device and wirelessly communicates with the neck-worn controller).

For example, a system for applying transdermal electrical stimulation (TES) to the back of a subject's neck to modify a user's cognitive state and induce a relaxed state may include: an adhesive electrode pad comprising a first electrode and second electrode on a first side, and a first connector electrically connected to the first electrode and a second connector electrically connected to the second electrode, wherein the first and second connectors are on a second side opposite from the first side; and a neck-worn controller device, the neck-worn controller comprising: an elongate body configured to be worn on a user's neck, an electrode-coupling region on the elongate body having at least one magnetic attachment configured to automatically couple the first connector on the electrode pad to the a first electrical contact on the neck-worn controller device when the magnetic attachment is placed adjacent to the electrode pad, and a control circuitry, a power source and wireless communication circuitry.

The first electrode and the second electrode may be arranged in a line that on the first side that is at angle (e.g. between 90° or perpendicular and 15 degrees, e.g. between 30 degrees and 60 degrees, etc.) to a line connecting the first connector and the second connector electrically connected on the second side.

The adhesive electrode pad(s) may be configured to be worn on the back of a subject's neck so that the first electrode and the second electrode are arranged along a midline of the back of the user's neck. In any of the apparatuses and methods described herein, the pads may be adhered to the neck-worn body before it is placed around the user's neck. Thus, the device may be used to place the pads onto the skin for the user.

In some variations, the applicants have found that it is particularly advantageous when applying TES energy to the back of the user's neck to induce relaxation, to have one of the electrodes (e.g., the second electrode) be larger than the other electrode. For example, a surface area of one of the electrodes may be greater than 1.25 times the surface are of the other electrode (e.g., greater than 1.4×, greater than 1.5×, greater than 1.6×, greater than 1.7×, greater than 1.8×, greater than 1.9×, greater than 2×, etc.).

In general, the neck-worn controller used as part of any of the systems described herein may be any of the neck-worn controllers described above.

For example, a system for applying transdermal electrical stimulation (TES) to the back of a subject's neck to modify a user's cognitive state and induce a relaxed state may include: an adhesive electrode pad comprising a first electrode and second electrode arranged in a vertical line on a first side, and a first connector electrically connected to the first electrode and a second connector electrically connected to the second electrode, wherein the first and second connectors are arranged in a horizontal line perpendicular to the vertical line on a second side that is opposite from the first side; and a neck-worn controller device, the neck-worn controller comprising: an elongate body configured to be worn on a user's neck, an electrode-coupling region on the elongate body having a magnetic attachment configured to automatically electrically and mechanically couple a pair of electrical contacts on the electrode-coupling region with the first and second connectors on the electrode pad when the magnetic attachment is within less than 1 inch from the electrode pad, a control circuitry, a power source, and a wireless communication circuitry.

Also described herein are methods of applying transdermal electrical stimulation (TES) to the back of a user's neck to modify a user's cognitive state and induce a relaxed state. In general such a method may include: attaching a first electrode and second electrode to a back of the user's neck between the user's hairline and the user's C7 cervical region; applying electrical energy between the first electrode and the second electrode to deliver TES; and inducing, in the user, a relaxed mental by the application of TES.

Attaching may comprise adhesively attaching an electrode pad comprising the first and second electrode to the back of a user's neck so that the first and second electrodes are arranged along the midline of the user's neck.

Any of these methods may also include placing a neck-worn controller around the neck of the user and allowing the neck-worn controller to self-engage (including magnetically, mechanically, chemically (e.g., adhesively), etc.) with the electrode pad to form an electrical contact between the neck-worn controller and the first electrode and second electrode.

Applying electrical energy may comprise applying TES by delivering electrical energy between the first electrode and the second electrode, wherein the electrical energy comprises a carrier wave having a frequency that is greater than 250 Hz that is amplitude modulated at a frequency that is ten percent or less the frequency of the carrier wave, further wherein the amplitude modulation is varied at least once every 60 seconds (e.g., once every 55 sec, once every 50 sec, once every 45 sec, once every 40 sec., once every 35 seconds, once every 30 seconds, etc.).

In general, the amplitude modulation may be varied in any appropriate manner, including by varying the shape of an envelope of the amplitude modulation. For example, the envelope shape may be changed between two or more of: a square wave, a step-function, a saw tooth, a triangular shape, a sinusoid, etc. The amplitude modulation may be varied by varying one or both of a symmetry ratio and a flat ratio of the amplitude modulation.

Applying TES to induce relaxation may include applying electrical energy for any appropriate length of time (e.g., for 2 min or greater, 5 minutes or greater, 10 minutes or greater, 15 minutes or greater, etc.).

In general, applying may comprise delivering TES to a nerve fiber, nerve or nerve bundle extending through the user's neck, including spinal nerve, cranial nerves, etc.

For example, a method of applying transdermal electrical stimulation (TES) to the back of a user's neck to modify a user's cognitive state and induce a relaxed state may include: attaching a first electrode and second electrode to a midline of a back of the user's neck between the user's hairline and the user's C7 cervical region, wherein the first and second electrode form part of an electrode pad; placing a neck-worn controller over at least one of the user's shoulders and allowing the neck-worn controller to magnetically self-engage with the electrode pad to form an electrical contact between the neck-worn controller and the first electrode and second electrode; applying TES by delivering electrical energy between the first electrode and the second electrode, wherein the electrical energy comprises a carrier wave having a frequency that is greater than 250 Hz that is amplitude modulated at a frequency that is ten percent or less the frequency of the carrier wave, further wherein the amplitude modulation is varied at least once every 60 (e.g., 55 sec, 50 sec, 45 sec, 40 sec, 35 sec, 30 sec, etc.); and inducing, in the user, a relaxed mental by the application of TES.

In general, any of the methods and apparatuses described herein for self-engaging or attaching the electrode and the device may be configured to mechanically (e.g., loop-and-hook, artificial setae, etc.), chemically (e.g., adhesive), magnetically, or otherwise (including combinations of these) attach. Alternatively, in some variations the apparatuses and methods described herein are configured with the electrode affixed or attached (including integrally attached) to the rest of the apparatus including the electrical contact (or electrical support).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A is a schematic of a front (user-facing) side of an electrode pad (e.g. patch) or electrical contact that may be applied to a user's skin or neck. The electrode patch may be adhesive, and may include one or more (e.g. a pair of) electrodes for making electrical contact with the user's skin. The electrodes may be covered in a gel or other material to enhance electrical contact. The electrode patch may include an adhesive (e.g., skin adhesive) for securing the electrode patch to the skin of the user's neck. In any of these variations, the electrodes may include a single substrate or a plurality of substrates comprising multiple electrode/skin contact points.

FIG. 1B is a schematic of the back of an electrode patch such as the one shown in FIG. 1A. In this example, a pair of self-connecting connectors is included, which may make a secure electrical connection to the neck-worn controller (TES controller/stimulator). The self-connecting connector in this example is a magnetic connector. Alternatively or additionally, the contact between the patch or patches and the device may be self-adhesive via conductive gel contact.

FIG. 1C is an example of a neck-worn controller (TES controller/stimulator) that may couple to the electrical contact with one or more self-connecting connectors magnetic connectors. In general the neck-worn controller may include electronics (controller, processor, etc.) for applying TES to the electrodes of the electrode patch, a power supply providing power to the electronics, charging circuitry for the battery (e.g., inductive charging, plug-in charging, etc.), and communications circuitry for communicating with one or more remote processors that may be used to control/regulate the application of TES by the device. The neck-worn controller may also include one or more controls for regulating the operation of the system (e.g., on/off, intensity up/down, etc.).

FIG. 1D schematically illustrates a user electronics device, such as a hand-held device having a processor that may be wirelessly (or via a wired connection) coupled to neck-worn controller. The user electronics device may include software, hardware, or firmware for operating the system.

FIGS. 2A-2D illustrate variations of electrode patches that may be used in any of the systems and methods described herein. FIGS. 2A-2D all show the skin-facing, front, side of the electrode patch, and include at least two electrodes.

FIGS. 3A-3D illustrate variations of electrode patches that may be used in any of the systems and methods described herein. FIGS. 3A-3D illustrate the back side of the electrode patch, which may self-connect or couple with the neck-worn controller.

FIGS. 4A and 4B schematically illustrate examples of neck-worn controllers. FIG. 4A shows a neck-worn controller that is worn on just one side of the user's neck (asymmetrically), coupling at one end region to the electrode patch. FIG. 4B shows a neck-worn controller that is worn on either side of the user's neck (symmetrically) coupling in a middle region to an electrode patch.

In FIG. 6 the neck-worn controller include both flexible regions and rigid regions; the region coupling to the electrode patch is rigid.

In FIG. 7A the user has already applied the electrode patch to the back of the neck so that a pair of self-connecting connectors on the back of the electrode patch are oriented horizontally, and the neck-worn controller is placed around the neck allowing one of the self-connecting connectors to automatically align and connect with the first connector on the neck-worn controller. In FIG. 7B the second self-connecting connectors connects to the second connector. Additionally, the patch or patches may be placed first onto the device and then the device/patch combination is placed together onto the back of the neck, allowing the device to place the patch or patches.

FIG. 16A shows a back view perspective and FIG. 16B shows a front perspective view.

FIG. 17A is a back perspective view, FIG. 17B is a front perspective view and FIG. 17C is a top perspective view.

FIG. 18A is a back perspective view, FIG. 18B is a front perspective view and FIG. 18C is a top perspective view.

In FIG. 19, the system includes a neck-worn controller, an electrode patch and control software running on a user's hand-held electronic device (shown in this example as a smartphone).

FIGS. 21A and 21B generally illustrate the variable amplitude modulation of a carrier wave to induce a calm or relaxed mental state when applied at the user's neck region as described herein.

FIG. 23 illustrates one example of a TES waveform showing changes in the carrier wave (frequency, peak current, % duty cycle, % DC) and changes in the amplitude modulation (AM duty cycle, AM frequency, AM flat ratio (%), AM symmetry ratio (%), and AM DC offset (%)). This waveform is an example of a relaxation-inducing waveform as described herein.

FIG. 24A is a back view; FIG. 24B shows an enlarged front view of the electrode attachment sites; FIG. 24C is a front view; and FIG. 24D is a side perspective view.

FIG. 25A is a front perspective view, and FIG. 25B is a back view.

FIG. 26A shows a back perspective view; FIG. 26B shows a top view, FIG. 26C is a back view, and FIG. 26D is another back perspective view.

FIGS. 27A-27C illustrate an example of a neck-worn TES controller/stimulator having integrated electrodes that may be configured as self-cleaning and self-rewetting electrodes. FIG. 27A is a front perspective view and FIG. 27B is a back perspective view of the apparatus. FIG. 27C is a top perspective view with the reusable/rewettable and/or self-cleaning electrodes in a closed configuration.

FIG. 30A is a top perspective view with the storage/recharging chamber opened; and FIGS. 30B-30C are alternative top perspective views with the storage/recharging chamber closed.

FIGS. 33A and 33B show back and front perspective views, respectively, of the storage/recharging chamber configured as a stand with the chamber opened and the neck-worn TES controller/stimulator held therein.

FIG. 34A is a back perspective view and FIG. 34B is a front perspective view.

FIG. 36A shows a right side view, FIG. 36B shows a front perspective view, FIG. 36C shows a back perspective view, and FIG. 36D shows a back view.

FIG. 37A-37C illustrate locations for electrode placement of a neck-work TES controller/stimulator as described herein. The electrodes may be separated by an approximately 1 inch minimum distance and arranged in an anterior to posterior (e.g. foot to head) longitudinal direction, so that the electrodes are stacked atop each other relative in the longitudinal axis. For example, in FIG. 37A, the first (upper) electrode is on the skin over the C1 to C6 regions of the spine, and the second (lower) electrode is over the C2 to C7 region of the spine. In FIG. 37B the first (upper) electrode is in the cervical region of the spine, while the second (lower) electrode is over the thoracic region (e.g., T1 or T2 region) of the spine. In FIG. 37C the distance between the upper and lower electrodes has been increased, but the first (upper) electrode is still in the cervical region while the second (lower) electrode is over the thoracic region.

FIG. 38A shows an example of an adhesive electrode pad configured to be worn over the cervical and thoracic region (similar to that shown in FIG. 37B) having a pair of snaps to which a TES controller/stimulator may be coupled. The adhesive electrode pad may be configured as an adapter to adapt a forehead/temple TES controller/stimulator apparatus for use on the neck as described herein.

FIG. 38B shows adhesive electrode (adapter) of FIG. 38A with a TES controller/stimulator coupled thereto.

FIGS. 40A-40F illustrate an example of a top cover portion of a controller/stimulator TES apparatus such as the one shown in FIGS. 39A-39B. FIG. 40A is a front view. FIG. 40B is a back view, showing the inside region of the top cover. FIG. 40C is a bottom side view along a long side of the device. FIG. 40D is a second side view. FIG. 40E is a view through a partial section taken through line A-A of FIG. 40B. FIG. 40F is a front perspective view. Note that the dimensions shown, as for all dimensions shown throughout, are exemplary (unless otherwise indicated), and may be approximate. These dimensions are shown in millimeters (mm).

FIG. 41A-41I illustrate an example of a bottom cover portion of the controller/stimulator TES apparatus such as the one shown in FIGS. 39A-39B. FIG. 41A is a front view, showing the internal region of the bottom cover. FIG. 41B is a back view, showing the outer surface. FIG. 41C is a bottom side view. FIG. 41D is a sectional view through line T-T in FIG. 41A. FIG. 41E is an enlarged view of the port (e.g., micro USB port) opening visible in FIG. 41B. FIG.

41F is a sectional view through line A-A in FIG. 41A. FIG. 41G is a sectional view through line R-R in FIG. 41A. FIG. 41H shows an enlarged view of the button region of the apparatus. FIG. 41I shows a sectional view through line B-B in FIG. 41A. As mentioned above, the dimensions shown are in mm and are exemplary and may be approximate, unless otherwise indicated.

FIGS. 42A-42C show front, back and side views, respectively, of an example of an adapter (neck-only) electrode pad.

In FIG. 43A a view of the bottom (skin-contacting side) is shown. FIG. 43D shows the carbon back layer; FIG. 43E shows a bottom view of the dielectric layer; and FIG. 43F shows a top view of the dielectric layer.

FIGS. 44A-44B show front and side views, respectively, of an adapter electrode pad having a connector and coupling region such as is shown in FIGS. 43A-43F, above, also including the electrode pads for the first (upper) and second (lower) electrode. FIG. 44C shows an exploded view of the first (upper) connector pad portion. FIG. 44D shows the potential dimensions of the first (upper) connector pad portion. FIG. 44E shows an exploded view of the second (lower) electrode pad portion. FIG. 44F is an example of the foam portion of the second (lower) electrode pad. FIG. 44G illustrates potential dimensions for other layers of the apparatus that may be included as part of the neck-worn apparatus. The dimensions shown in these figures are exemplary (and may be approximate) and are in inches.

FIG. 45A is a front view of an assembled adapter electrode pad as described herein.

FIG. 45B is a side view. FIG. 45C illustrates the formation of the adapter electrode pads on and as part of a roll.

DETAILED DESCRIPTION

Figure 5:
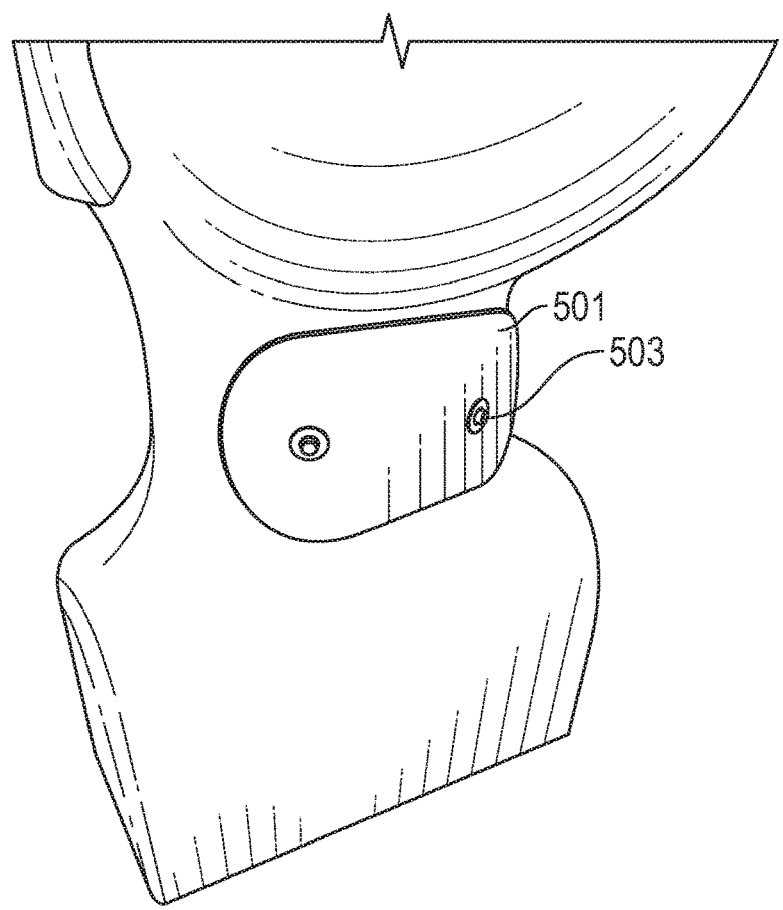
FIG. 5 illustrates one example of an electrode patch coupled to the midline of the back of a user's neck so that the first and second electrodes are oriented along the user's neck above the C7 region, but beneath the hairline (e.g., between the C1 and C7 regions of the spine).

In general, described herein are apparatuses and methods for applying transdermal electrical stimulation (TES) to the back of a subject's neck to modify a user's cognitive state and induce a relaxed state. In particular, described herein are electrode patches and neck-worn controllers that are adapted to deliver TES to a specific and particularly effective region of a patient's neck (and in some variations only this region) at or near the midline of the back of the neck between/over the C1 and C7 regions of the spine, beneath the hairline. Stimulation with the apparatuses and parameters described herein outside of this region, and with other parameters than those descried herein, are less effective or may be ineffective, and in some variations may induce contrary effects.

A generic system for applying transdermal electrical stimulation (TES) to the back of a subject's neck to modify a user's cognitive state and induce a relaxed state is illustrated in FIGS. 1A-1D. In this example, FIGS. 1A and 1B illustrate one example of an electrode patch (which may also or alternatively be referred to as an electrode strip, pad, electrode pad, contact strip, or the like). The electrode patch is configured and may be specifically adapted to be worn and easily applied to the back of the user's neck. In particular, the electrode patch may be configured so that it can be applied by user themselves without requiring a mirror or other tool, or without the intervention of a third party. For example the electrode body 105 may be shaped to enhance placement. The body 105 may be a thin (e.g., flat, generally planar, somewhat flexible) layered material. In FIG. 1A the schematic shows the body 105 as having an oval shape. In some variations it may be desirable to have a shape that is elongate that indicates the center region so that may be placed in/near the midline of the neck. For example, the body may be shaped in an hourglass or waisted shape (e.g. a lobed shape, such as a bi-lobed shape).

As shown in FIG. 1A, the electrodes that are configured to contact the user's skin 107, 109 are arranged vertically in the electrode patch, so that they may be applied in a line along the midline of the neck (e.g., where the midline of the back of the neck extends down from the top of the head along the spine near a central region of the neck). One of the electrode is preferably larger (e.g., has a larger surface area) than the other. For example, the lower electrode 109 in FIG. 1A is smaller than the upper electrode (in some variations the lower electrode is smaller than the upper electrode). In this example, the electrodes are approximately rectangular, although they may have other shapes, including oval, circular, or irregular. In this example, the electrodes include silver-coated, conductive contacts that are separated by about 1 inch 0.7 inches center to center (e.g., 1.2 to 0.6 inches, 1.1 to 0.65 inches, 1.0 to 1.7 inches, 1.0 to 0.8 inches, etc.). The first electrode 107 is approximately 0.95 inches by 1 inch and the lower (second) electrode 109 is approximately 1.24 inches by 2 inches. Surprisingly, the Applicants have found that having electrode pairs in which the electrodes are different surface areas gives better effects.

Figure 13:
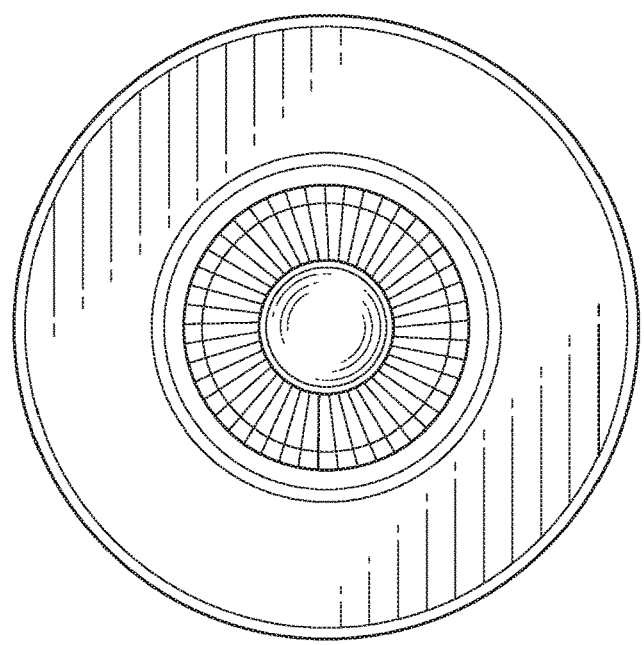
FIG. 13 illustrates one example of a self-connecting connector that may be included on either the neck-worn controller or the electrode patch and may form an electrical connection between the two for applying TES from one of the electrodes of the electrode patch. The connector consists of a donut shaped magnet, and a ferromagnetic disc shown in the center of the donut shaped magnet.

FIG. 1B shows an example of the back of the electrode patch shown in FIG. 1A. In this example, a first connector 111 is electrically connected through the body 105 to the first electrode 107 and the second connector 113 is electrically connected through the body 105 to the second electrode 109. The first and second connectors are configured to make electrical contact with electrical contacts on the neck-worn controller (see, e.g., FIG. 1C). FIG. 13 shows one example of a connector that may be used. This connector is electrically conductive and also (in this embodiment) is configured to self-connect to the neck-worn controller by virtue of forming a magnetic connection with the electrode-coupling region on the neck-worn controller. For example, in some variations the connector may be a ferrous or magnetic material or any other material that is strongly attracted to magnetic attachment on the electrode-coupling region of the neck-worn controller.

For example, the neck-worn controller shown in FIG. 1C is configured as a U-shaped, semi-rigid body 121. The arms of the body may be worn on either side of the user's neck and may include (e.g., house) or be connected to the controller circuitry, processor, memory, signal generator, etc., and/or power supply (e.g., battery, etc.) and/or wireless communications circuitry. In some variations the circuitry and/or power supply may be distributed between the end regions 151, 161 of the body 121 so that the weight and/or shape is balanced. The electrode coupling region 131 in this example is located centrally to be worn around the back of the user's neck. In some variations the electrode coupling region may be rigid.

As mentioned, the electrode coupling region is configured to automatically connect (in a proper orientation) and secure to the connector on an electrode patch worn on a user. In some variations the electrode coupling region may include one or more magnets (electromagnets, permanent magnetics such as neodymium iron boron (NdFeB), samarium cobalt (SmCo), alnico, and ceramic or ferrite magnets, etc.). Alternatively or additionally, the attachment may be a mechanical attachment such as a snap, etc. that forms the electrical connection. The attachment may be a hybrid electrical and mechanical attachment, such as an electrically conductive hook-and-latch (e.g., "conductive VELCRO") material. The self-connecting attachment may be integrated with or separate from the electrical connection. Alternatively or additionally, the attachment and/or connection may be physical and self-adhesive by employing conductive and adhesive materials to the patches like a hydrogel, hydrocolloid and the like.

FIG. 1D illustrates an electronic device 171 (e.g., a hand-held or wearable electronics device such as a smartphone, pad, smartwatch, etc.) that may be used along with the electrode patch and the neck-worn controller device. The electronic device may wirelessly communicate with the neck-worn controller and may be used to control any of the operations of the controller including: turning on/off the device, starting/stopping delivery of TES waveforms, pausing delivery of TES waveforms, user-control or modulation of the TES waveforms, user control or modulation of the intensity of TES applied (e.g., current amplitude, frequency, etc.), selecting which TES waveform to apply from a library of waveforms, tracking/logging use/operation of the apparatus, checking and reporting status of the apparatus, locking (e.g., parental lock, user lock, etc.) the apparatus use (security), etc.

FIGS. 2A-2D, similar to what is shown in FIG. 1A, illustrate variations of electrode positions and shapes that may be used on the patient-facing (skin facing) side of the electrode patch. In FIG. 2A the electrodes are shown as equal size surface areas, while in FIG. 2B the surface area of the upper electrode is >1.3× the surface area of the lower electrode. In FIG. 2C the electrodes are arranged horizontally rather than vertically, while in FIG. 2D the electrodes are arranged concentrically.

Similarly, FIGS. 3A-3D illustrate the configuration of various connectors that may be used to make electrical and/or mechanical connection. For example, in FIG. 3A the back of the electrode patch includes two electrical connectors 331, 332 that may make electrical and/or mechanical contact with the electrodes on the front, and an outer magnetic contact 335 at least partially surrounds them, extending at the periphery of the body of the electrode patch. Thus, the magnetic contact 335 may mate with a magnet on the electrode coupling region.

FIG. 3B shows another variation with a pair of electrical connectors 331', 332 and a magnetic contact 335' in the middle. FIGS. 3C and 3D show other variations in which the connectors may be hybrid connectors (e.g., that act both to magnetically or otherwise attract/connect to the electrode coupling region of the neck-worn controller).

FIGS. 4A and 4B illustrate variations of neck-worn controllers. In FIG. 4A the elongate body 405 is pliable or flexible. A rigid electrode coupling region 421 is located at one end and may self-connect to an electrode patch on the user's neck. The controller electronics (circuitry, not shown), battery and wireless communication circuitry may be located within the elongate body and/or at the distal end region 433. The example shown in FIG. 4B also includes a flexible elongate body 405', but is configured to wrap around both sides of the user's neck when worn. The electrode coupling region 421' is in a central region.

In general, the apparatus is configured so that the electrode patch is applied beneath the user's hairline, in the cervical region of the back of the neck (e.g., down to approximately C7 spinal region). This midline location and spinal level may help the TES applied as described herein in correctly activating and/or inhibiting nerves under the electrode patch and may improve parasympathetic drive and inhibit sympathetic drive at this cervical region. The electrode pair is generally placed behind the neck, so that the top electrode is close to the hairline around the center (midline) of the spine. The second electrode is about an inch (e.g., between 0.6 and 1.3 inches, 0.7 and 1.2 inches, 0.8 and 1.2 inches, etc.) below the first electrode. The two electrodes may be connected to the connectors. In some variations the connectors are iron, steel, or other material that may be magnetically attracted and held. These connectors may be snaps that can make an electrical and/or mechanical connection. In some examples they may be placed on the left and right sides of the neck.

FIG. 5 shows an example in which steel snaps are placed on the left and right side of the back of the neck when the electrode patch is worn on the back of the neck. In this example the electrode patch 501 includes an adhesive for holding it to in contact with the skin. The self-connecting connectors 503 are steel snaps that can be magnetically attracted, held and form an electrical connection to the electrodes on the inner side of the electrode patch (not visible).

Figure 6:
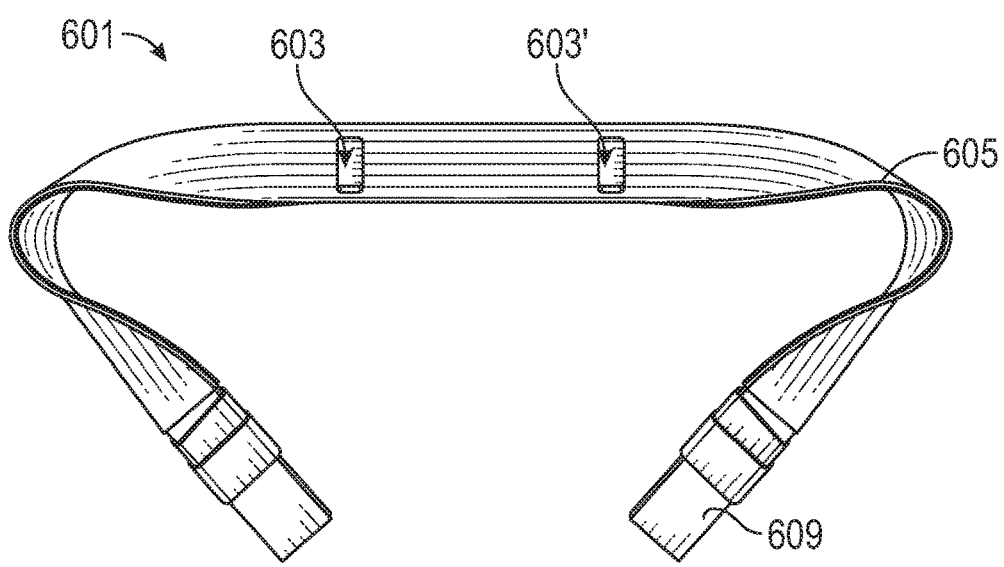
FIG. 6 shows one example of a neck-worn controller that self-connects to an electrode patch.

As illustrated in the example shown in FIG. 6, a neck-worn controller 601 may include one or more magnets 603, 603' that are affixed to the elongate body 605 of the device. In this example, the electronics for generating and delivering the TES to the electrodes when the electrode patch is connected may be held at the end(s) of the elongate body 609, which in this example is a flexible (e.g., fabric) member.

Figure 7A:
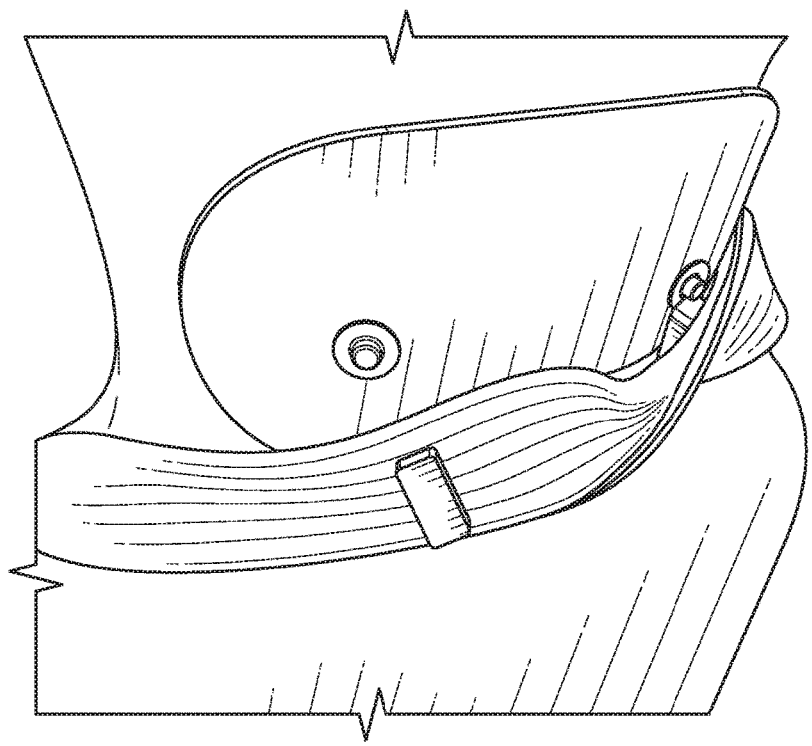
FIGS. 7A and 7B illustrate the electrode patch of FIG. 5 self-coupling (in this example, magnetically however, other techniques for self-coupling may be used, such as mechanical, chemical, etc.) to the neck-worn controller of FIG. 6.
Figure 7B:
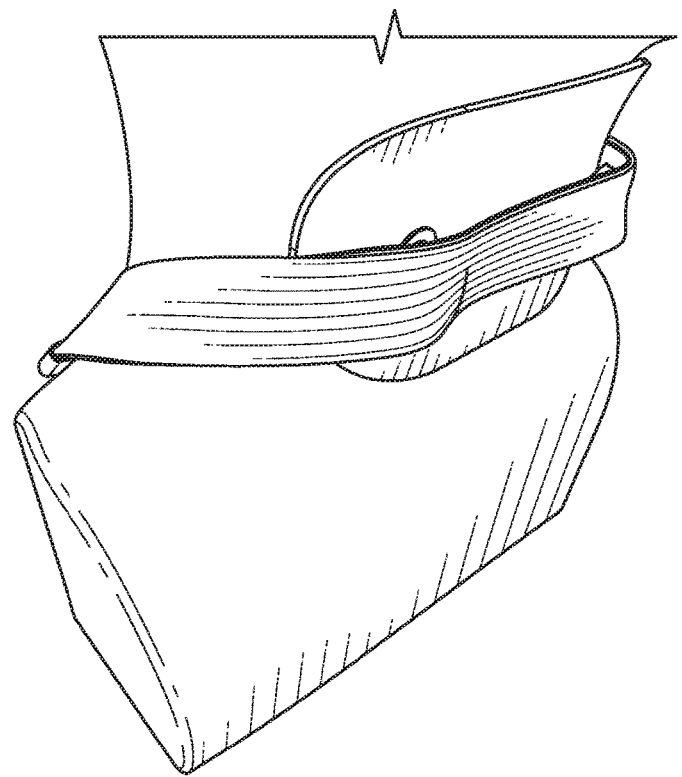

In operation, as shown in FIG. 7A, the magnets in the neck-worn controller may be attracted to the steep snaps even if they are initially a distance (e.g., up to 1 inch in some variations, generally less than 1.2 inches, 1.2 inches, 1.0 inches, 0.9 inches, 0.8 inches, etc. away). As shown in FIG. 7B, once connected, the neck-worn controller may rest comfortably behind the user's neck. In the example shown in FIGS. 7A-7B, the elongate body of the neck-worn controller is an elastic band.

Figure 8:
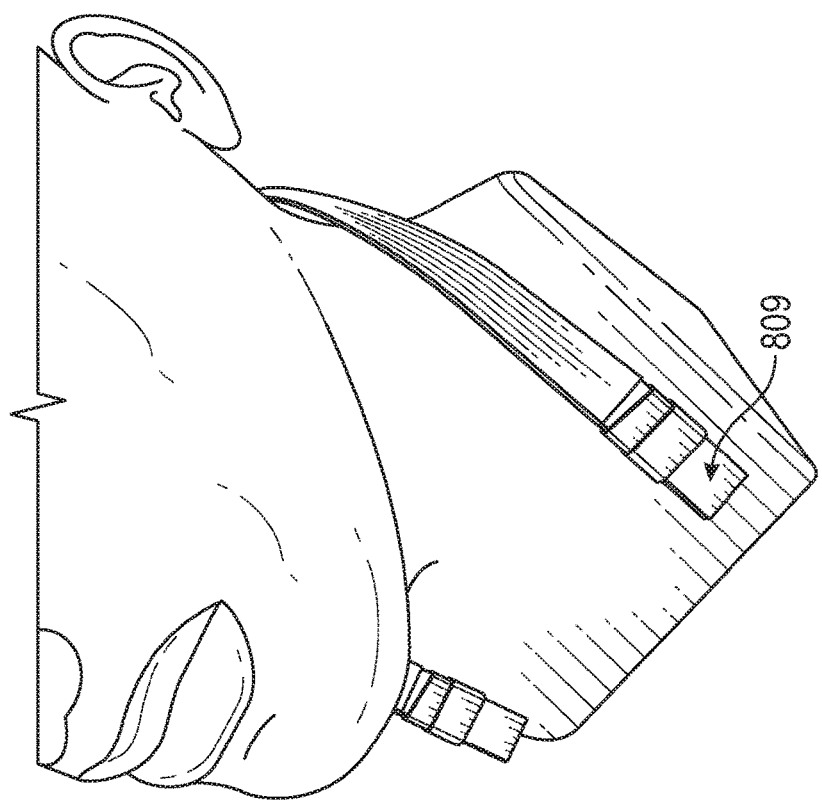
FIG. 8 shows a side perspective view of the neck-worn controller such as the one shown in FIGS. 6 and 7A-7B connected to an electrode patch on the back of a user's neck.

As shown in FIG. 8, the ends of neck-worn controller may include one more controls (buttons, switches, dials, etc.) 809 for control of the operation either separately or in addition to wireless control using an electronics device. The electronics device may be a dedicated device (e.g., hardware and/or software and/or firmware) for wirelessly controlling operation of the device, or it may be a user-provided devices such as a smartphone, pad or wearable electronics (e.g., smartwatch, etc.) running software (e.g. an application software) or communicating with a remote server to control operation of the neck worn applicator and therefore TES application. In FIG. 8, placing the buttons in the front near the end(s) may make them easy to access by the user.

Figure 9:
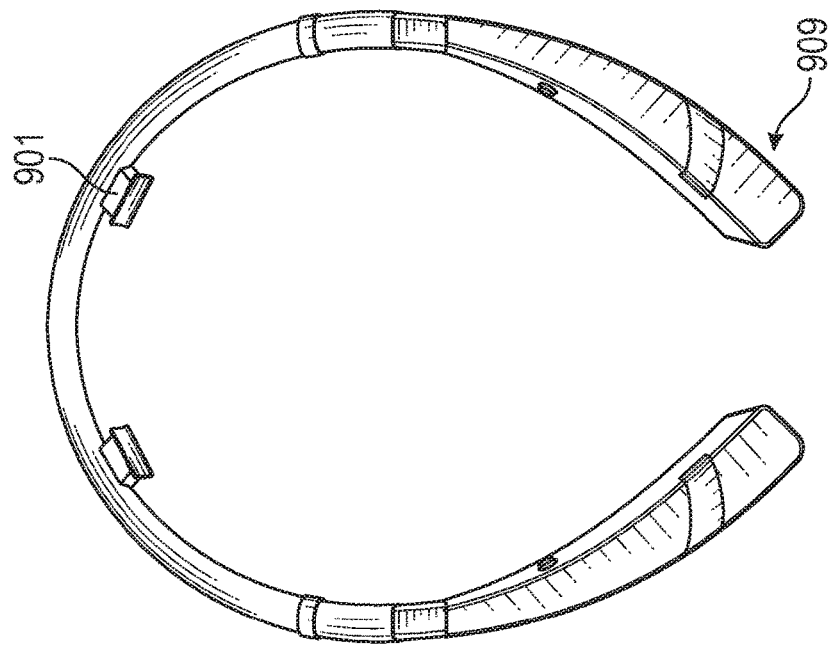
FIG. 9 shows another example of a neck-worn controller configured to connect to two or more connectors (including self-connecting connectors such as magnetic connectors) on an electrode patch. In this example, the neck-worn controller may be rigid or semi-rigid (e.g., may include regions that are less rigid, and/or may include hinged regions).
Figure 10:
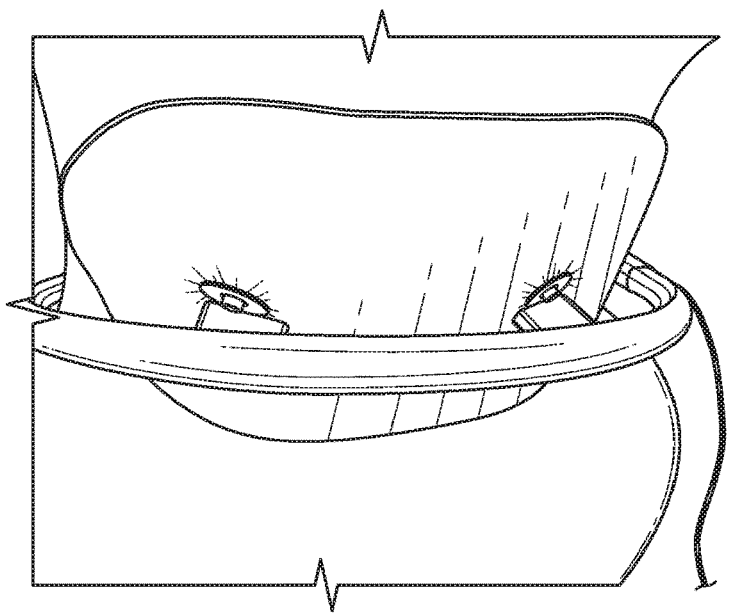
FIG. 10 illustrates the neck-worn controller of FIG. 9 coupled to an electrode pad (e.g., electrode patch) on the back of a user's neck.
Figure 11:
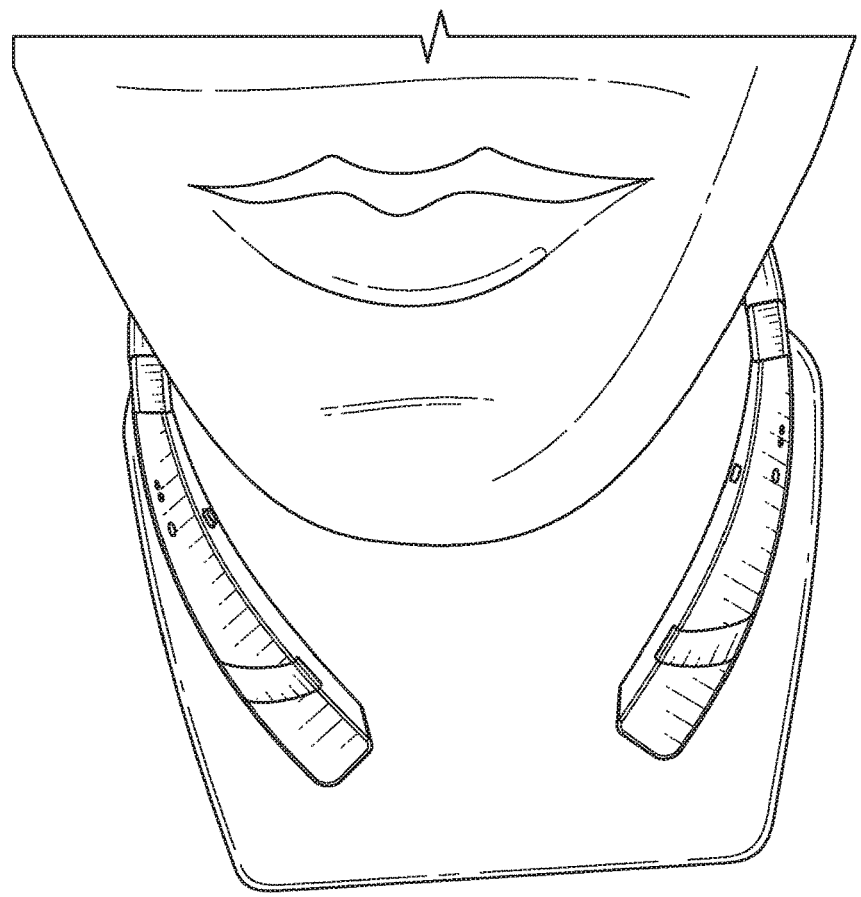
FIG. 11 shows a front view of the neck-worn controller of FIGS. 9 and 10 draped around the front of the user's neck.

FIG. 9 is another example of a neck-worn controller device. In FIG. 9 the device body may be rigid or semi-rigid, and is shown as U-shaped. The body may be pulled open to apply onto the user's neck. In this example a pair of magnets 901 may be used to magnetically self-connect (and align and secure) the neck-worn controller to an electrode patch on the user's neck, as shown in FIG. 10. The device may include the control electronics inside of the elongate body, which may include a housing 909 for holding them.

Any of the variations described herein could also include an output (e.g., LED) showing status of the device as it operates, and/or the operational state of the device. In some variations the apparatus includes speakers (e.g., ear buds that may be worn in the ears) and may also be configured to play music or other audio content. For example, in any of the apparatuses and methods described herein, the neck-worn controller may include a radio, music player, and/or may wireless communicate with a music or other source of audio (CD player, digital music player, radio, etc. including a phone). The audio content (music, ambient noise, etc.) may be synchronized or otherwise coordinated with the applied TES waveforms. In some variations the music (tempo, changes/transitions in tempo, etc.) could trigger or modulate the TES waveform parameters (including one or more of the parameters of AM as described in FIGS. 21A-23, below).

Any of these variations may also or additionally include a charging or other input/output port, such as a mircoUSB port. Alternatively or additionally the devices may include an inductive charging circuit or any other appropriate charging apparatus.

Figure 12:
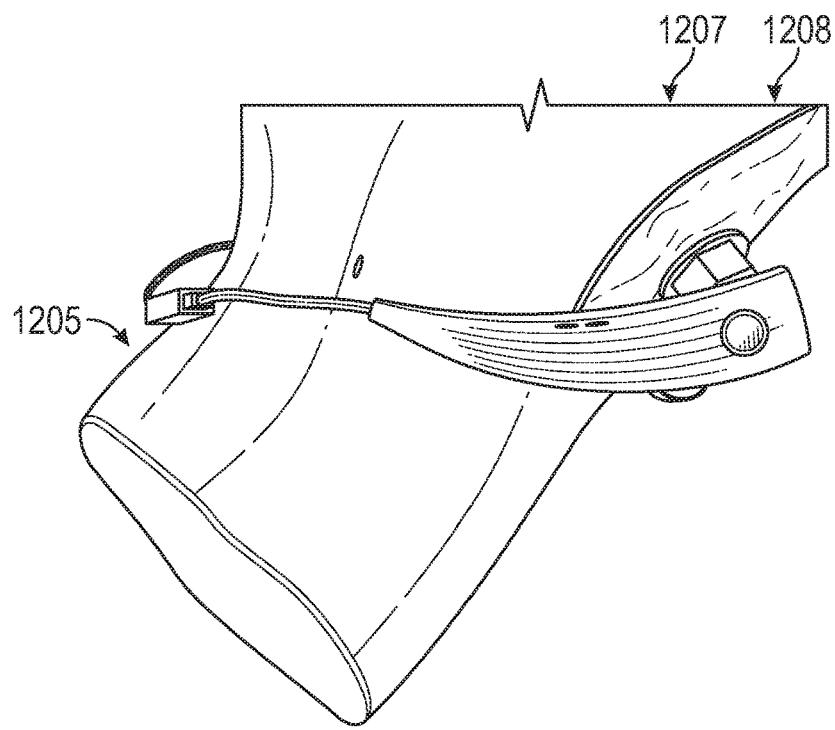
FIG. 12 illustrates another example of a neck-worn controller in which the neck-worn controller is configured to extend around only one side of the user's neck.

FIG. 12 is another example, similar to that shown in FIG. 4A, in which the device is configured to be worn on one side of the user's neck, when self-attached to the electrode patch. In this variation the neck-worn controller drapes over the user's neck on one side, so that the magnets 1207, 1208 are attached behind the neck to connecting electrodes on the electrode patch, and the internal electronics are located at the opposite end 1205.

Figure 14:
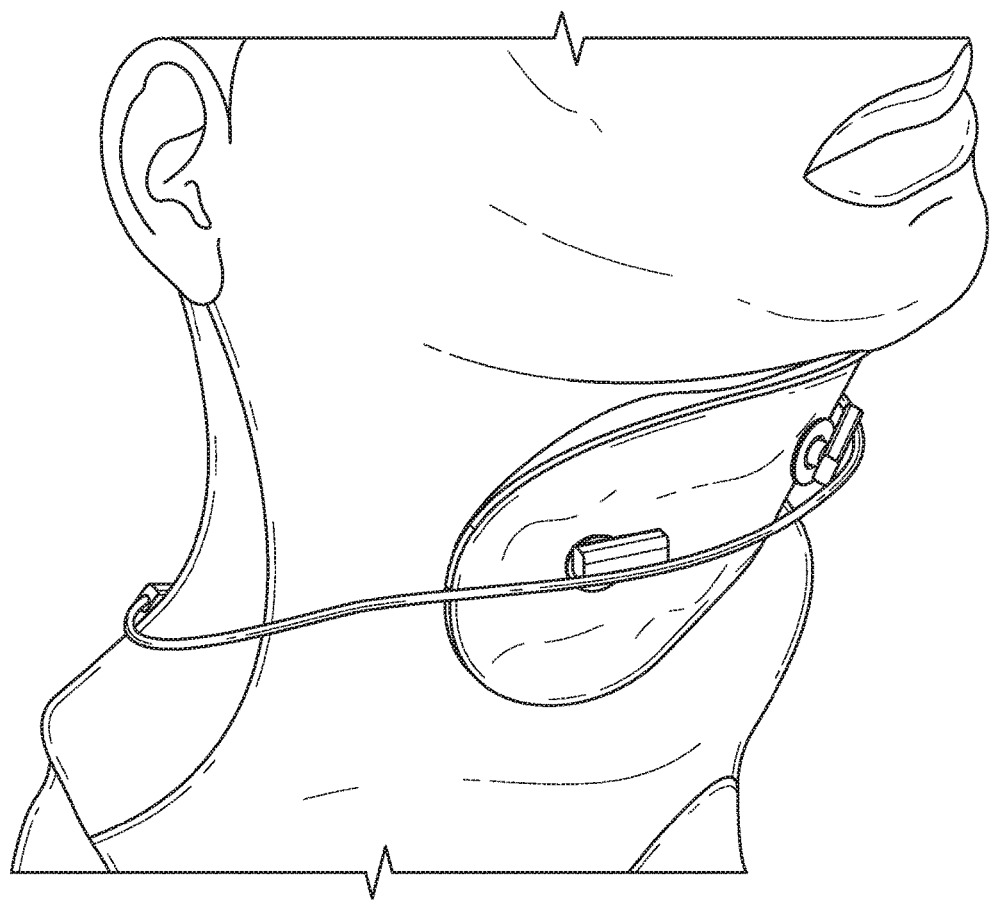
FIG. 14 illustrates another example of a neck-worn controller in which the body of the neck-worn controller extending from the connector region (that connects to the electrode patch) is thin and flexible.
Figure 15:
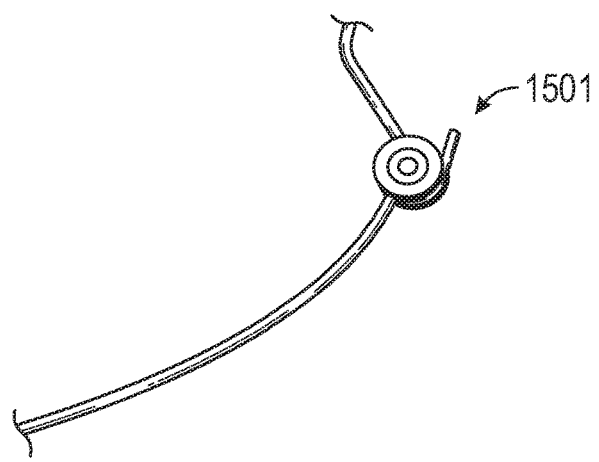
FIG. 15 illustrates an example of a hinge region of a neck-worn controller.

The exemplary neck-worn connector shown in FIG. 14 is very thin and is configured as a wire that may include one or more (e.g., two) rigid regions at the electrode-coupling region for connecting to the connectors on the electrode patch. In some variations, as shown in FIG. 15, the neck-worn controller device may include a hinge 1501 or more flexible region that will allow the device to be taken on/off the user's neck even when the body is generally more rigid.

Figure 16A:
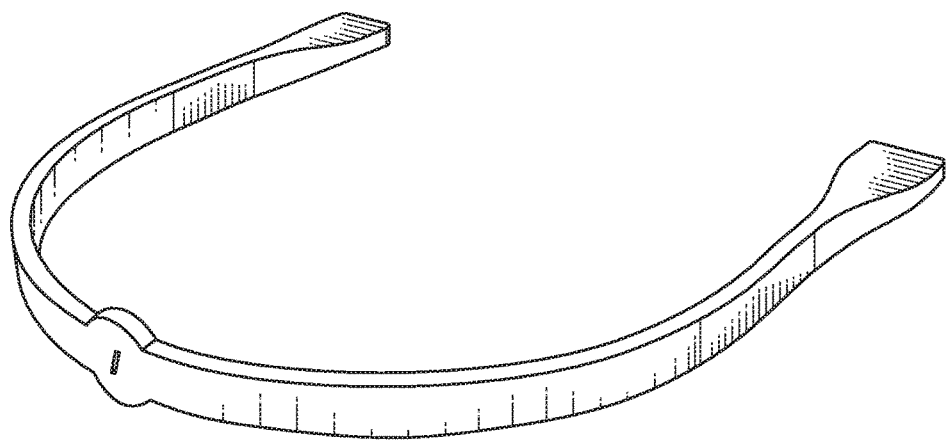
FIGS. 16A and 16B show an example of a neck-worn controller that is rigid or semi-rigid.
Figure 16B:
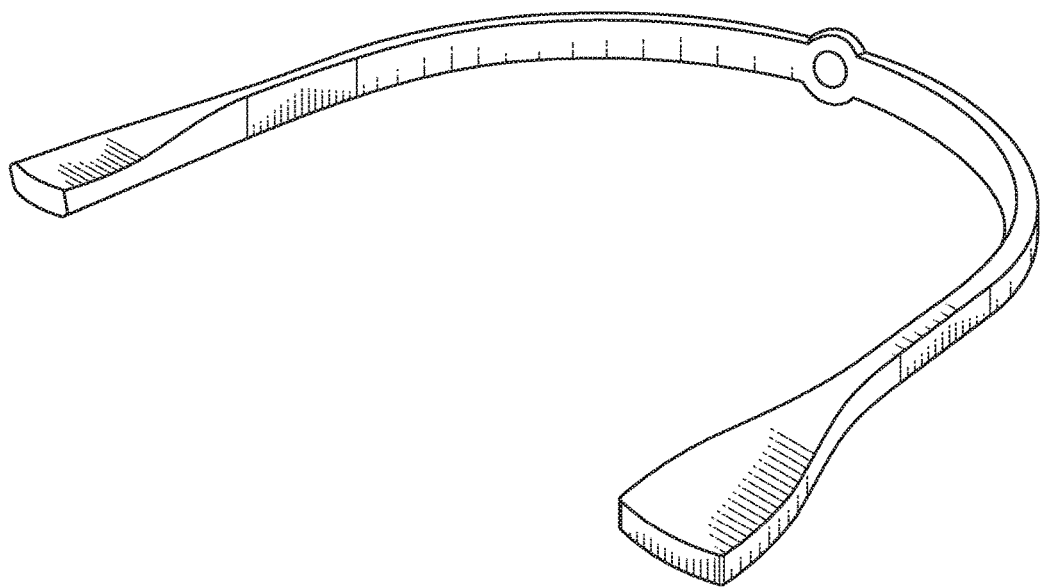
Figure 17A:
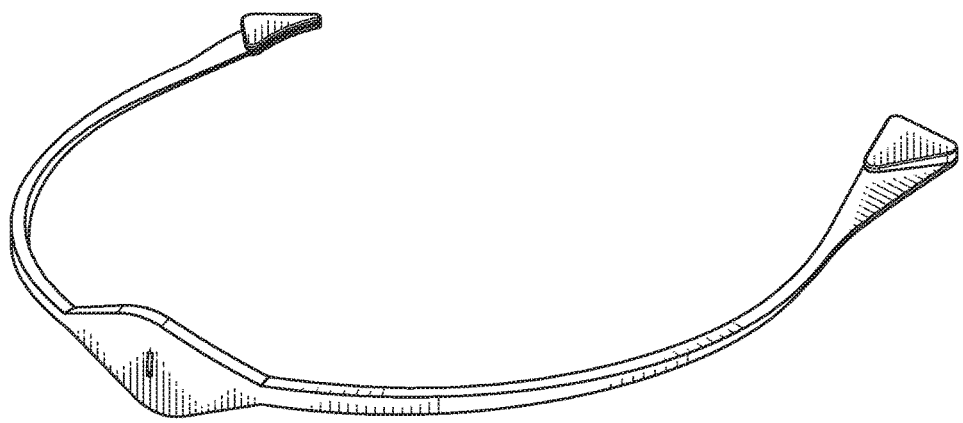
FIGS. 17A-17C illustrate another example of a neck-worn controller.
Figure 17B:
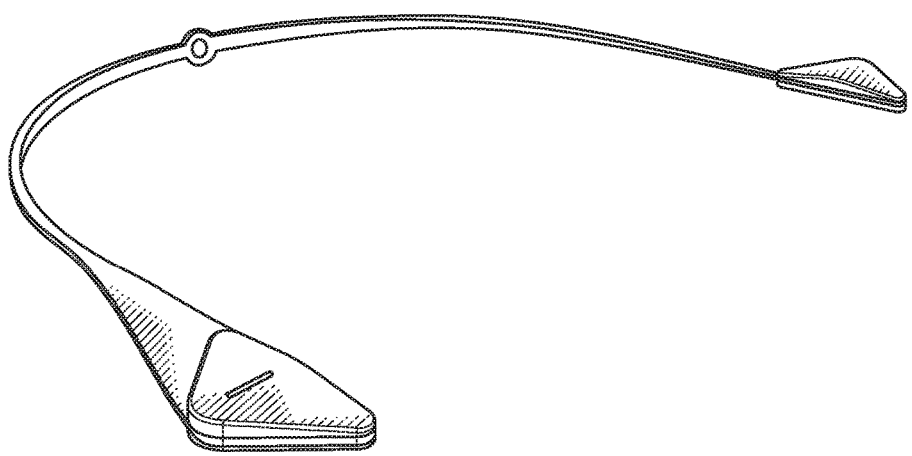
Figure 17C:
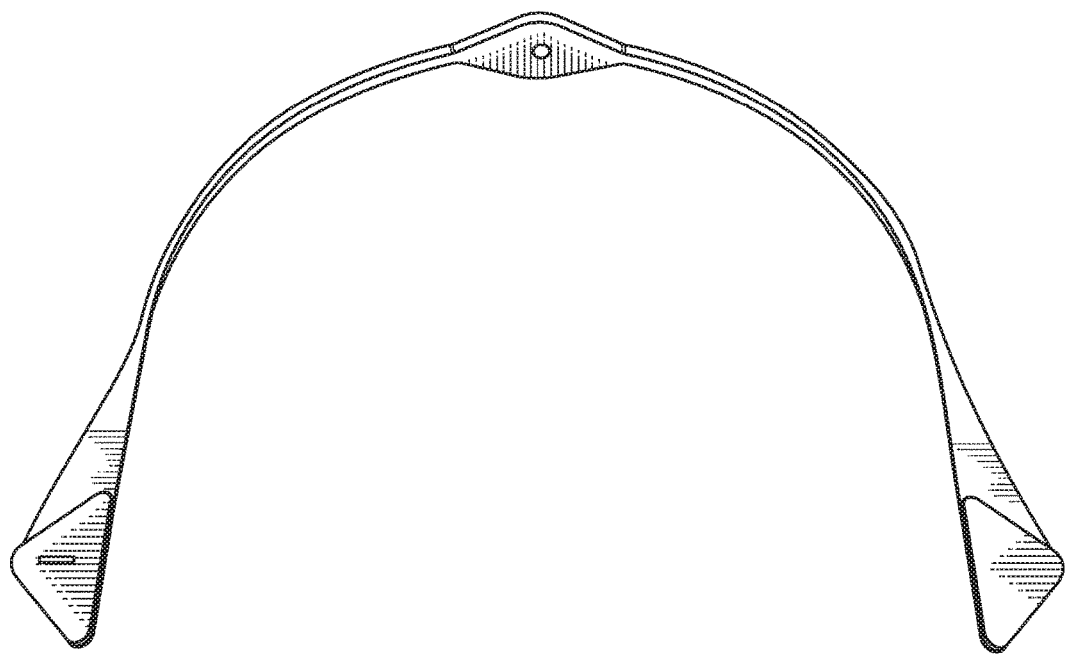
Figure 18A:
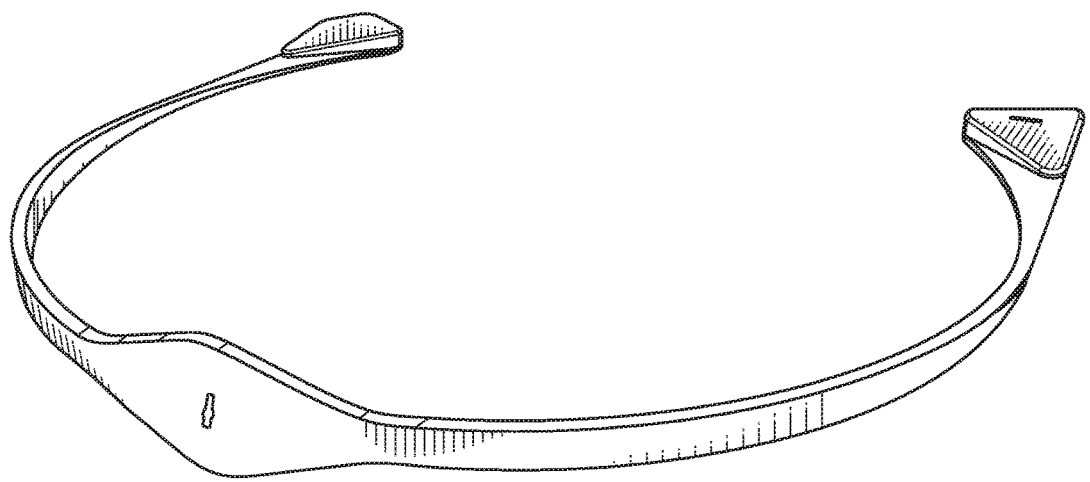
FIGS. 18A-18C show another example of a neck-worn controller.
Figure 18B:
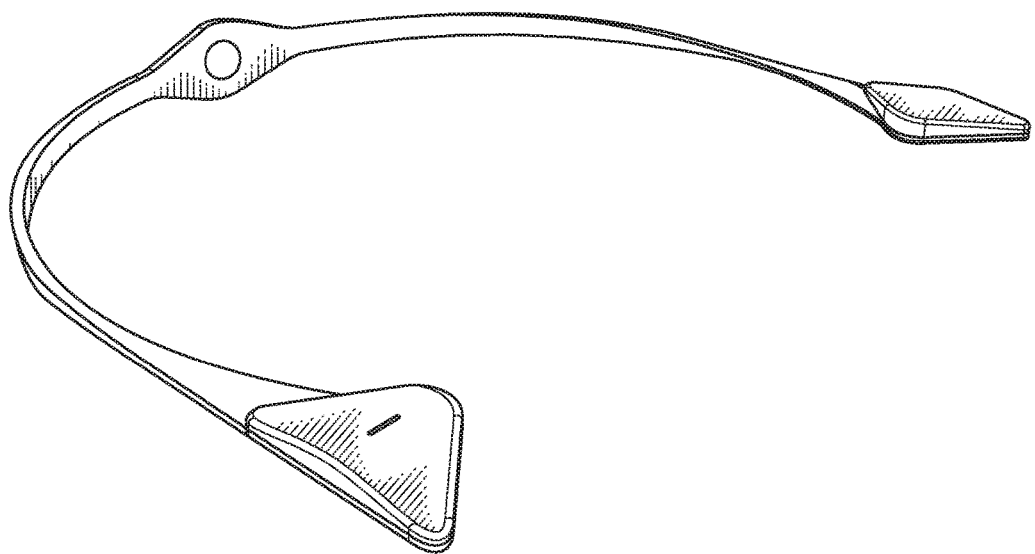
Figure 18C:
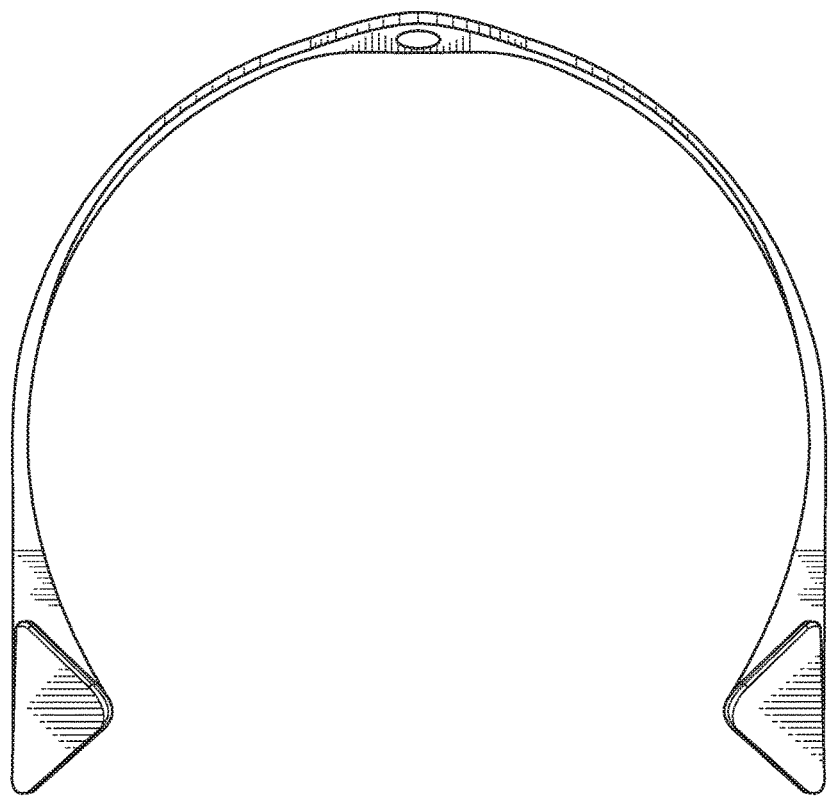

FIGS. 16A and 16B illustrate an example of another variation of a neck-worn controller device having a generally U-shape. FIGS. 17A-17C show another variation with a slightly different form factor. Finally, FIGS. 18A-18C show another variation having a rigid or semi-rigid elongate body that is generally U-shaped, an electrode-coupling region near the middle of the body, and wherein the body holds the power source (e.g., large-capacity capacitor, rechargeable battery, etc.), control circuitry and wireless communication circuitry.

Signal Modulation

As described above, any of the devices described herein are configured to apply transdermal electrical stimulation to achieve neuromodulation (e.g., through the back of the neck). Both the TES application location at the midline of the back of the user's neck and the waveforms applied ("TES waveforms") have been optimized to induce a relaxed mental state.

Figure 19:
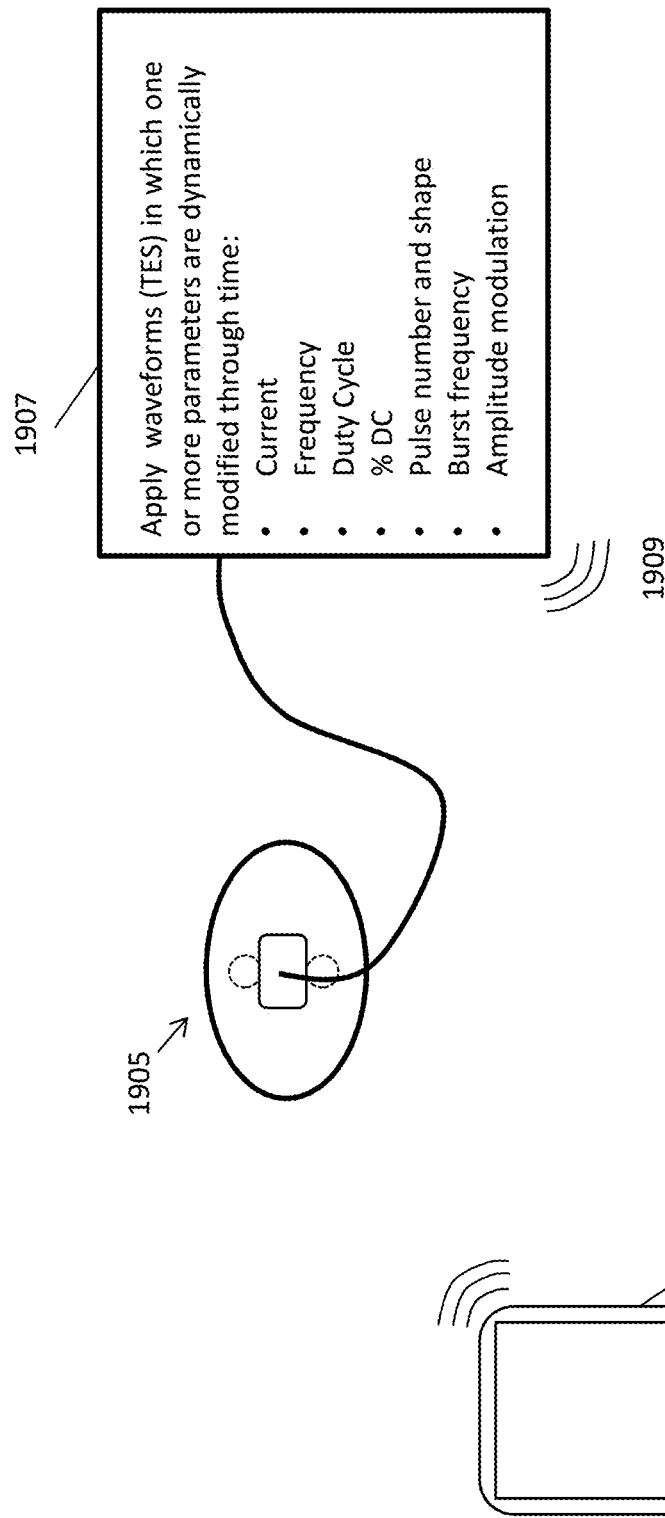
FIG. 19 schematically illustrates operation of a system for applying TES to induce a calm or relaxed metal state by neuromodulation through a user's neck region.

For example, FIG. 19 schematically illustrates the operation of a system as described herein. In this example, a pair of electrodes (which may be an electrode patch 1905 or separate electrode patches) are connected to a user's neck, including in some variations (but not necessary) via a neck worn controller or other controller (shown schematically by box 1907). The controller generates and applies the TES waveform. The controller may be directly connected to the electrodes (via physical connection, e.g., wire, lead, etc.) or via a wireless connection. In general, these TES waveforms may include a relatively high frequency carrier wave (e.g., >250 Hz, greater than 1 kHz, greater than 2.5 kHz, greater than 5 kHz, greater than 7 kHz, greater than 9 kHz, greater than 10 kHz, etc., between 250 Hz-50 kHz, between 250 Hz-35 kHz, etc.). One or more parameters of the carrier waves may be varied or modulated, including one or more of: current, frequency, duty cycle, percent (%) DC, pulse number and shape, and/or burst frequency. Alternatively and surprisingly, these parameters may be kept relatively stable throughout the TES and the TES signal may be amplitude modulated, and particularly may be variably amplitude modulated, in which one or more parameters of the amplitude modulation (which typically has a lower frequency by approximately $\frac{1}{10}^{th}$ of the carrier wave frequency or less (e.g., less than 1 kHz, 950 Hz, 900 Hz, 850 Hz, 800 Hz, 750 Hz, etc.). During operation, the one or more AM parameters are varied during every 30 seconds or faster (e.g., <30 seconds, <25 seconds, <20 seconds, <15 seconds, <10 seconds, etc.).

In the example of FIG. 19, the electrode-driving controller 1907 may coordinate the activity of the voltage/current source (e.g., battery, voltage and/or current regulating circuitry), clocks, and other circuitry to deliver waveforms (or an ensemble of waveforms) to the electrodes. The local controller 1907 connected to the electrodes may also regulate the electrodes themselves (e.g., monitoring and adjusting the wetness of the electrodes, as described herein). The local controller may also receive input from a remote controller, including user-held device (e.g., handheld user electronics device such as a smartphone, wearable electronics, etc.) 1913. The user-held device may send commands (start/stop, intensity control information, waveform parameters, etc.) to the local controller 1907. In FIG. 19 this communication is shown to be wireless 1909. For example, a user may operate a smartphone or other user-held device (tablet, pad, laptop, etc.) to control operation of the local controller 1907. The user-held device may run software (such as an application software) including a user interface. In some variations a separate user-held device is not used, and the local controller may integrate all or some of the features of the user-held device.

Amplitude modulation typically applies an envelope (e.g., bursting) at a lower frequency that modulates the peak amplitude of the carrier wave forming the waveform. Transitions in the TES waveforms may include changes in frequency, amplitude, duty cycle, etc., as shown in FIG. 21A; alternatively or additionally, the changes in TES waveforms may be transitions incorporated by the apparatus in the amplitude modulation characteristics. See, for example, FIG. 22.

Figure 22:
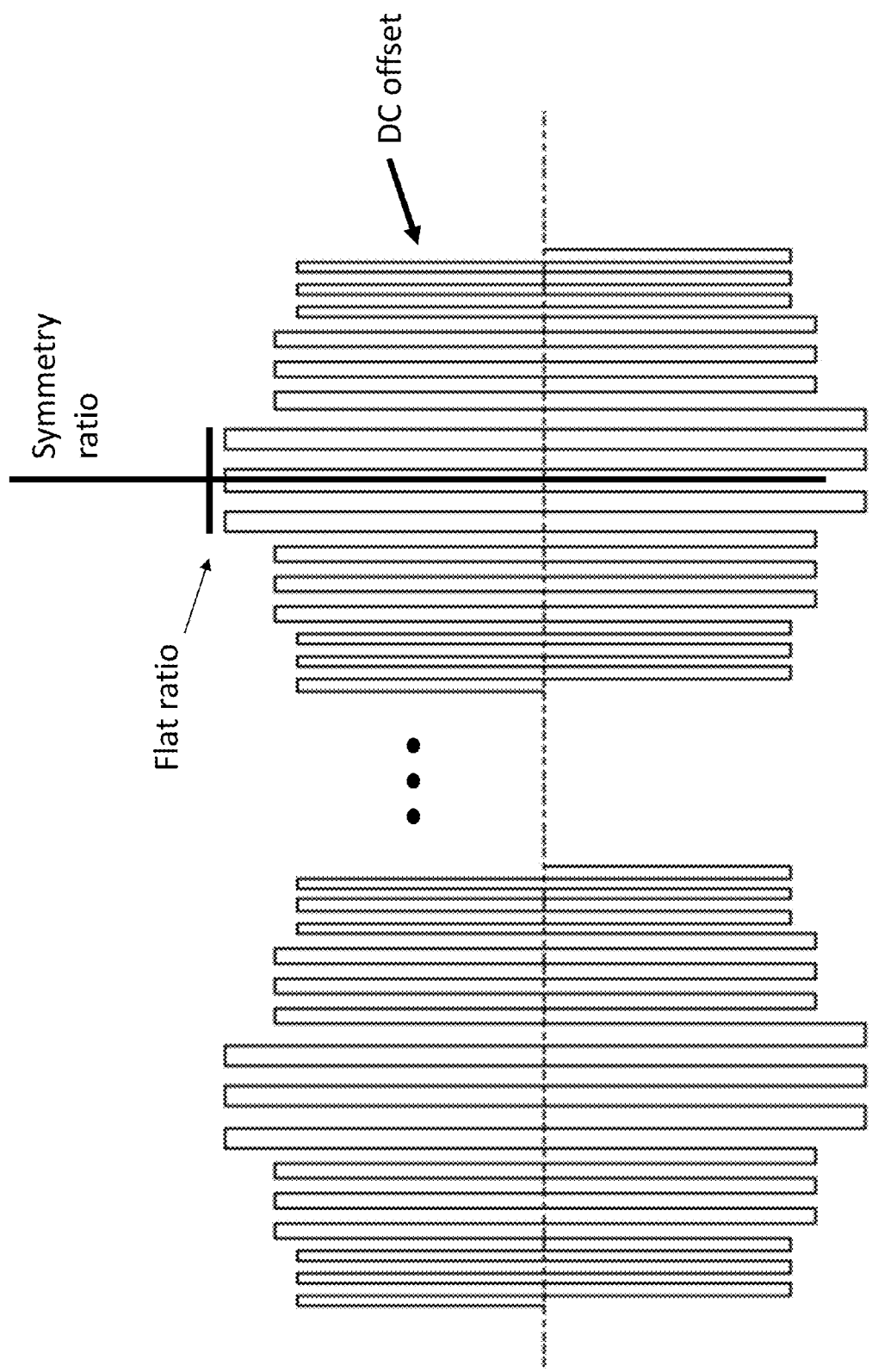
FIG. 22 illustrates variable parameters that may be modified by the variable amplitude modulation methods described herein.

FIG. 22 graphically illustrates the amplitude modulation (AM) of a carrier frequency, showing two complete periods of the amplitude modulation. In general, the amplitude modulation may have bursting, resulting in a periods where the envelope results in no signal (0 amplitude), or it may switch the polarity of the signal (as shown in FIG. 22). FIG. 22 also graphically illustrates the symmetry ratio of the AM, in which the symmetry ratio is the percent of the total area to the AM signal to the left of the midline 2201 of the period divided by the total area of the period of the AM signal. In FIG. 22, the Symmetry ration is 50 (50%). The flat ratio is also illustrated, and is the percent of the duration of a single period in which the AM signal stays at peak (e.g., in FIG. 22 the Flat ratio is approximately 20, or 20%).

An example of the compound waveform (ensemble waveform) for use with any of the methods and apparatuses descried herein is shown in the table in FIG. 23. In this example, each parameter is held in a particular value for the time period indicated; the cognitive effect of relaxation may result because of the transitions between these parameter values. For example, in FIG. 23, the apparatus initially starts from an "off" setting (0 values for all parameters) and increases to the values shown in the first column (e.g., during the first 15 seconds). Thereafter, they are held for 45 seconds, then the carrier frequency is shifted only very slightly (if at all), while the frequency of the AM modulation is cut in half, from 800 Hz to 400 Hz; after another 25 seconds, this is switched back to 800 Hz, and so on. This variable AM results in a profound user experience of relaxation.

Thus, by creating transitions in the flat ratio, symmetry ratio and DC offset in the amplitude modulation, the apparatus may greatly enhance the efficacy of the TMS waveform applied in evoking a relaxed cognitive state. For example, during the application of a TMS waveform, the amplitude modulation maybe transitioned (e.g., every 1-30 seconds) from a square shape to a saw tooth to a trapezoid shape; the carrier wave may have an amplitude from between 1-30 mA, a frequency of between 250 Hz and 50 kHz, be biphasic (and in some variations asymmetric), similar to what is shown in FIG. 20.

Figure 20:
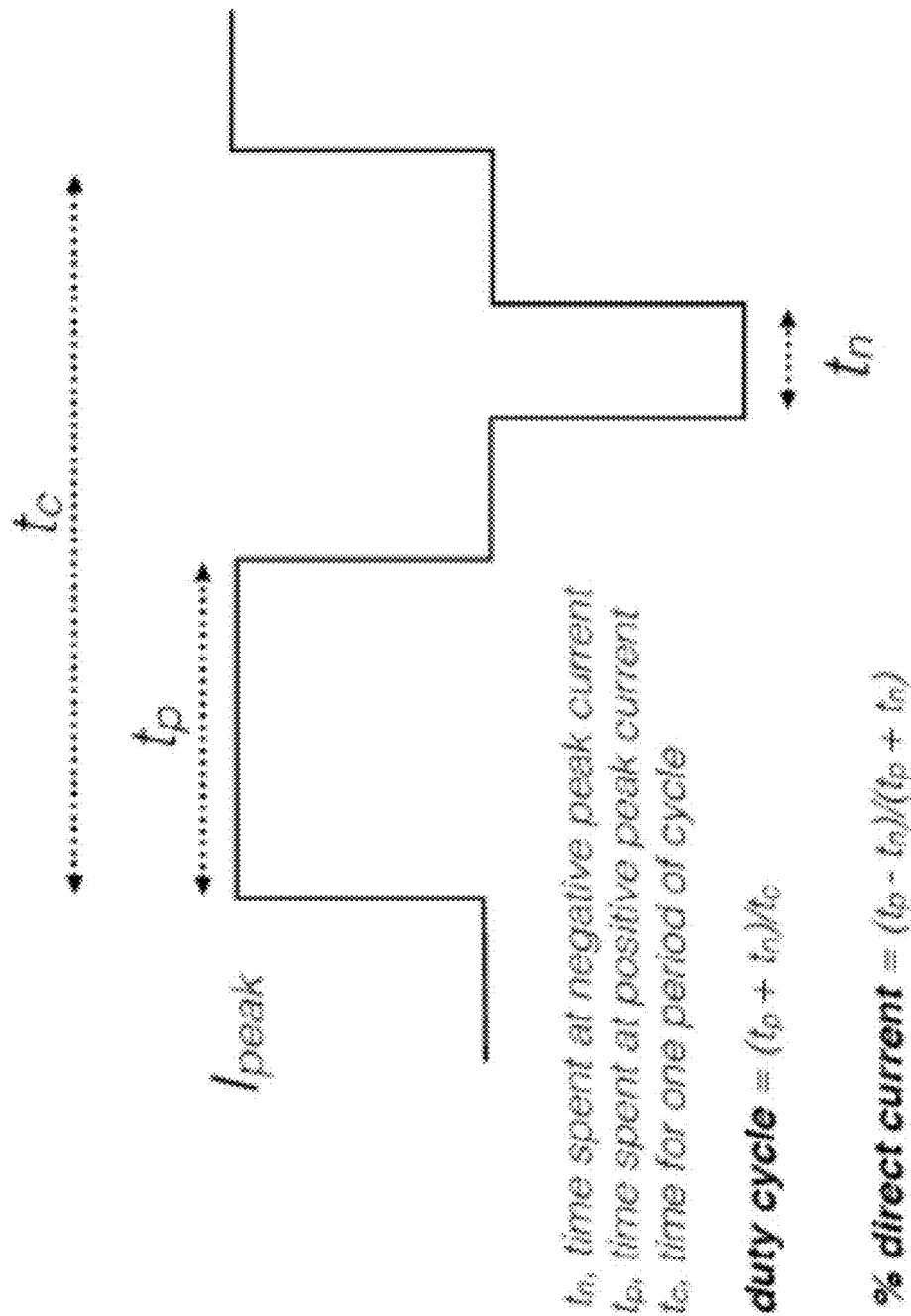
FIG. 20 illustrates characteristics of a carrier wave that may be used to apply TES neuromodulation a described herein.

In general, a TES carrier waveform such as shown in FIG. 20 may be defined by a duration, direction, peak current, and frequency. In some embodiments, a TES carrier waveform is further defined by a percent duty cycle (FIG. 20), percent direct current (FIG. 20), ramping or other amplitude modulation, one or multiple frequency components, phase relationship of biphasic current, flat or structured noise, wave shapes (i.e. saw tooth, triangular, sine wave, square wave, exponential, or other wave shape), capacitance compensation features, or other parameters. As used herein, 'percent duty cycle' may refer to the proportion of a cycle of a waveform that causes non-zero (or nominally non-zero) current to be delivered transdermally (see equation, FIG. 20). Further, 'percent direct current' may refer to the non-zero portion of a waveform cycle that is positive-going (see equation, FIG. 20).

In some variations, amplitude modulation below 100 Hz may be particularly effective, including amplitude modulation at frequencies as low as 10 Hz (e.g., between 10 Hz and 100 Hz); this AM frequency when used to modulate a carrier wave as described herein in regions other than the midline of the back of the neck is not typically effective to induce relaxation. For example, amplitude modulation frequency as low as or lower than 100 Hz when applied to the neck and temple region are not effective, often causing pain and disturbing flashes of light.

Also described herein are TMS waveforms in which the polarity of the electrodes (anode and cathode) may be switched during the TMS application by the neck-worn controller.

Although the apparatuses and methods described herein are primarily for use in inducing relaxation (calm) by applying particular subsets of TES to just the region in the back of the user's neck, these methods and apparatuses may be modified for use with additional electrodes on other body regions, including the temple; interestingly, the inventors have found that a feeling of euphoria may be induced when stimulating with some of the waveforms described herein when applied between an electrode on the midline of the neck (between the C1-C7 region) and an electrode on the forehead.

EXAMPLES

Figure 24A:
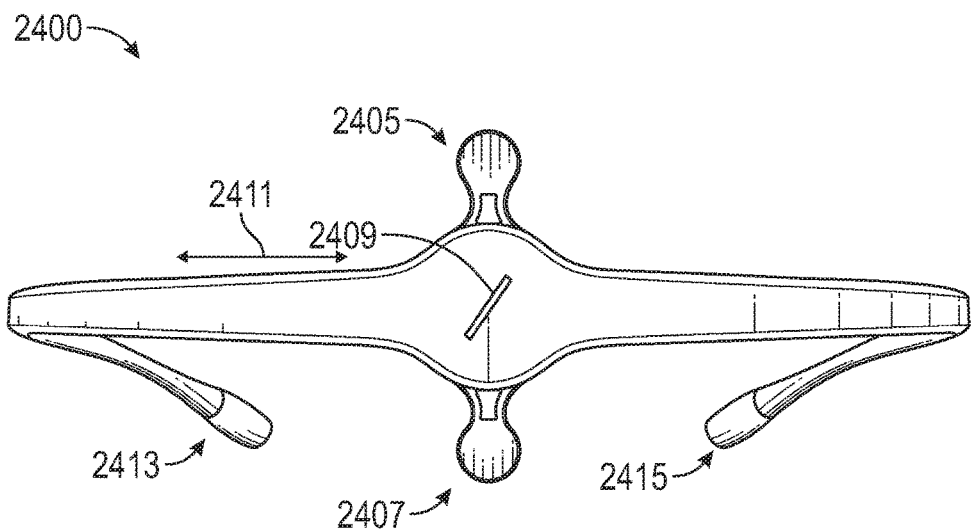
FIGS. 24A-24D illustrate another example of a neck-worn controller (e.g., TES controller/stimulator) that is rigid or semi-rigid, including attachment sites for electrodes.

FIGS. 24A-242D illustrate another example of a neck-worn TES apparatus that includes a pair of electrodes (or connectors to couple to electrodes) configured to contact the midline of the back of a user's neck. Although many of the examples shows and discussed above include a magnetic attachment between the electrodes, such as electrode patches that include an adhesive and/or a conductive gel, any of the apparatuses described herein that use an electrode may be configured to instead of additional use a dry electrode (without a conducive gel), a self-wetting electrode, a self-cleaning electrode and/or an integrated electrode that does not removably couple to an electrical contact.

FIG. 24A shows the back of a neck-worn TES apparatus 2400. This exemplary apparatus is a semi-rigid torc (having a u-shaped body) that is configured to be worn around the user's neck. In this example the pair of electrodes 2405, 2407 extend perpendicular to the long, curving axis of the torc body 2411. Each electrode 2405, 2407 is connected to the torc body through an electrical contact. In this example, a pair of electrical contacts are arranged adjacent to each other and separated by between 5 mm and 60 mm apart (approximately 40 mm in this example, center-to-center). The electrical contacts are positioned in the middle region of the torc body, and form an electrode-coupling region, where the electrode couples to the user's neck. The electrical contact supports and backs the skin-contacting electrode. As mentioned, in some variation the skin-contacting electrode may be removably coupled to the electrical contact (including self-coupling, such as magnetically coupling), and/or it may be integrated on the electrical support. In FIG. 24, the electrodes are shown as reusable "dry" electrodes (e.g., not including a gel); in some variations they may be self-wetting electrodes/re-wettable electrodes as will be described in greater detail below.

The neck-worn TES apparatus may also include one or more indicator lights 2409, such as LEDS that may indicate operation of the device. The ends of the neck-worn device(s) (e.g., first end 2413 and second end 2415) may hold some of the electronics (e.g., controller, battery, antenna, etc.). Any of these devices may also include one or more speakers, headset (e.g., earbuds, etc.) or the like, and may include a tuner (e.g., for connecting to commercial radio or wireless radio to play audio content) and/or memory (e.g. for playing stored audio files, including digital audio content).

Figure 24B:
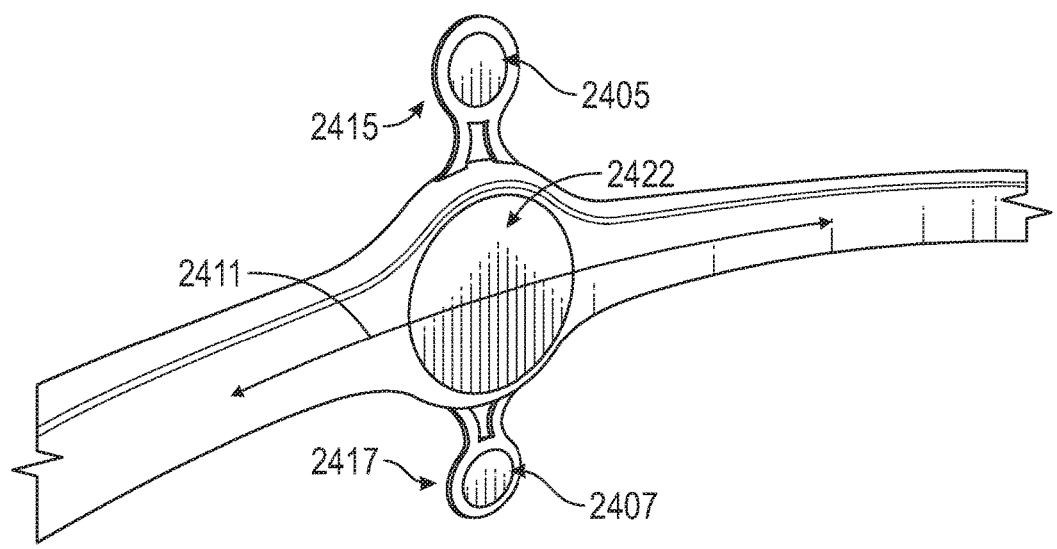

FIG. 24B shows an enlarged view of the electrode-coupling region near middle region of torc body between the first and second ends. The electrode-coupling region typically couples the electrodes to the user's (the person wearing the apparatus) neck. In FIG. 24B the electrodes 2405, 2407 are visible and are shown connected to the electrical contacts that support them 2415, 2417. The electrodes in this example are integrated onto the electrical contacts (shown here as electrode supports 2415, 2417). Any of these apparatuses may also include a region or portion 2422 that may include one or more sensors (e.g., skin sensors, sensors detecting contact/wetness of the electrodes, etc.), adhesive, and/or may house any of the circuitry and/or fluid storage reservoirs for use in rewetting electrodes.

As will be described below in reference to FIGS. 25A and 25B, the electrode supports may be biased so that they hold the electrodes against the user's neck when the torc is worn.

For example, the electrode supports may include an arm or arms that is angled or biased inwards (e.g., towards the neck, when worn). The weight of the torc may help hold the electrodes against the user's neck. In some variations the ends of the apparatus body may be weighted (e.g., may weigh more than 5 grams, more than 10 grams, more than 15 grams, more than 20 grams, more than 25 grams, more than 30 grams, more than 35 grams, more than 40 grams, etc.), each. The electrode supports may be configured as a spring arm (e.g., leaf spring, etc.), or may include a bias (e.g., spring) element.

Figure 24C:
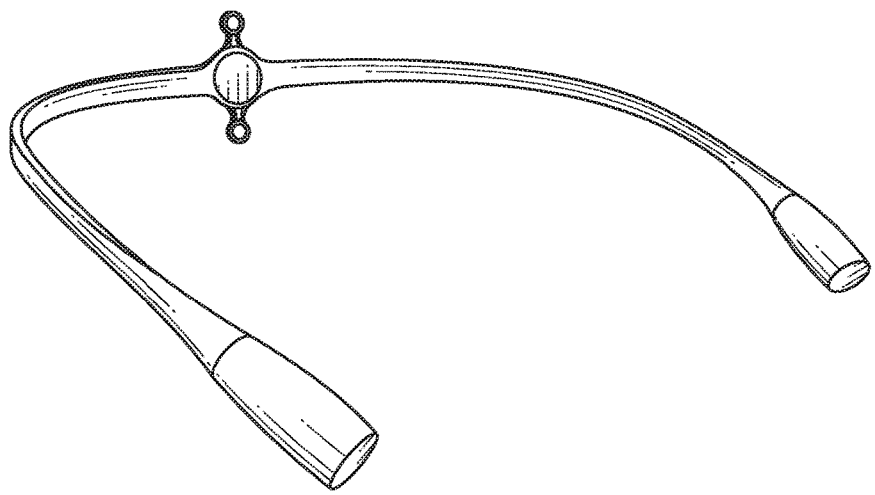
Figure 24D:
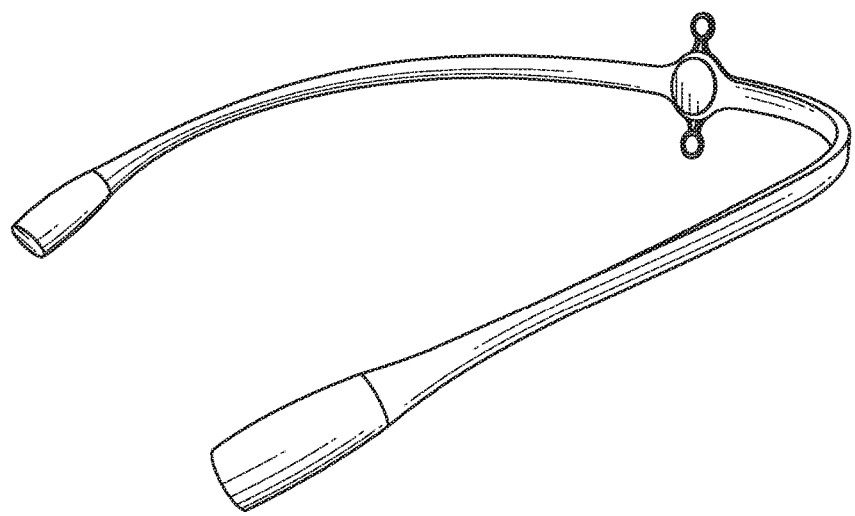

FIGS. 24C and 24D illustrate the overall apparatus shown in FIGS. 24A and 24B. The torc body is semi rigid, and may be worn around the neck pulling apart the ends slightly to fit it over the neck, then pacing it so that middle back region of the apparatus (the electrode-coupling region) may hold the electrodes (arranged above and below the long axis of the torc) coupled against the users bare neck skin. As mentioned, an adhesive material on the electrodes or adjacent region(s) 2422 may help secure it in place. In the Example shown in FIGS. 24A-24D the electrodes are illustrated as somewhat small; larger electrodes may be used for one (e.g., anode or cathode) or both (anode and cathode) electrodes.

Figure 25A:
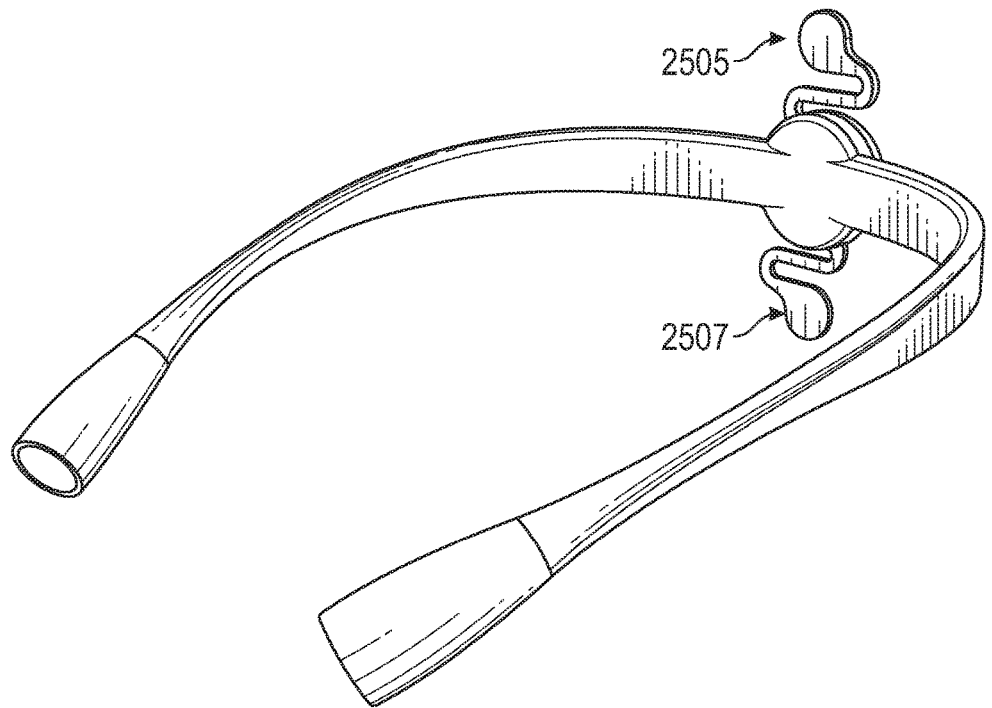
FIGS. 25A and 25B illustrate another example of a neck-worn controller that is rigid or semi-rigid.
Figure 25B:
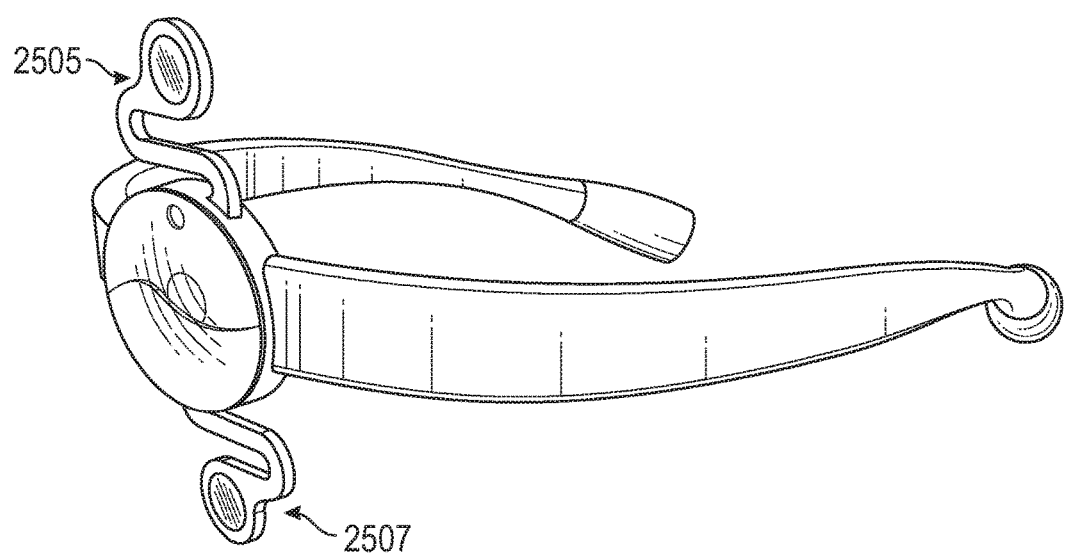

The example device shown in FIGS. 25A and 25B is similar to that illustrated above in FIGS. 24A-24D, however the electrode supports in this example extend from the torc body on electrode support arms 2505, 2507 that may help hold the electrodes against a user's neck in the desired positions.

Figure 26A:
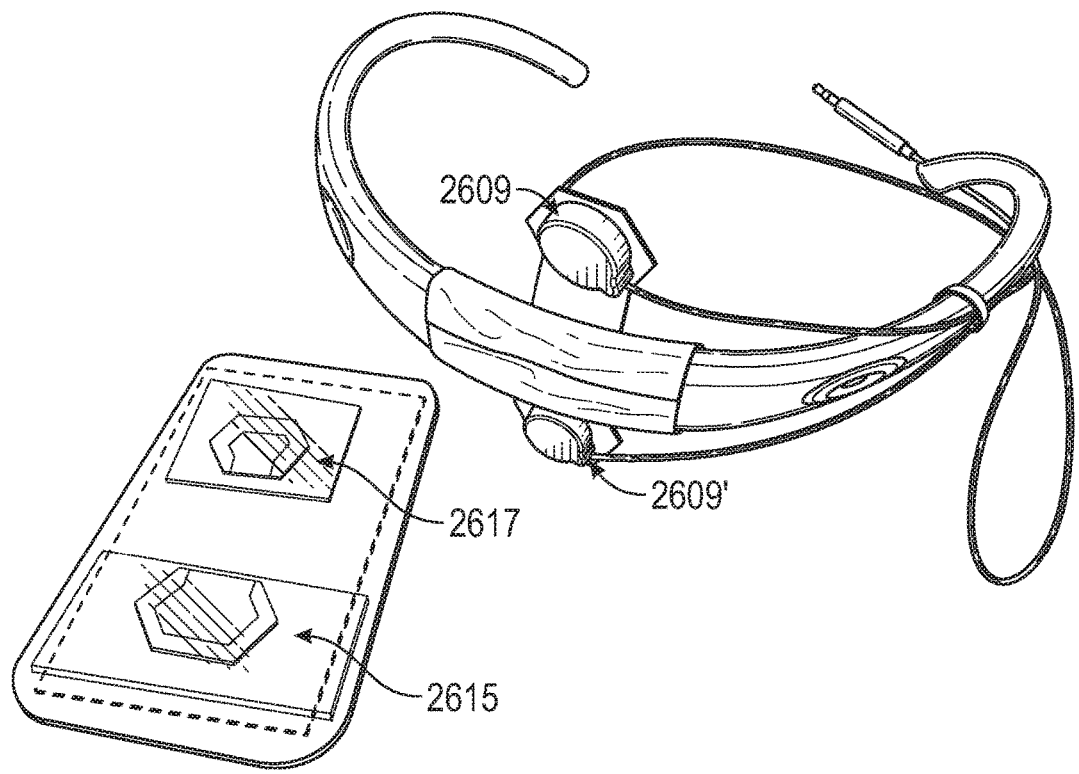
FIGS. 26A-26D illustrates a prototype of a neck-worn TES controller/stimulator as described herein, similar to the variation shown in FIGS. 1C, 16A-18C, and 24A-25B. In this example, the electrodes are shown connected by a wire, e.g., for connection to a user-held/remote electronic device which may include some or all of the control circuitry; this wire connection may be replaced with a wireless connection.
Figure 26B:
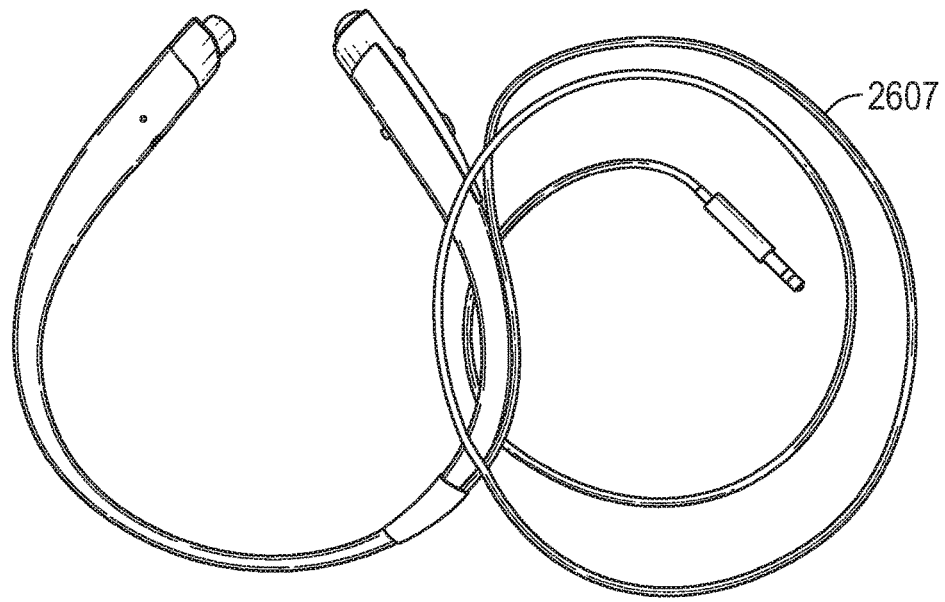
Figure 26C:
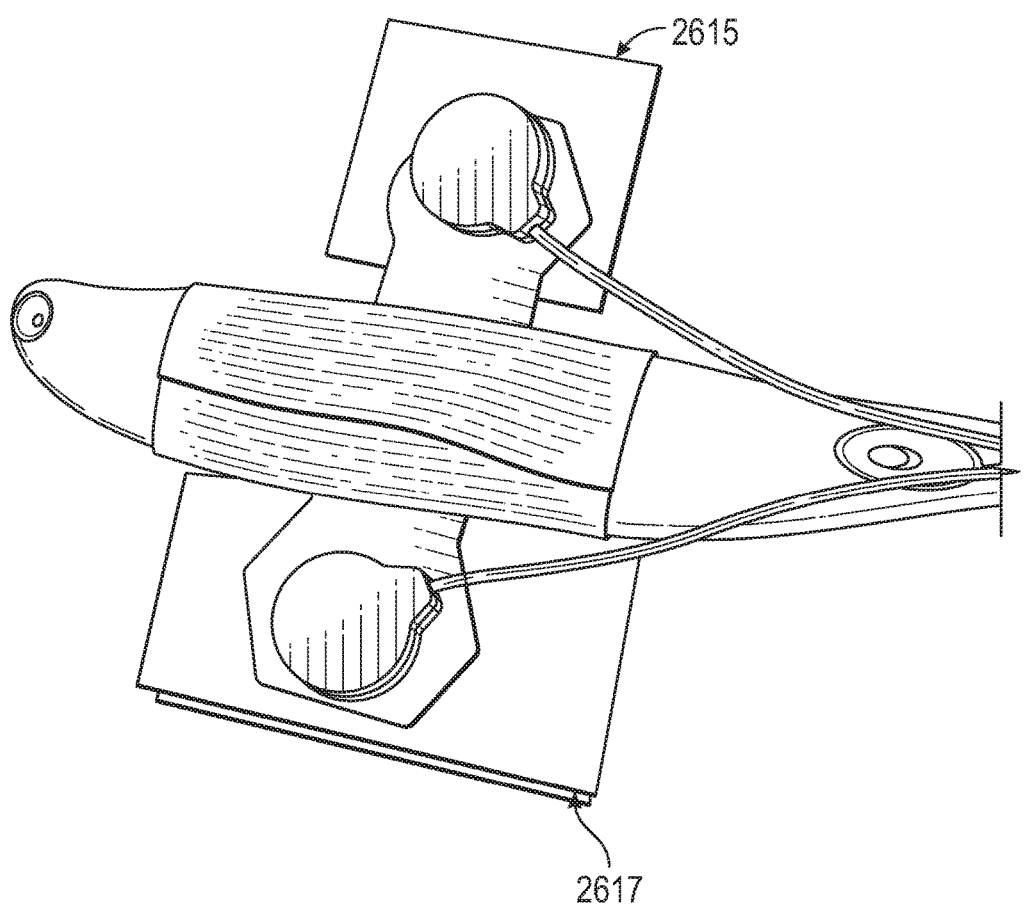
Figure 26D:
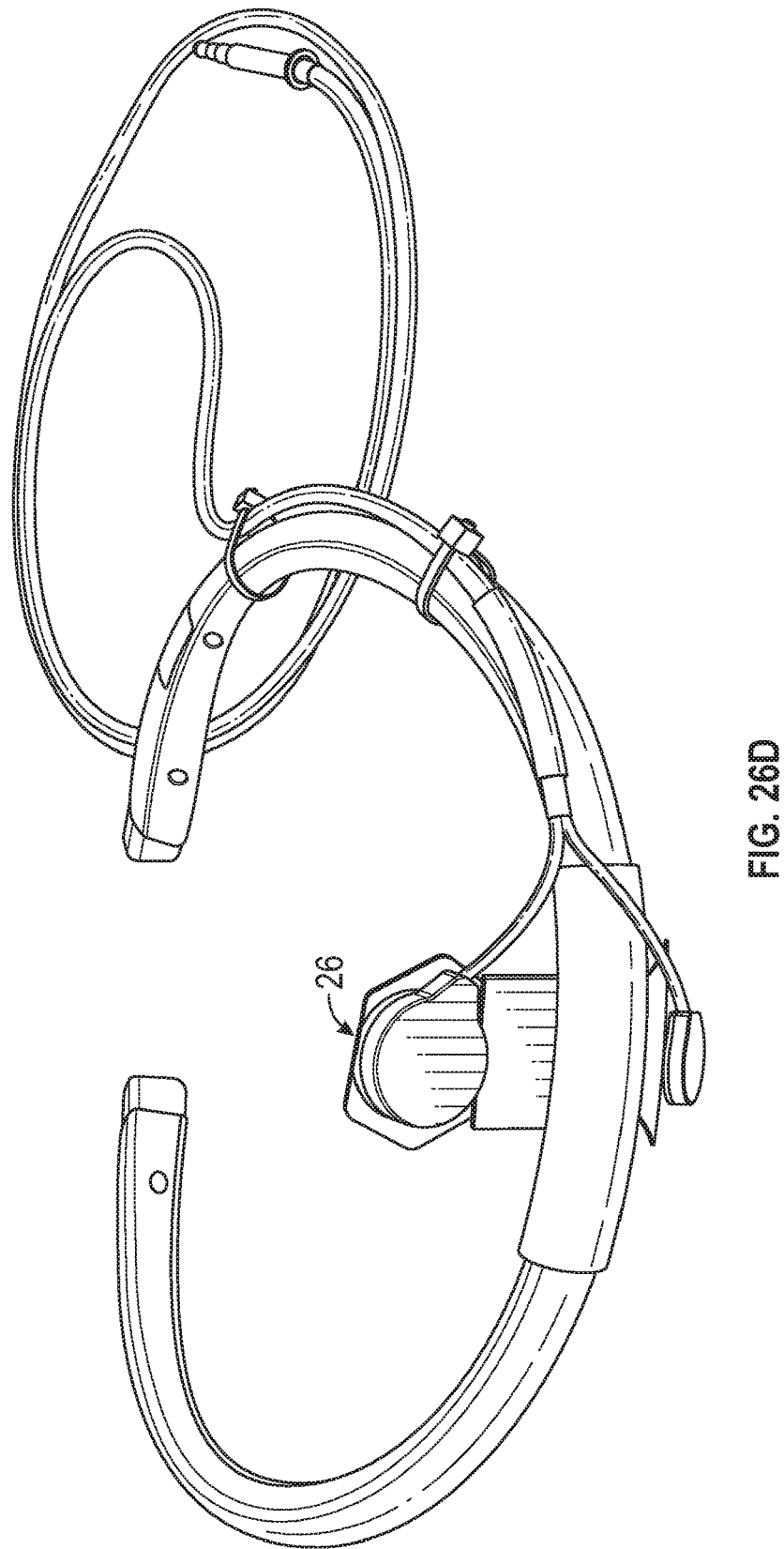

FIGS. 26A-26D illustrate an early prototype device configured for use with a pair of adhesive electrode patches 2615, 2616. These electrodes couple to a controller (not shown) via a cable or cord 2607. The electrodes may be coupled to electrode contacts forming part of each electrode support 2609. FIG. 26C shows a back view of the prototype with rectangular electrode patches 2615, 2617 attached. FIG. 26D shows a similar view without the electrodes attached.

As mentioned, any of the apparatuses described herein may include electrodes (e.g., electrode patches) that couple to the body of the neck-wearable apparatus (neckband, torc, etc.). In some variations the electrode(s) may form part of a cartridge or package that that may include one or more gel pads that connect via adhesion or mechanical contact to couple to the apparatus; these electrodes may be replaced by the user. In practice, this may mean that the apparatus, including electrodes, may be assembled before placing the device on the neck. Alternatively, as mentioned above, the electrodes may be applied to the neck, then coupled (e.g., magnetically) to the neck-wearable body of the apparatus.

One example of a cartridge or electrode assembly that may be coupled to the apparatus may include a double-sided, conductive gel pad with a flood print of silver on carbon PVC film between gel. This film may help buffer the DC reduction and oxidation reactions, as well as help disperse the current. The electrode formed in this manner may then be coupled to the apparatus through an electrical connector in any appropriate manner. In some variations, a gel pad may adhere to one or more conductive contacts on the device made of an inert conductor like carbon, gold or stainless steel contacts. Gel pads may have a backing material to improve handling; and may include a blank space through which contact between the apparatus conductive contact and a gel body is feasible. In some variations the backing material can match the size/shape of the conductive contact to key where the gel body should be placed on the device. The gel body portion of an electrode patch can also be configured as part of a more durable cartridge that needs less frequent replacement. A gel body may or may not be adhesive. If the gel is not adhesive, a secondary material or structure (e.g., bias) may provide or maintain the contact with the users skin. In any of these variations a reusable electrode pad, that may be removed from the body and reapplied later, may include multiple sacrificial adhesive layers. For example, a secondary material may be a single layer or a plurality of layers, whereby removing one exposes fresh layers of underlying materials.

In any of the variations described herein, the device contacts (e.g., electrodes) may be configured to move independent of each other. For example, and upper electrode (or electrode patch) may be adhered to the user; as the user moves their head, the upper electrode may travels with the head differently from the lower electrode, which is attached to a separate part of the head. Alternatively or additionally, the material geometry and/or durometer may allow the electrode patch to differentially contact and expand over its width and length, allowing the different electrodes to move independent of each other and with the users' movements.

Reusable Electrodes

Any of the neck-worn TES apparatuses described herein may include reusable electrodes that are configured to be automatically cleaned (e.g., when inserting into a holder or cartridge, as described herein) and/or self-re-wetting electrodes. FIGS. 27A-27C, 28, 29, 30A-30C, 31, 33A-33B and 34A-34B all illustrate example of self re-wetting electrodes incorporated as part of a neck-worn TES apparatus.

In general, it may be desirable for any of the apparatuses described herein to be "dry" electrodes. A dry electrode becomes conductive when moistened, e.g., with droplets of saline solution. Dry electrodes may be easier to store and use, and may be used without leaving adhesive residue on the skin. As mentioned, any of the apparatuses described herein may be configured for use with dry (also referred to herein as "self re-wetting" or simply "self-wetting") electrodes. In particular, described herein are electrodes and apparatuses including such electrodes that may be wetted (automatically or manually) using a vaporizer (mister or source of mist). It may be particularly advantageous to include a source of mist that is based on vibration (e.g., sonic/ultrasonic vibration) using a piezo. For example, as described herein, the TES waveforms found to be effective to invoke the neuromodulator effects desired may a range of frequencies that are also effective for vibrating a piezoelectric transducer to produce a mist.

For example, a piezoelectric ceramic discs operating at the frequency between 100 KHz to 2 MHz is known to create droplets when the piezo disc is immersed in a fluid. In any of the apparatuses described herein, a piezoelectric vaporizer may be included to apply mist (e.g., of saline or other conductive fluid) onto the electrode surface/skin interface (which may be a sponge or the like) either continuously or discretely (in intervals) to maintain the conductive connection between the dry electrode and the subject's skin. The moisture (vapor) applied may be regulated by feedback based on the electrical contact determined between the subject's skin and the electrode and/or one or more other sensors. A piezo driver may require a voltage between 20 Volt to 100 Volt to create the mist.

Any of the apparatuses described herein may include a controller (local controller) for controlling the application of electrical energy to the electrodes. The same controller, or a separate controller, may be used to control the vaporizer in applying vapor to the electrode(s). For example, any of the apparatuses may include a switching power supply that uses a frequency of oscillation between 100 KHz to 2 MHz. To apply vapor to the electrodes, the high frequency from the power supply may be rectified to create DC for waveforms (e.g., ensemble waveforms, TES waveforms) applied to evoke the cognitive effect(s). Power may also be taken from the power supply before rectification, and the voltage applied to a piezo driver (e.g., disc) at a corresponding resonance frequency, causing the disc to vibrate and generate droplets of vapor that may be delivered as conductive material onto the dry electrode. Thus, in some variations the oscillating power source (also referred to as a switching power source) driving the TES waveforms may be adapted for use with the vaporizer, to provide power for the atomizer without additional circuitry or increasing size of the apparatus.

The piezo driver (e.g., disc) can be embedded into the dry electrode, or submersed in a small reservoir built into the apparatus (including the elongate body/torc body of the neck-worn apparatus). For example, in some cases the apparatus may include an ultrasound mist generator having a matrix of laser drilled holes on the center of the piezo (e.g., ceramic disc) that are less than 2 cm in diameter (e.g., between about 0.5 mm and 2 cm, between about 0.5 mm and 1 cm, between about 0.5 mm and 8 mm, between about 0.5 mm and 7 mm, between about 0.5 mm and 5 mm, between about 0.5 mm and 3 mm, between about 0.5 mm and 2 mm, between about 0.5 mm and 1 mm, etc.); the piezo may be thin (e.g., between 0.5 mm and 5 mm thick, between 0.5 mm and 4 mm, between about 0.5 mm and 3 mm, between about 0.5 mm and 2 mm, etc.). In operation, fluid may be wicked from the bottom side of the piezo through the holes, and then may be atomized by the ultrasound vibration on the "air side" of the piezo.

In some example of self-rewetting electrodes as described herein, an embed ultrasound transducer may be posited behind a gel (or sponge) contacting the electrode (forming the skin-contacting surface of the electrode). The skin-contacting surface may be in a dry state during storage. When a gel is used, the gel may be a matrix that absorbs fluid (e.g., saline) when the mist is applied, but may dry out completely or near completely after vapor is no longer applied.

Figure 32:
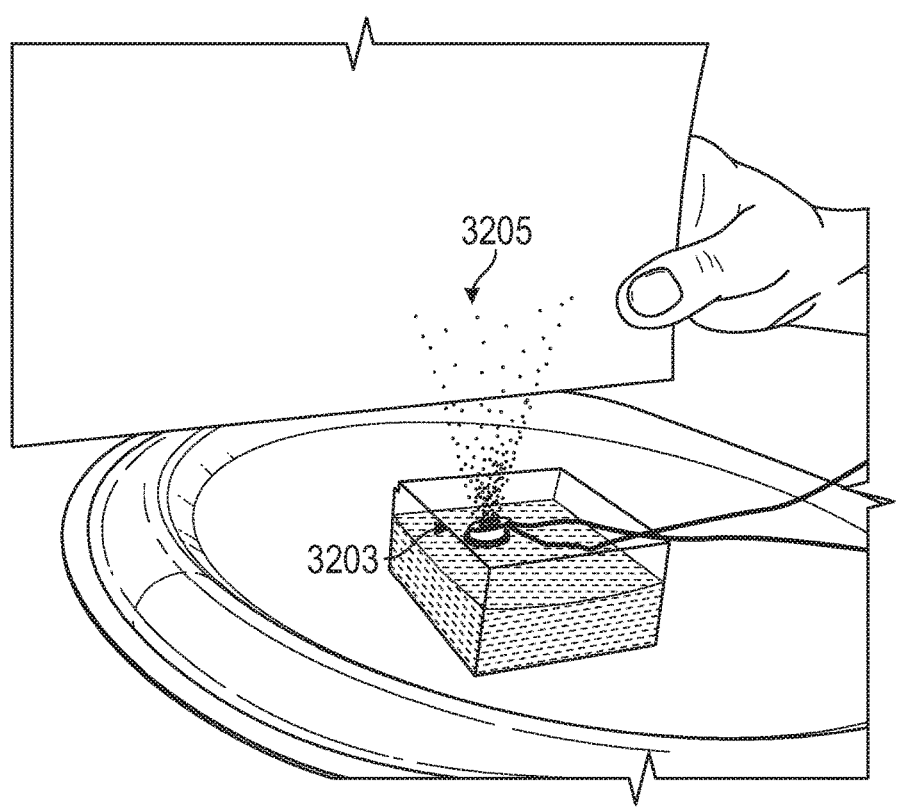
FIG. 32 is an example of a self-re-wetting electrode that may be used in any of the apparatuses described herein, including in particular the neck-worn TES controller/stimulators.

FIG. 32 illustrates a prototype of a vaporizer that may be used to rewet one or more electrodes when incorporated into any of the apparatuses described herein. In this example, a 1 mm thick ultrasound (piezoelectric) disk 3203 has a 1 cm diameter has later drilled holes through its center. When a high frequency signal (e.g., 190 KHz) is applied to the disc at fairly low power, the disc vibrates and throws droplets of fluid (mist 3205) into air, as illustrated against the dark background. Capillary action then replenishes fluid from the back side of the disc. In practice, only a very small amount of fluid needs to be vaporized (for a brief period of time) to wet an electrode. For example, in the example shown in FIG. 32, once the ultrasound turns on (within 2 second or less (e.g., within 1 second, 0.8 second, 0.7 seconds, 0.6 seconds, 0.5 seconds, 0.4 seconds, etc. or less), the electrode is sufficiently wet and makes the appropriate electrical connection to skin. The holes through the piezo material (e.g., disk) may be small enough so that fluid will not spill from the reservoir.

As previously mentioned, although the examples provided here may include such self-wetting electrodes as part of TES apparatus as described herein, in general such self-rewetting electrodes may be incorporated into any apparatus that uses a skin-contacting electrode, including wearable electronics in general (for either or both sensing and stimulation).

In implanting the self-rewetting electrode a fluid reservoir including an electrically conductive fluid (e.g., saline) may be included in the apparatus (including as part of a cartridge or refillable (e.g., by user). The reservoir may be included as part of the wearable (e.g., the elongate body, such as the electrode-coupling region, etc.). The vaporizer (the piezo material) may be on the apparatus, including in contact with the electrode, and particularly the skin-contacting surface of the electrode and/or it may be separate and positioned to direct the stream of vapor on the users skin and/or directly onto the skin-contacting surface. In some variations the vaporizer is behind, beside, surrounding or surrounded by the electrode.

Figure 28:
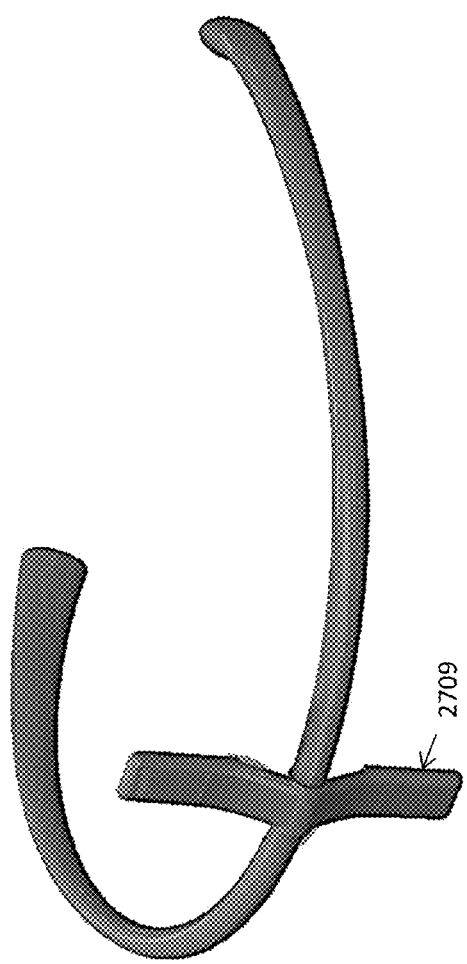
FIG. 28 is a back perspective view of a neck-worn TES controller/stimulator such as the one shown in FIGS. 27A-27C without the reusable electrode contacts.

Alternatively or additionally, a re-wettable and/or cleanable electrode may include a storage compartment the holds, rewets and/or cleans the electrodes between uses. For example, FIGS. 27A-27C illustrate one example of a neck-worn TES apparatus that includes a pair of electrodes coupled to an electrode support (permanently or removably). The electrodes 2705, 2707 in this variation may be folded together, as shown in FIG. 27A, so that they can be placed in a storage compartment when not in use. The storage compartment may clean and/or rewet the electrode surfaces (skin contacting surfaces) which may include a gel and/or sponge as mentioned. Thus in this example the torc body 2703 includes a hinge region 2709 or couples to the hinge region. The electrodes may open outwards, as shown in FIGS. 27B and 27C. In some variations the electrodes may be removable, as shown in FIG. 28, leaving the hinge region 2709 to which new, refurbished, or the original electrodes may again be attached/coupled.

Figure 29:
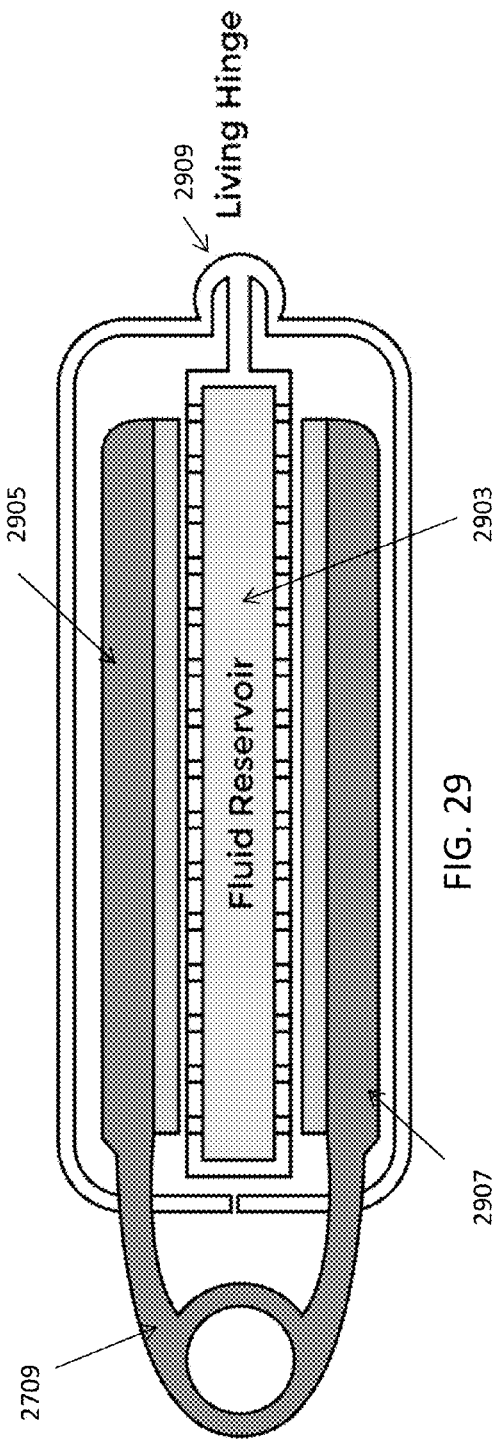
FIG. 29 is a schematic illustration of an example through the self-cleaning and self-rewetting electrodes in an electrode storage/recharging chamber.
Figure 30:
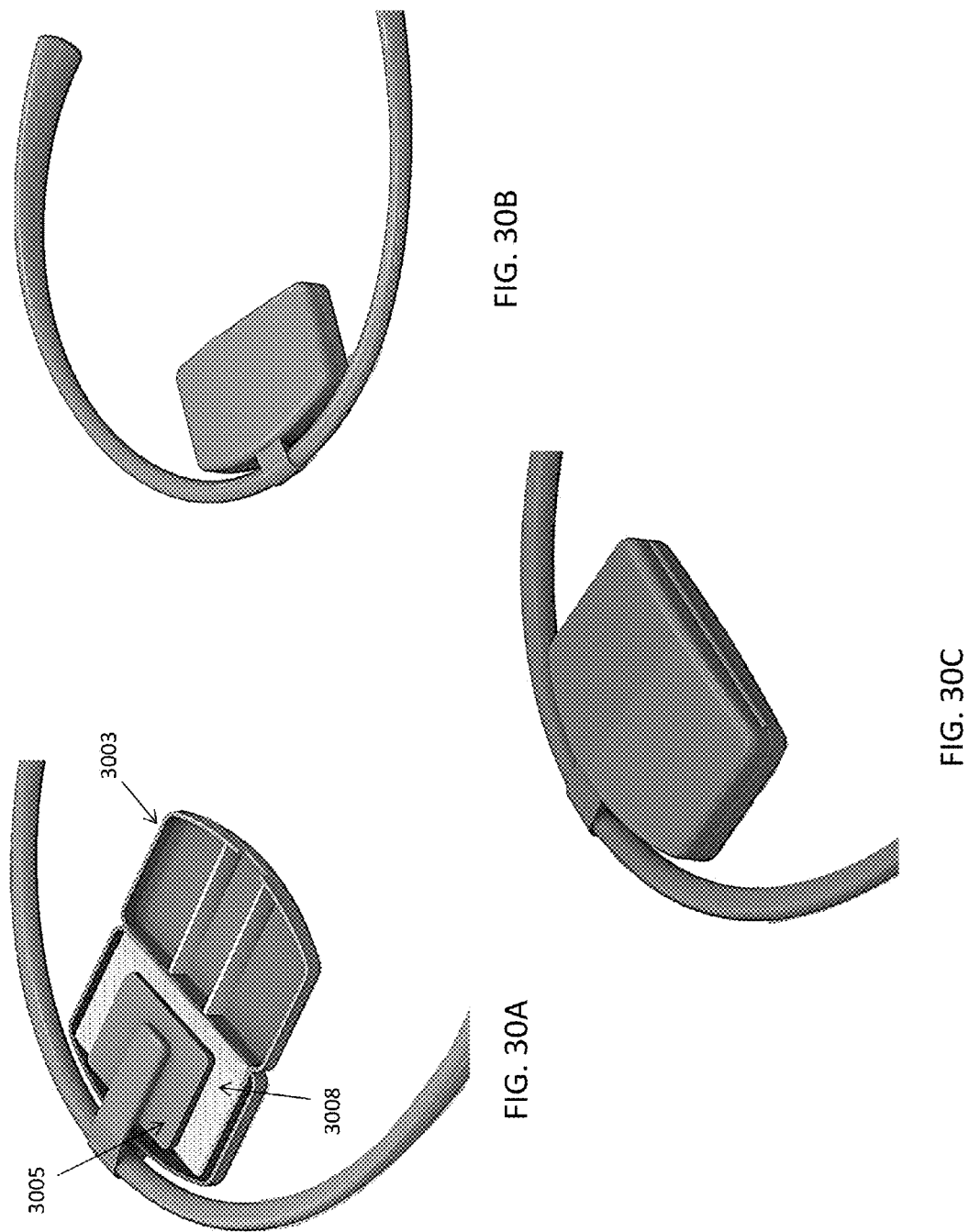
FIGS. 30A-30C illustrate a neck-worn TES controller/stimulator such as the one shown in FIGS. 27A-27C within an electrode storage/recharging chamber (or cartridge) such.

As shown in FIGS. 30A-30C, in variations such as the ones shown in FIG. 27A-27C, the electrodes may be placed and held in a chamber that can rewet them between uses. In FIG. 29, a cross-section of the electrodes 2905, 2907 held within an example of a rewetting cartridge are shown. In this example, the rewetting cartridge includes a fluid reservoir 2903 (e.g., full of saline or another conductive fluid). When not in use, the rewetting cartridge may be placed over the electrodes. In some variations the cartridge may also be configured to clean the skin-contacting surfaces, e.g., during the process of inserting the electrodes into/out of the cartridge.

Figure 31:
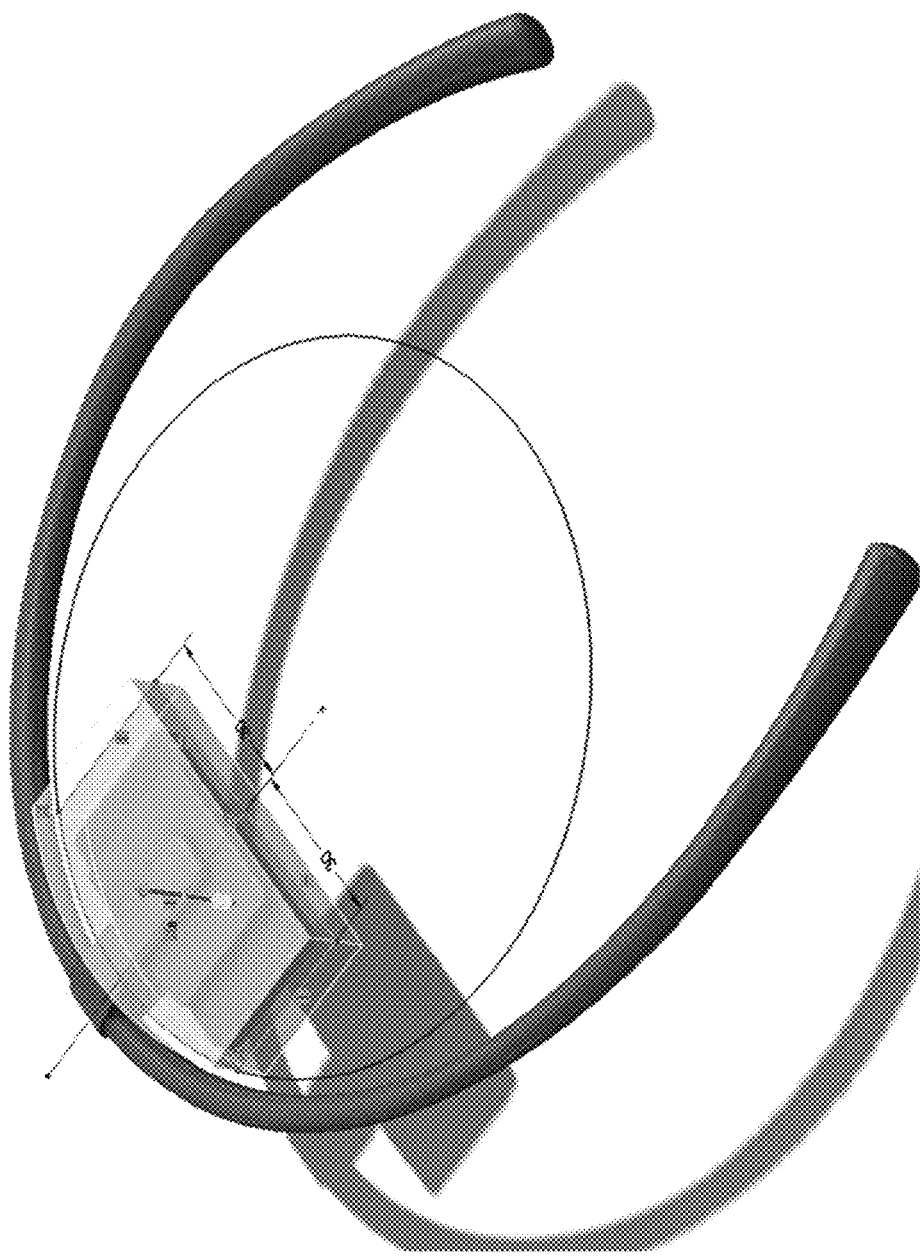
FIG. 31 is a schematic view of the storage/cleaning chamber over a neck-worn TES controller/stimulator such as the one shown in FIGS. 27A-27C.

FIG. 30A shows an example of a pair of electrodes (only one is visible 3005 in this example) held within a cartridge 3003. The cartridge folds over the electrodes, placing their skin-contacting surfaces in contact with a wicking material 3008 (e.g., fiber, sponge, etc.) that is wetted by the fluid reservoir. In this example, the cartridge includes a pair of doors that can fasten over the electrodes, as shown in FIGS. 30B and 30C. When stored in the cartridge, the electrodes are wetted by the apparatus. In some variations the cartridge may include a vaporizer such as those described above, for applying fluid to the skin-contacting surface(s) of the electrodes. FIG. 31 shows a schematic illustration, including exemplary dimensions (in mm), of a rewetting cartridge.

In some variations, the apparatus may be used with a stand. For example, the rewetting cartridge may be configured as a stand; alternatively, the stand may be used to clean and store the electrodes and protect the electrode surfaces when not in use. In some variations the stand may include refilling (e.g., of conductive fluid) and/or recharging (e.g., of battery) between uses.

Figure 33A:
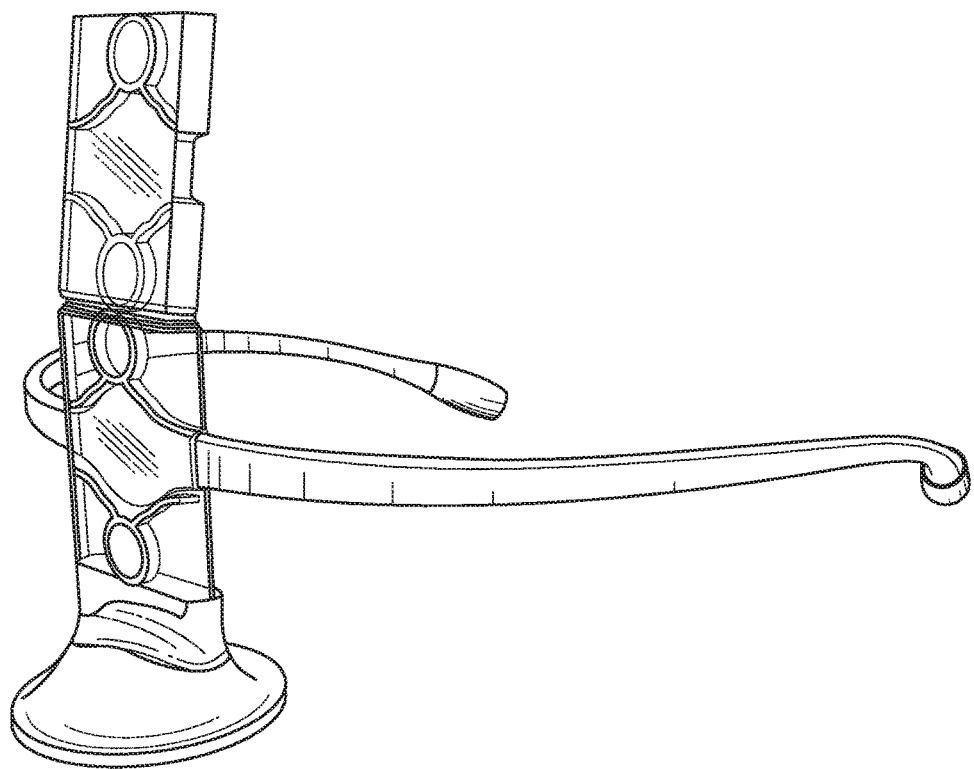
FIGS. 33A and 33B show an example of a clam shell cartridge that is also a stand that may be used with any of the apparatuses (e.g., the neck-worn TES controller/stimulators) described herein. Similar to the storage/recharging chamber shown in FIGS. 30A-31, the cartridge may rehydrate the reusable electrode pads.
Figure 33B:
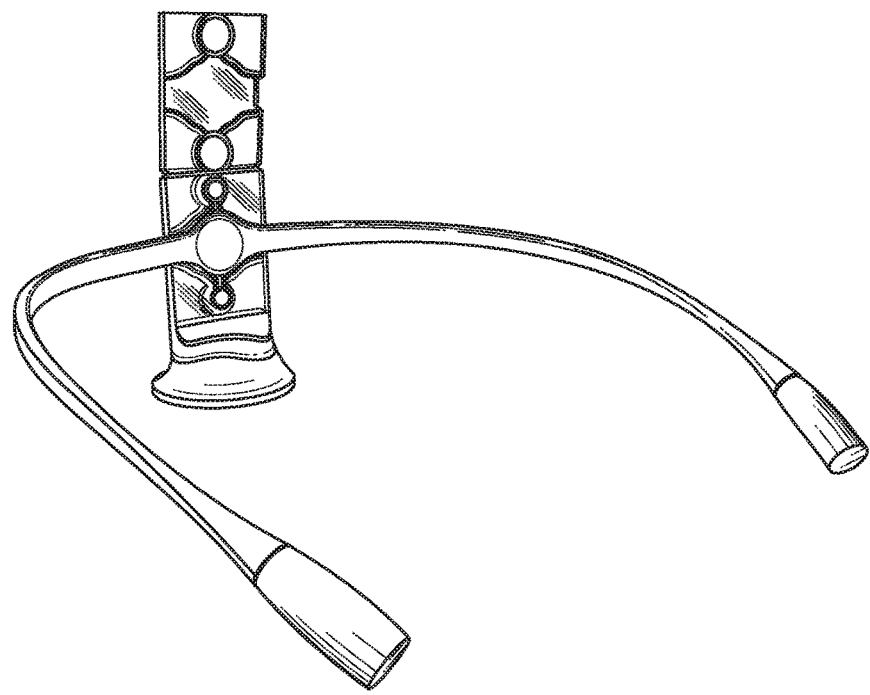
Figure 34A:
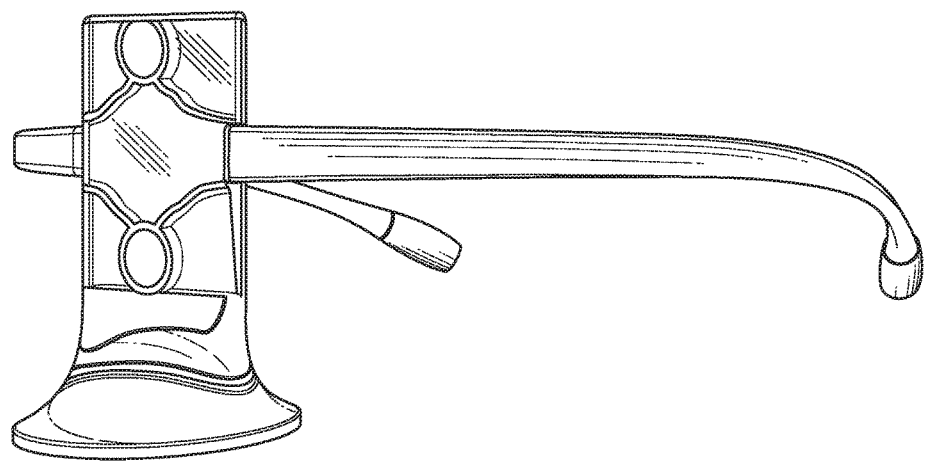
FIGS. 34A and 34B illustrate the storage/recharging chamber of FIGS. 33A and 33B with the chamber closed over the reusable electrodes of the neck-worn TES controller/stimulator.
Figure 34B:
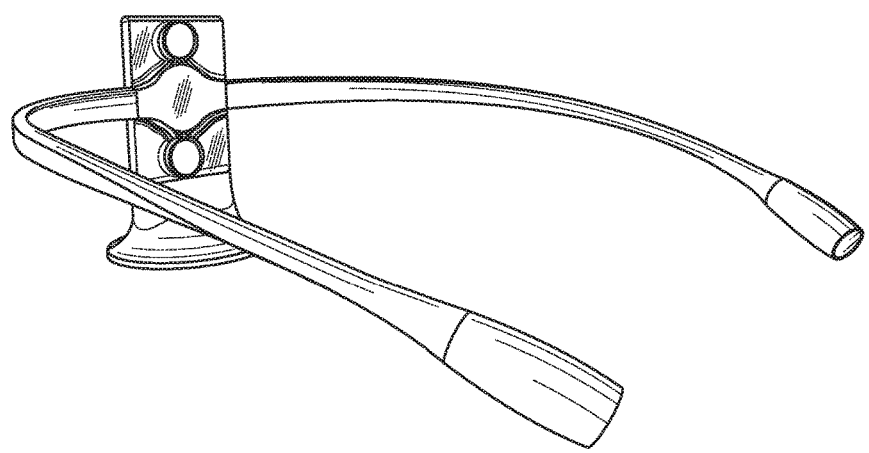

For example, FIGS. 33A-33B and 34A-34B illustrate one example of a stand that may be used. In FIG. 33A, the stand is also configured as a cartridge having a clam shell configuration. The electrodes in this example may be small (larger electrodes may be used). When the stand/cartridge is closed, the materials that touch the electrodes may rehydrate and/or clean them. The cartridge is shown open in FIGS. 33A (back) and 33B (front), allowing the device to be inserted therein. In FIGS. 34A and 34B, the apparatus is inserted into the cartridge and the cartridge is shown as closed, with the hinged door shut so that the electrodes and a portion of the elongate (torc) body held therein.

Neck Placement

Figure 35:
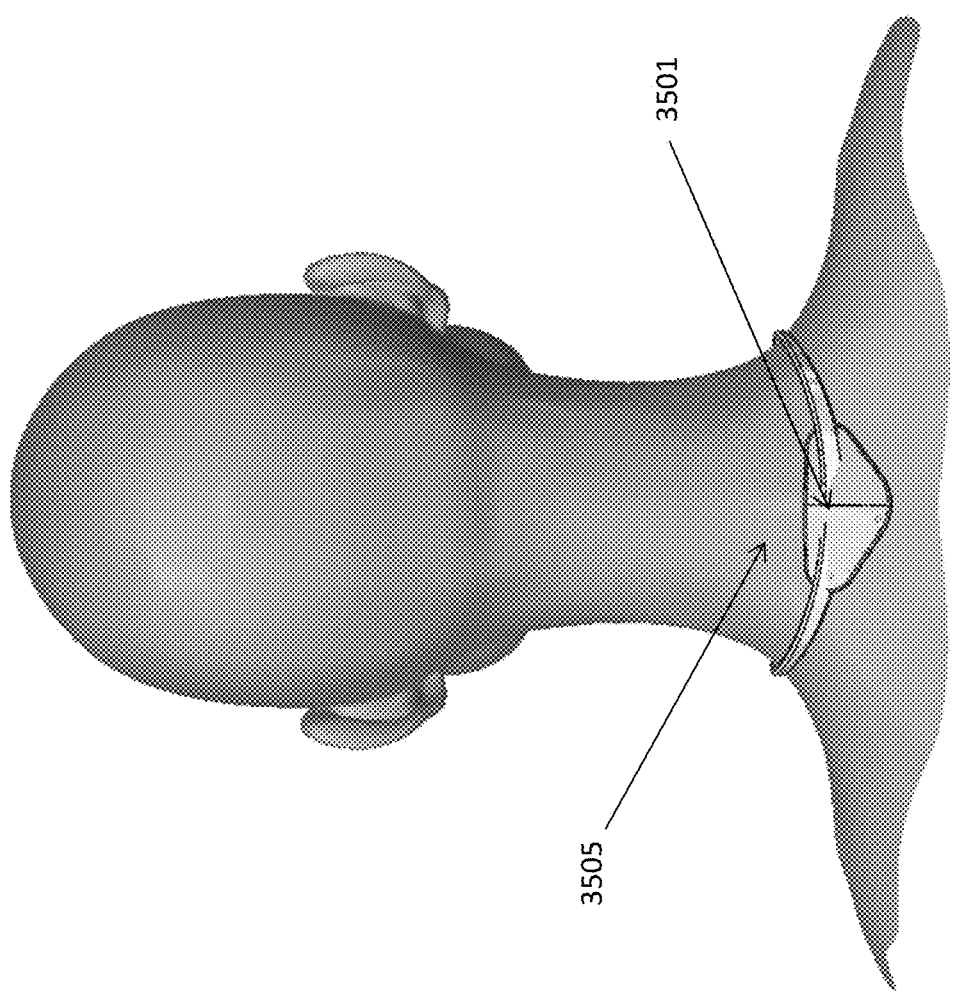
FIG. 35 illustrates an example of subject (user) wearing a neck-worn TES controller/stimulator.

In any of the apparatuses described herein, as shown and described above, the apparatuses may be positioned so that the electrode(s) contact the user (e.g., subject) behind the neck. Both electrodes may be positioned behind the neck. FIG. 35 illustrates an example of an apparatus 3501 worn on a user's neck/back 3505. In general, these electrodes may be positioned along the cervical region and/or the upper thoracic locations e.g., C1-C7 and T1-T2. For example, in some variations the electrodes contact the user with a first (upper, e.g., anode) at C4/C5 and a second (lower, e.g., cathode) at C7 (referring to the locations over the user's skin above corresponding cervical regions C4/C5 and C7).

In some variations the lower electrode may be positioned on the skin over the upper thoracic region of the spine; the upper electrode may also be positioned over the upper thoracic region or in the lower cervical region. For example, FIGS. 37A-37C illustrate variations with this positioning. In FIG. 37A, the pair of electrodes includes a first electrode 3701 in which the upper electrode is within the lower cervical region (e.g., on the skin over the C4-C6 region of the spine), while the second electrode 3703 is also over the lower cervical region of the spine (e.g., on the skin over the C3-C7 region of the spine). More preferably, as shown in FIG. 37B, the upper electrode 3701 is positioned over the lower cervical region (e.g., C6-C7) while the lower electrode 3703 is positioned at the top of the thoracic region (e.g., T1-T2). In FIGS. 37A-37B, the division between the cervical and thoracic region is approximately shown by dashed line 3705. The upper and lower electrodes may be part of an electrode pad that is separate from or integral with the TES controller device.

In general, in any of the methods and apparatuses described herein, it may be beneficial for the electrodes to be arranged so that the first electrode is above the second electrode when worn on the body along the subject's anterior-to-posterior (e.g. foot-to-head) longitudinal midline at the back of the neck/upper back. The separation between the first and second electrodes may also be important. For example, the separation may be between 0.7 inches and 2 inches, preferably between 0.8 inches and 1.4 inches. The minimum distance may be between 0.7 and 1.2 inches (e.g., approximately 1 inch), from the nearest edge to the nearest edge. The maximum distance may be between 1.7 inches and 2.2 inches (e.g., 2 inches) from nearest edge to nearest edge. For example, as shown in FIG. 37A, the electrodes may be separated 3709 by an approximately 0.8-1.5 inch distance (nearest edge to nearest edge) and arranged in an anterior to posterior (e.g. foot to head) longitudinal direction, so that the electrodes are stacked atop each other relative in the longitudinal axis.

FIG. 37C illustrates an example of an arrangement of the electrodes in which the upper electrode is on the skin over the cervical region while the lower electrode is on the skin over the thoracic region of the spine, similar to FIG. 37B, however the separation 3709' between the electrodes (nearest edge to nearest edge) is closer to 2 inches (e.g., between 1.8 and 2.2 inches). In general, the minimum distance between the electrodes may provide field penetration of sufficient depth so that the energy is not simply shunted across the subject's skin. Without being bound to a particular theory of operation, this may allow stimulation of the cervical nerves. However, if the electrodes are too far apart, the energy applied may be too diffuse or may require a larger output energy. Surprisingly, having the electrodes separated by approximately 1 inch (nearest edge to nearest edge) works, and indeed works particularly well.

In addition, maintaining the electrodes in this region of the neck (or neck and back), so that the pair of electrodes are positioned on the skin over the lower cervical/upper thoracic region is surprisingly more comfortable and effective than placement in other regions, particularly other neck and/or head regions. In this configuration at least one of the electrodes (e.g., the lower electrode) may be highly stable, even while the subject moves his or her neck and head, preventing discomfort and avoiding dislodging the apparatus The anode and cathode electrodes may be arranged in any orientation (e.g., vertically relative to the long axis of the user's body, horizontally, etc.). In some variations it may be beneficial for the electrodes to be arranged vertically relative to the long-axis of the user's body (e.g., from the head to the feet). For example, the electrodes may be arranged with the electrodes vertically aligned, one on top of the other. Surprisingly, in some configurations parallel vertical strips covering the area do not seem to work as well. One preferred placement may be to place the anode at the base of the neck (e.g., versus just below the hairline) and the cathode downward from there, correspondingly to the top of the back. This arrangement may provide optimal effect (e.g., cognitive effect, while minimizing discomfort).

Figure 36A:
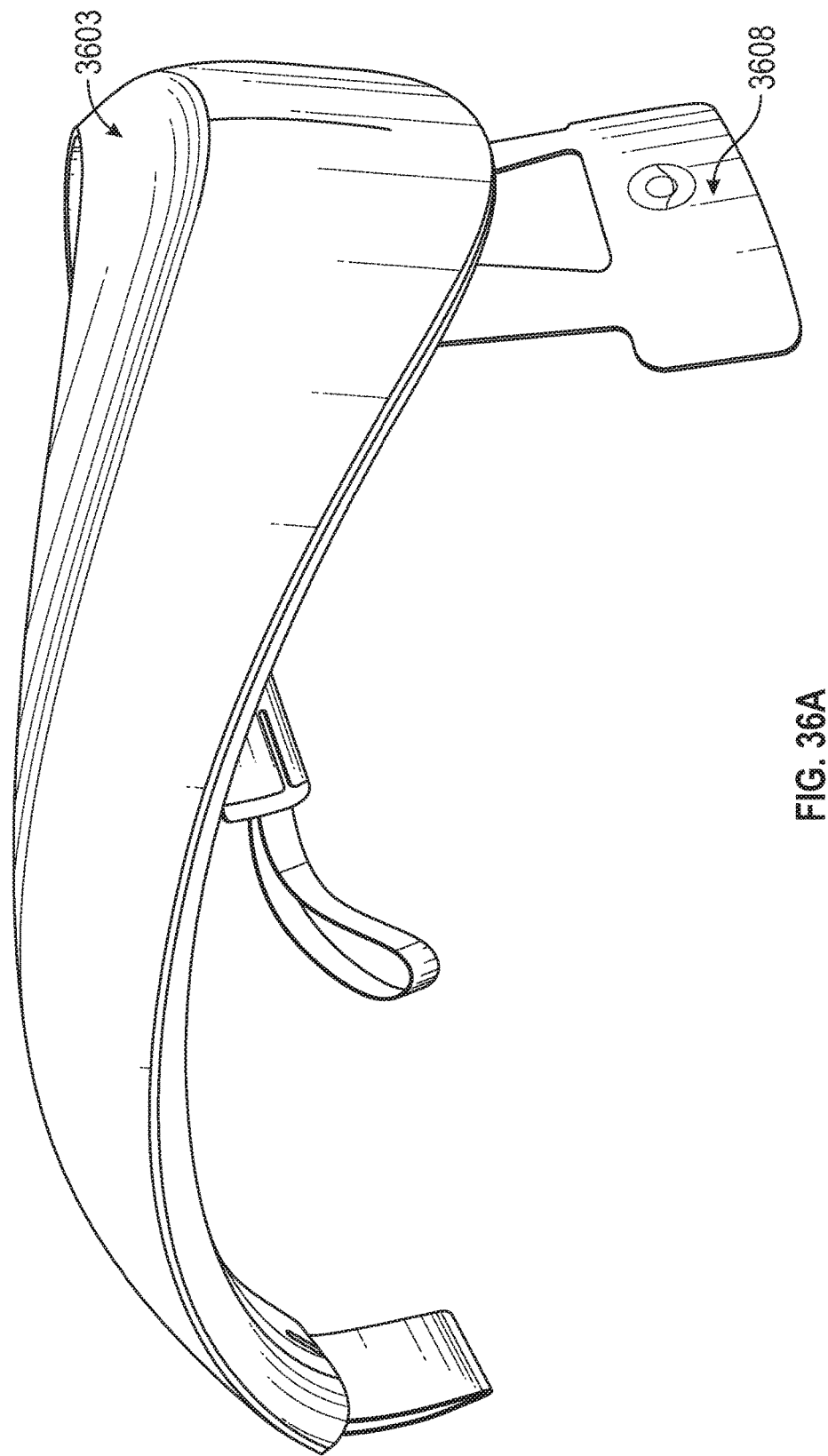
FIGS. 36A-36D illustrate another example of a neck-worn TES controller stimulator as described herein.
Figure 36B:
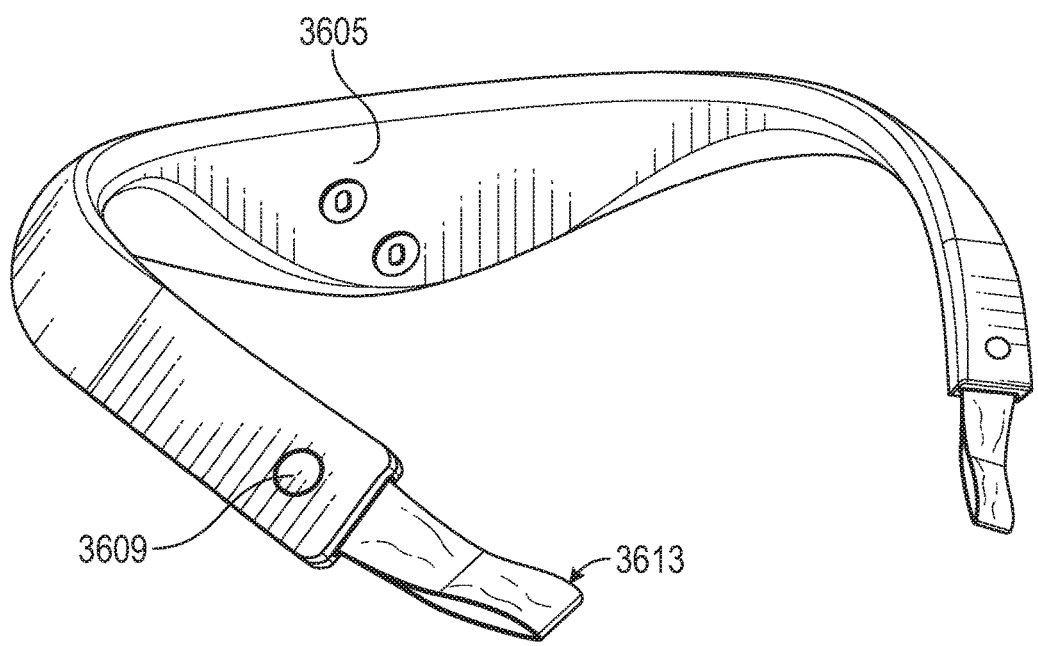

FIGS. 36A-36D illustrate another example of a neck-worn TES apparatus that may be used as described herein. In this example, the TES apparatus includes a rigid or semi-rigid frame 3603. In some variations the frame may be formed of a polymeric material, such as a plastic material, including metallized plastics. The inner surface of the frame may be padded, covered, coated, etc. for wearing comfort. For example, the inner (user-facing) surface may be wrapped or covered with a fabric 3605. One or more electrodes, or attachments/connectors for a disposable electrode (e.g., strip, pad, contact strip, etc.) may be present on the inner surface as shown in FIG. 36B, or it may be present inside of the surface, or on an outer surface, and the pad may extend down/up from the wearable body. FIG. 36A illustrates an example of an electrode strip/pad 3608 extending from the wearable body. The strip or pad may be snapped or otherwise coupled to the wearable body. In FIG. 36B the inner surface of the body shows a pair of offset connectors for coupling (in this example, snap-fitting) to the pad. The electrodes 3608 may be held against the skin (e.g., adhesively or simply by virtue of the connection to the weight of the wearable body). The body 3603 may also be textured on the outer, inner, or both surfaces (e.g., an in-mold texture on plastic in this example). In some variations the connections to the electrodes may be present within the housing 3603, which may include a slot, clamp, or the like to hold the electrode connectors and make connection thereto. Alternatively, as described above, the electrodes may be reusable, durable electrodes that are coupled to and/or extend from the wearable body.

In FIG. 36B the wearable body also includes at least one control (e.g., power button 3609) on the body. Additional controls (buttons, sliders, switches, etc.) may be included; alternatively no buttons may be present on the surface, but it may be powered on/off remotely and/or controlled remotely, e.g., by a wireless apparatus such as a smartphone running control software.

Figure 36C:
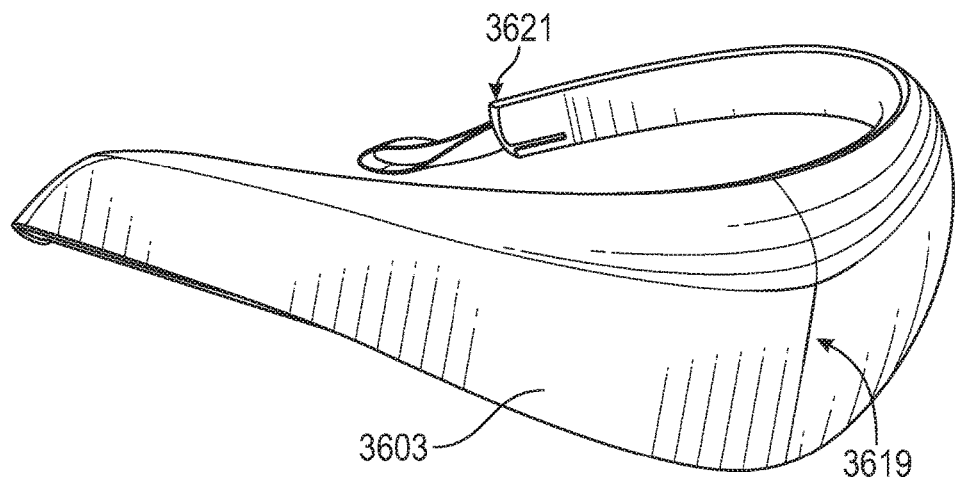
Figure 36D:
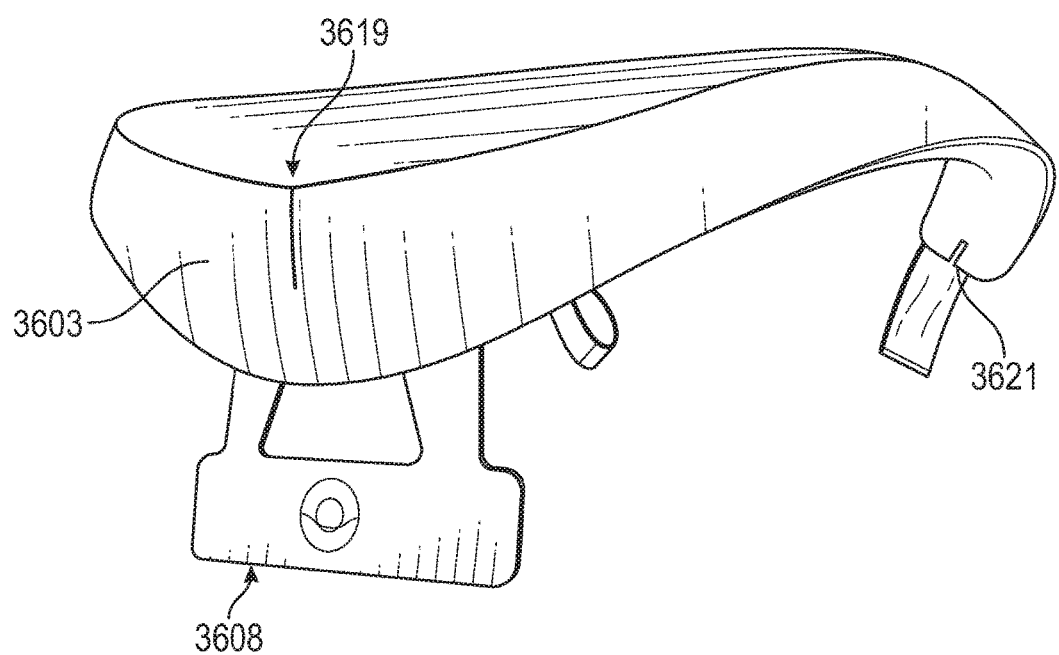

The apparatus of FIGS. 36A-36D includes one or more straps 3613 (e.g., nylon straps 3611) that may be present at the ends of the torque-shaped neck worn body and may be used to attach to an additional component (e.g., leash, etc.) or may be configured to attach to clothing or jewelry. The ends of the arms of the wearable body may be metallic (e.g., may include metallic endcaps 3621, as shown in FIG. 36C). In FIGS. 36C-36D the wearable body may also include one or more indicator light regions 3619 which may be illuminated by one or more (including different color, intensity, etc.) light sources, such as LEDs.

Adapter Electrode Pads

Although many of the apparatuses and methods described herein are configured so that the controller (or stimulator or controller/stimulator) apparatus for applying transdermal electrical stimulation (TES) to the back of a subject's neck to modify a user's cognitive state (e.g., to induce a relaxed state) includes a wearable torc body that extends around the subject's neck, these techniques may be configured so that the controller apparatus is a small, lightweight and wearable apparatus that does not extend around the neck. For example, any of the TES stimulator apparatuses described in the following patent applications (herein incorporated by reference in their entirety) may be adapted for use in neck (and particularly C3-T2 neck/back) only stimulation: US-2014-0148872; US-2015-0088224; US-2016-0008632; US-2015-0005840; US-2015-0005841; US-2015-0174403; US-2015-0238762; US-2016-0317809; US-2015-0035877; US-2015-0335876; US-2016-0346545; US-2015-0335875; US-2015-0335888; US-2015-0328461; US-2015-0328467; US-2016-0346530; and US-2017-0076414. The apparatuses described therein typically include a wearable portion that couples to an electrode (often referred to as a cantilever electrode) and generally connect between the subject's forehead and a location on the back of the subject's neck or behind the ear. Thus, these TES controller devices are configured to couple with an electrode pad on the temple region of the subject's head, and may be adapted to have a body shape that is well suited for this location. Described herein are electrode pads (referred to as adapter electrode pads) that are configured to apply the TES to the C3-T2 neck/back region of the skin which have surprisingly been found to be both comfortable and effective, even as compared to the application at the head and neck.

For example, FIGS. 38A-38B illustrate the use of an adapter electrode pad 3801 (also referred to herein as a neck-only electrode pad) that is configured to be worn over the C3-T2 spinal region on the skin, in which the closest-edge to closest-edge separation between the first and second electrode of the pair of electrodes is separated by between 0.8 inches and 2.5 inches (e.g., 0.8 inches and 1.6 inches). In this example, the adapter electrode pad 3801 is placed on the skin over the C3-T2 region of the spine, so that the electrodes are arranged in the midline of the back/neck in the longitudinal anterior-to-posterior axis, with the lower electrode over the C5-T2 region. This is shown in FIG. 38A. In this example, the adapter electrode pad includes a pair of male connectors, shown configured as snaps having protrusions which mate with female connectors on a TES controller device 3803, providing mechanical and electrical connection. The TES controlling device may be a lightweight wearable TES controller device, including those incorporated for reference above, which are otherwise configured to be worn on the subject's head. The adapter electrode pad is therefore configured to adapt these device so that they can be worn on the neck, as shown in FIG. 38B.

Figure 39A:
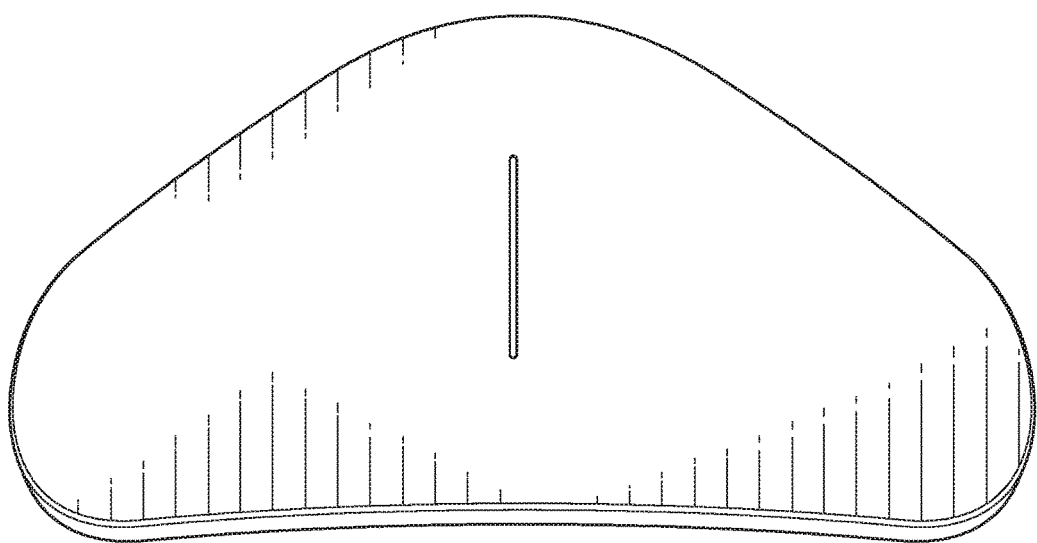
FIGS. 39A-39B show front and back views, respectively, of a controller device for applying transdermal electrical stimulation (TES) to modify a user's cognitive state and induce a relaxed state, such as the device shown attached to the electrode pad adapter in FIG. 38B.
Figure 39B:
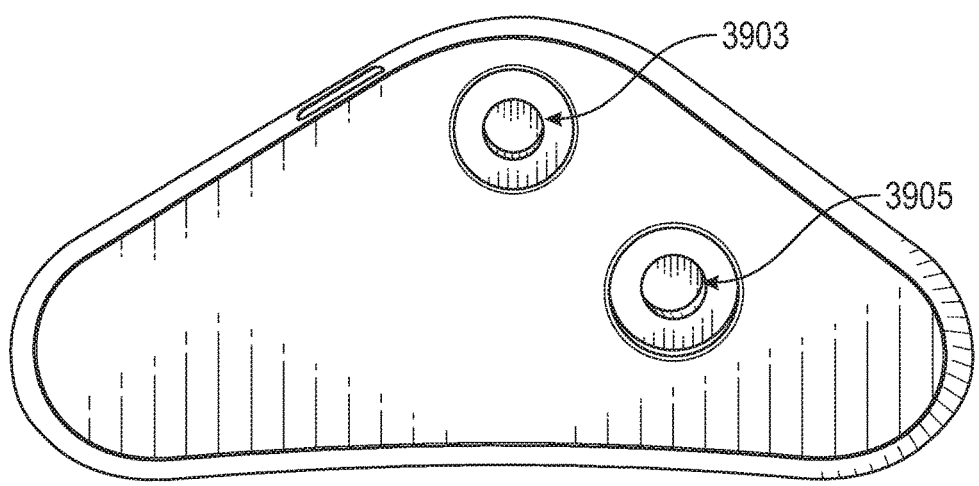

FIGS. 39A-41I illustrate an example of a TES controller device that may be used with the neck-only adapter electrodes pad described herein. FIG. 39A shows the front of a TES controller device that is lightweight and configured to be worn (e.g., on the temple region of the head). FIG. 39B shows a view of the back of the device of FIG. 39A, showing a pair of snap-on connectors 3903, 3905 that provide both mechanical and electrical connection to the adapter electrode pads. In this example, the apparatus body may have two (or more) parts, including a front body shell that mates with a back body shell and encloses the control circuitry (e.g., processor, battery, wireless communications, buttons/inputs, outputs/LEDs and the like). FIGS. 40A-40F illustrate a front body shell, including exemplary dimensions (in mm), and angles). Generally, the body 4001 may be configured to mate with the back body shell. FIGS. 41A-41I illustrate an example of a back body shell 4101 that may attach to the front body shell.

Any of the wearable TES controller devices described herein, including the wearable example shown in FIGS. 39B and 40A-41I, may couple with a neck-only adapter electrode pad. In addition, any of the neck-worn controllers described above, may also be configured to be worn or connected to these adapter electrode pads. FIGS. 42A-42C illustrate an example of a neck-only adapter electrode pad.

In FIG. 42A, the adapter electrode pad includes a pair of connectors 4203, 4205 that are shown as male snap type connectors that may make an mechanical and electrical connection with the TES controller device, as shown in FIG. 38B. The electrode pad is generally flat, and is configured so that it can be flexible, yet provide good contact between an upper electrode 4207 and the skin and a lower electrode 4209. As shown in FIG. 42B, the upper electrode may be separated from the lower electrode (closet edge to closet edge 4211) by between about 0.8 inches and 2.5 inches. In FIG. 42B the distance is approximately 1 inch.

The electrode pad shown in FIGS. 42A-42C are configured for applying transdermal electrical stimulation (TES) to the back of a subject's neck to modify a user's cognitive state. Any of these electrode pads may include a flat substrate 4281; the first (e.g. upper) electrode 4207 on a first side of the flat substrate and a second (e.g., lower) electrode 4209 also on the first side. As mentioned, the closest edge of the first electrode is separated from a closest edge of the second electrode by between 0.8 inches and 2 inches 4211. These electrode pads may also include a first male snap connector 4203 that is electrically connected to the first electrode and extends from the substrate on a second side of the flat substrate that is opposite from the first side. A second male snap connector 4205 electrically connects to the second electrode and extends from the substrate on the second side.

In any of these patches it is surprisingly advantageous, particularly so that the TES controller may fit onto the neck to allow neck bending and head motion, to arrange the first electrode and the second electrode in a first line that is parallel to a longest axis of the electrode pad, and arrange the first male snap connector (or whatever type of connector is used) and the second male snap connector (ow whatever type of connector is used) in a second line that is at an angle of between 25 and 65 degrees relative to the first line (e.g., between 15 and 60 degrees, between 30 and 60 degrees, approximately 45 degrees, etc.). This angled arrangement has surprisingly proven to be particularly helpful in allowing the vertical arrangement of the electrodes on the body (back/neck) while permitting the TES controller/simulator to be worn without impeding movement or irritating the subject (also referred to throughout as the "user").

In any of these variations, the electrode pad may be adhesively held to the skin. For example, the first side may comprise an adhesive. As mentioned, the flat substrate may have a two-lobed (e.g., bi-lobed) shape. The first electrode and the first and second male snap connectors may be on a first lobe of the flat substrate and wherein the second electrode may be on a second lobe of the flat substrate, as shown in FIGS. 42A-42C. The second electrode may extend beyond the perimeter of the flat substrate, as shown. In general, the second electrode may be larger than the first electrode. For example, the surface area of the second electrode may be greater than 1.25 times (e.g., greater than 1.4×, greater than 1.5×, greater than 1.6×, greater than 1.7×, greater than 1.8×, greater than 1.9×, greater than 2×, etc.) the surface area of the first electrode. As mentioned, the closest edge of the first electrode may be separated from the closest edge of the second electrode by between 0.9 and 1.5 inches, preferably around 1 inch.

In this example, the electrode pad is formed from a flexible substrate onto which each electrode is formed by adding layers, as illustrated schematically in FIGS. 43A-44E.

Figure 43C:
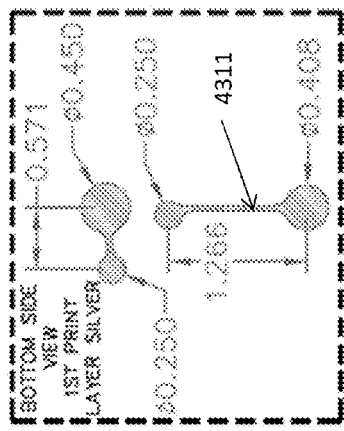
FIGS. 43C-43F illustrate layers the may be formed to make the apparatus of FIG. 43A. For example, the FIG. 43C shows the conductive trace (silver) applied to the device.
Figure 43B:
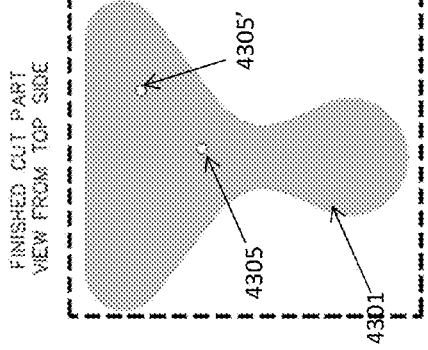
FIG. 43B shows the top view of the connector portion of the adapter of FIG. 43A.
Figure 43A:
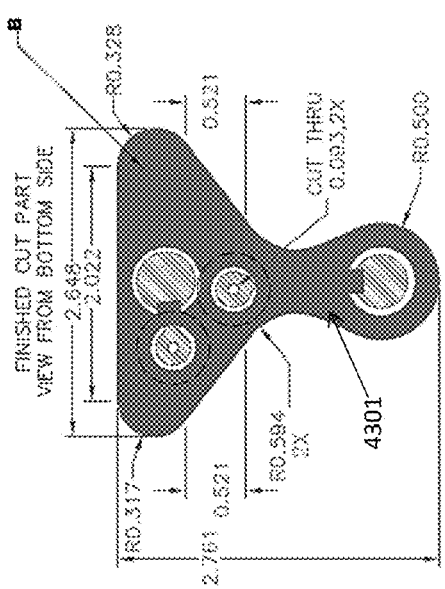
FIG. 43A shows a bottom (skin-contacting) view of an example of a portion of an adapter electrode pad that is configured to be applied to the subject's neck so that a pair of TES electrode pads can be positioned over the cervical and/or thoracic region of the spine. These adapter electrode pads may be referred to as adapters, adapter pads or adapter electrode pads because they may adapt a forehead or temple controller/stimulator TES apparatus, such as the one shown in FIGS. 40A-41I, above, to apply TES to the neck (and particularly the C4-T2 region) only. They may also be referred to as neck-only electrode pads.
Figure 43F:
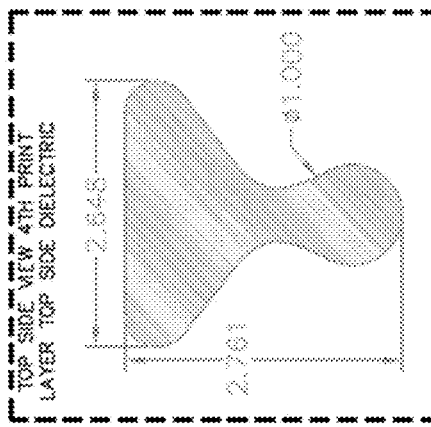
Figure 43E:
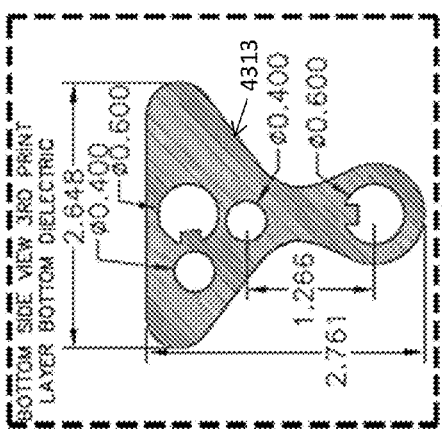
Figure 43D:
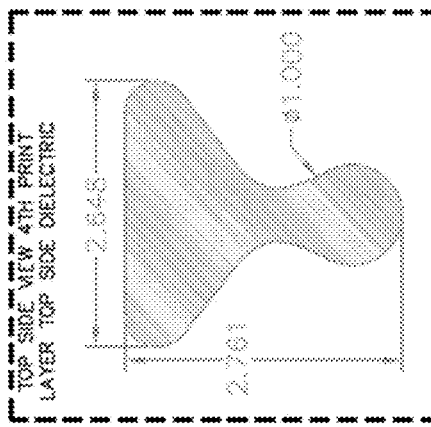

For example, as shown in FIG. 43A, showing a bottom side of the electrode pad substrate for an electrode pad such as that shown in FIGS. 42A-42C, with exemplary dimensions shown, the substrate 4301 is cut into the bi-lobed shape shown (the upper lobe is roughly triangular and the lower lobe is circular); the upper portion includes through-holes 4305 for connecting to the male connectors. The electrical contacts may be formed onto this substrate. The electrical contacts (first and second electrodes, as well as any connecting electrical trace) may be formed by any appropriate means, including screen printing, deposition, etc. FIG. 43B shows the top side of the substrate of the electrode pad. Conductive traces formed of silver 4311 or other conductive material may be printed onto the substrate, as shown in FIG. 43C. A second conductive layer (e.g., carbon) 4312 may be printed over this layer, having a slightly larger perimeter, as shown in FIG. 43D. Finally an insulative (dielectric) layer 4313 may be printed over these, with openings where conductive contacts will be made with the other portions forming the spreading region (and skin-contacting surfaces) of the electrodes, described in reference to FIGS. 44A-44E, below. In addition, a dielectric may be printed over the top layer, as shown in FIG. 43F.

FIG. 44 shows an assembled electrode pad, including a top electrode 4401 and a bottom electrode 4402. A liner 4403 and a liner label 4404 are also shown. As shown in FIG. 44D, the electrodes may be built up of layers. These layers may be formed of a release liner and a silver (conductive) layer and/or a conductive gel (hydrocolloid); and additional adhesive may also be included. FIGS. 44E-44G illustrate similar layers for the second electrode, including a hydrogel layer (2A), a silver/carbon layer (2B), a second hydrogel layer (2C) a foam (2D), and a release liner (2E).

The electrode pad may include text or writing that provides instructions for applying and/or removing the electrode pad, as shown in FIG. 45A-45B. In some variations. This writing may be adhesively applied (4) to the back of the electrode pad.

Figure 46:
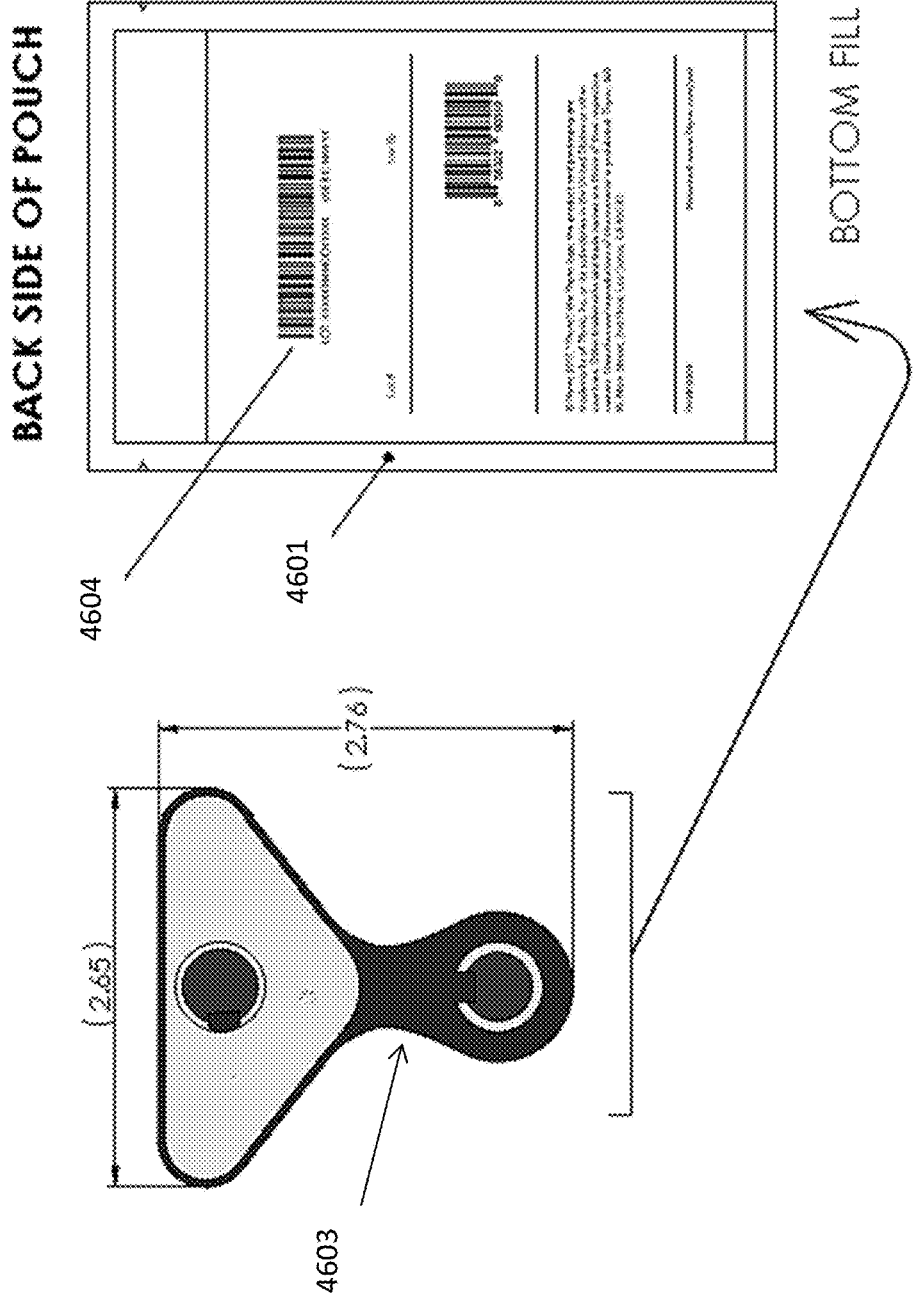
FIG. 46 illustrates a packaging (pouch) for an adapter electrode pad such as the ones shown in FIGS. 42A-45B.

The design of the electrode pads shown in FIGS. 42A-45B may be particularly well suited to manufacturing them in a roll or sheet, as shown in FIG. 45C. To use, the electrodes may be peeled off of the pad, as shown. Alternatively, they may be cut or formed for individual packaging, as shown in FIG. 46, showing a pouch 4601 into which the electrode pad 4603 may be placed. This pouch may be sealed, and marked 4604 including marking with a unique code and/or lot number.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps. In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of applying transdermal electrical stimulation (TES) to the back of a user's neck to induce a relaxed state, the method comprising:
   placing an anode and a cathode along a midline of a back of the user's neck between a region over the user's C3 cervical region and the user's T2 thoracic region, wherein the anode is separated from the cathode by between 0.8 and 2.2 inches;
   applying electrical energy between the anode and the cathode to deliver TES; and
   inducing, in the user, a relaxed state by the application of TES.

2. The method of claim 1, wherein placing comprises adhesively attaching the anode and the cathode.

3. The method of claim 1, wherein placing comprises placing the anode and the cathode so that the anode is separated from the cathode by between 0.8 inches and 2.0 inches, and wherein the anode and the cathode are arranged along the midline of the user's body so that the anode is over the user's C4-C7 region and the cathode is over the user's C7-T2 region.

4. The method of claim 1, wherein placing comprises adhesively attaching an electrode pad comprising the anode and the cathode to the back of a user's neck so that the anode and the cathode are arranged along the midline of the user's neck.

5. The method of claim 1, wherein placing the anode comprises placing a neck-worn TES controller around the neck of the user wherein the TES controller is configured to apply electrical energy between the anode and the cathode.

6. The method of claim 1, wherein applying electrical energy comprises applying TES by delivering electrical energy between the anode and the cathode, wherein the electrical energy comprises a carrier wave having a frequency that is greater than 250 Hz that is amplitude modulated at a frequency that is ten percent or less of the frequency of the carrier wave, further wherein the amplitude modulation is varied at least once every 40 seconds.

7. The method of claim 6, wherein the amplitude modulation is varied by varying the shape of an envelope of the amplitude modulation.

8. The method of claim 6, wherein the amplitude modulation is varied by varying one or both of a symmetry ratio and a flat ratio of the amplitude modulation.

9. The method of claim 1, wherein a surface area of one of the anode is greater than 1.25 times the surface area of the cathode.

10. The method of claim 1, wherein placing comprises attaching a wearable TES controller to the anode and the cathode.

11. The method of claim 1, wherein inducing the relaxed state comprises one or more of: reducing stress, reducing anxiety, improving sleep, and improve mood.

12. The method of claim 1, wherein inducing a relaxed state comprises lowering one or more of: blood pressure, heart rate, and skin conductance.

13. A method of applying transdermal electrical stimulation (TES) to induce a relaxed state, the method comprising:
  placing an anode and a cathode to a back of the user's neck along a midline of a long axis of the user's body extending anterior to posterior, wherein the anode is positioned over the user's C3-C7 region and the cathode is positioned over the user's C7-T2 region, wherein the anode and the cathode form part of an electrode pad, and wherein the anode is separated from the cathode by between 0.8 and 2.0 inches;
  applying TES by delivering electrical energy between the anode and the cathode, wherein the electrical energy comprises a carrier wave having a frequency that is greater than 250 Hz that is amplitude modulated at a frequency that is ten percent or less the frequency of the carrier wave; and
  inducing, in the user, a relaxed state by the application of TES.

14. The method of claim 13, wherein placing comprises placing a TES controller around the user's neck or shoulders wherein the TES controller is configured to apply electrical energy between the anode and the cathode.

15. The method of claim 13, wherein placing comprises attaching a wearable TES controller to the anode and the cathode.

16. The method of claim 13, wherein applying TES by delivering electrical energy comprises applying the energy at a rise time of between 1 and 20 microseconds.

17. The method of claim 16, wherein the rise-time is varied between 1 and 20 microseconds.

18. The method of claim 13, wherein applying TES comprises applying the carrier wave with a rise time of between 1 and 20 microseconds.

19. The method of claim 18, wherein the rise-time is varied between 1 and 20 microseconds.

20. The method of claim 13, wherein a surface area of one of the anode is greater than 1.25 times the surface area of the cathode.

21. The method of claim 13, wherein inducing the relaxed state comprises one or more of: reducing stress, reducing anxiety, improving sleep, and improve mood.

22. The method of claim 13, wherein inducing a relaxed state comprises lowering one or more of: blood pressure, heart rate, and skin conductance.

23. A method of applying transdermal electrical stimulation (TES) to the back of a user's neck, the method comprising:
  placing an anode and a cathode along a midline of a back of the user's neck between a region over the user's C3 cervical region and the user's T2 thoracic region, wherein the anode is separated from the cathode by between 0.6 and 1.3 inches;
  applying electrical energy between the anode and the cathode to deliver TES; and
  modulating, in the user, the user's parasympathetic drive and the user's sympathetic drive by the application of TES.

* * * * *